(12) United States Patent
Cullen et al.

(10) Patent No.: US 8,802,114 B2
(45) Date of Patent: Aug. 12, 2014

(54) PHARMACEUTICAL COMPOSITIONS OF IRON FOR ORAL ADMINISTRATION

(75) Inventors: Alan Cullen, Dublin (IE); Edel O'Toole, Dublin (IE); David C. Coughlan, Kildare (IE); Kishore Chalasani, Dublin (IE); Thomas W. Leonard, Wilmington, NC (US)

(73) Assignee: Merrion Research III Limited, Dublin (IE)

( * ) Notice: Subject to any disclaimer, the term of this patent is extended or adjusted under 35 U.S.C. 154(b) by 12 days.

(21) Appl. No.: 13/345,185

(22) Filed: Jan. 6, 2012

(65) Prior Publication Data

US 2012/0189692 A1    Jul. 26, 2012

Related U.S. Application Data

(60) Provisional application No. 61/430,575, filed on Jan. 7, 2011.

(51) Int. Cl.
| | |
|---|---|
| *A61K 9/00* | (2006.01) |
| *A61K 9/20* | (2006.01) |
| *A61K 47/48* | (2006.01) |
| *A61K 45/06* | (2006.01) |
| *A61K 33/26* | (2006.01) |

(52) U.S. Cl.
CPC ......... *A61K 47/48015* (2013.01); *A61K 9/2013* (2013.01); *A61K 47/48076* (2013.01); *A61K 45/06* (2013.01); *A61K 9/2018* (2013.01); *A61K 33/26* (2013.01)
USPC ............................ 424/400; 424/452; 424/465

(58) Field of Classification Search
None
See application file for complete search history.

(56) References Cited

U.S. PATENT DOCUMENTS

| | | |
|---|---|---|
| 4,525,339 A | 6/1985 | Behl et al. |
| 4,590,062 A | 5/1986 | Jang |
| 4,654,155 A | 3/1987 | Kipp et al. |
| 4,656,161 A | 4/1987 | Herr |
| 4,764,375 A | 8/1988 | Paradissis |
| 4,789,547 A | 12/1988 | Song et al. |
| 4,996,058 A | 2/1991 | Sinnreich |
| 5,110,606 A | 5/1992 | Geyer et al. |
| 5,169,933 A | 12/1992 | Anderson et al. |
| 5,190,748 A | 3/1993 | Bachynsky et al. |
| 5,221,734 A | 6/1993 | Burk et al. |
| 5,229,130 A | 7/1993 | Sharma et al. |
| 5,288,497 A | 2/1994 | Stanley et al. |

(Continued)

FOREIGN PATENT DOCUMENTS

| | | |
|---|---|---|
| CN | 101125132 | 2/2008 |
| EP | 0370481 A2 | 11/1989 |

(Continued)

OTHER PUBLICATIONS

EFSA Journal 2010; 8(1):1414.*

(Continued)

*Primary Examiner* — Anand Desai
*Assistant Examiner* — Melissa Mercier
(74) *Attorney, Agent, or Firm* — Myers Bigel Sibley & Sajovec, P.A.

(57) ABSTRACT

The present invention generally relates to orally administered pharmaceutical compositions of iron compounds with medium chain fatty acid salts. The invention further relates to methods of using the pharmaceutical compositions to treat iron deficiency and related disorders.

42 Claims, 12 Drawing Sheets

(56) References Cited

U.S. PATENT DOCUMENTS

| | | |
|---|---|---|
| 5,346,701 A | 9/1994 | Heiber et al. |
| 5,444,041 A | 8/1995 | Owen et al. |
| 5,506,207 A | 4/1996 | Rivier et al. |
| 5,541,155 A | 7/1996 | Leone-Bay et al. |
| 5,631,347 A | 5/1997 | Baker et al. |
| 5,633,226 A | 5/1997 | Owen et al. |
| 5,639,469 A | 6/1997 | Benes et al. |
| 5,646,109 A | 7/1997 | Owen et al. |
| 5,650,386 A | 7/1997 | Leone-Bay et al. |
| 5,688,761 A | 11/1997 | Owen et al. |
| 5,707,648 A | 1/1998 | Yiv |
| 5,714,477 A | 2/1998 | Einarsson |
| 5,736,161 A | 4/1998 | Garces et al. |
| 5,807,983 A | 9/1998 | Jiang et al. |
| 5,821,222 A | 10/1998 | Bonse et al. |
| 5,821,230 A | 10/1998 | Jiang et al. |
| 5,840,685 A | 11/1998 | Fujii et al. |
| 5,854,281 A | 12/1998 | Uekama et al. |
| 5,863,555 A | 1/1999 | Heiber et al. |
| 5,912,009 A | 6/1999 | Venkateshwaran et al. |
| 5,952,000 A | 9/1999 | Venkateshwaran et al. |
| 5,977,175 A | 11/1999 | Lin |
| 5,998,432 A | 12/1999 | Walsh et al. |
| 6,001,390 A | 12/1999 | Yum et al. |
| 6,004,984 A | 12/1999 | Goulet et al. |
| 6,017,559 A | 1/2000 | Mulqueen et al. |
| 6,017,944 A | 1/2000 | Chu et al. |
| 6,025,366 A | 2/2000 | Walsh et al. |
| 6,068,850 A | 5/2000 | Stevenson et al. |
| 6,077,847 A | 6/2000 | Walsh et al. |
| 6,077,858 A | 6/2000 | Goulet et al. |
| 6,124,261 A | 9/2000 | Stevenson et al. |
| 6,147,088 A | 11/2000 | Goulet et al. |
| 6,150,352 A | 11/2000 | Goulet et al. |
| 6,150,522 A | 11/2000 | Goulet et al. |
| 6,156,767 A | 12/2000 | Goulet et al. |
| 6,156,772 A | 12/2000 | Goulet et al. |
| 6,200,602 B1 | 3/2001 | Watts et al. |
| 6,214,798 B1 | 4/2001 | Semple et al. |
| 6,235,712 B1 | 5/2001 | Stevenson et al. |
| 6,270,804 B1 | 8/2001 | Getz et al. |
| 6,296,881 B1 | 10/2001 | Hata et al. |
| 6,326,360 B1 | 12/2001 | Kanazawa et al. |
| 6,372,728 B1 | 4/2002 | Ungell |
| 6,379,960 B1 | 4/2002 | Popoff et al. |
| 6,468,559 B1 | 10/2002 | Chen et al. |
| 6,524,557 B1 | 2/2003 | Backstrom et al. |
| 6,638,530 B1 | 10/2003 | Ishibashi et al. |
| 6,747,014 B2 | 6/2004 | Teng et al. |
| 6,747,125 B1 | 6/2004 | Hoeger et al. |
| 6,875,843 B2 | 4/2005 | Jacobson |
| 6,949,258 B2 | 9/2005 | Zhang |
| 7,098,305 B2 | 8/2006 | Deghenghi et al. |
| 7,154,002 B1 | 12/2006 | Bressi et al. |
| 7,214,662 B2 | 5/2007 | Sarlikiotis et al. |
| 7,410,957 B2 | 8/2008 | Bauss et al. |
| 7,605,123 B2 | 10/2009 | Radhakrishnan et al. |
| 7,658,938 B2 | 2/2010 | Cumming et al. |
| 7,670,626 B2 | 3/2010 | Clancy et al. |
| 7,704,977 B2 | 4/2010 | Leonard |
| 8,053,429 B2 | 11/2011 | Cumming et al. |
| 8,119,159 B2 | 2/2012 | Cumming et al. |
| 8,323,689 B2 | 12/2012 | Cumming et al. |
| 8,323,690 B2 | 12/2012 | Cumming et al. |
| 2002/0002140 A1 | 1/2002 | Holick et al. |
| 2003/0031757 A1* | 2/2003 | Akashe et al. ............ 426/66 |
| 2003/0091623 A1 | 5/2003 | Cumming et al. |
| 2003/0100509 A1 | 5/2003 | Sarlikiotis et al. |
| 2003/0114525 A1 | 6/2003 | Kammer et al. |
| 2003/0139378 A1 | 7/2003 | Daifotis et al. |
| 2003/0166508 A1 | 9/2003 | Zhang |
| 2003/0176397 A1 | 9/2003 | Lichtenberger |
| 2003/0181421 A1 | 9/2003 | Horowitz et al. |
| 2004/0087631 A1 | 5/2004 | Bacopoulos et al. |
| 2004/0147484 A1 | 7/2004 | Boyd et al. |
| 2004/0157799 A1 | 8/2004 | Seaman et al. |
| 2005/0065117 A1 | 3/2005 | Lee |
| 2005/0080075 A1 | 4/2005 | Nichols et al. |
| 2005/0119331 A1 | 6/2005 | Butler et al. |
| 2005/0157799 A1 | 7/2005 | Raman |
| 2005/0163849 A1 | 7/2005 | Wong et al. |
| 2005/0221501 A1 | 10/2005 | Arnot et al. |
| 2005/0232981 A1 | 10/2005 | Ben-Sasson |
| 2006/0135405 A1 | 6/2006 | Rischer et al. |
| 2006/0210639 A1 | 9/2006 | Liversidge et al. |
| 2007/0021357 A1 | 1/2007 | Tobia et al. |
| 2007/0021378 A1 | 1/2007 | Varki et al. |
| 2007/0060509 A1 | 3/2007 | Kanikanti et al. |
| 2007/0077313 A1 | 4/2007 | Krebs et al. |
| 2007/0148228 A1 | 6/2007 | Cumming et al. |
| 2007/0196464 A1 | 8/2007 | Cumming et al. |
| 2007/0212395 A1 | 9/2007 | Donello et al. |
| 2007/0219131 A1 | 9/2007 | Ben-Sasson |
| 2007/0238707 A1 | 10/2007 | Leonard |
| 2007/0292512 A1 | 12/2007 | Leonard et al. |
| 2008/0171848 A1 | 7/2008 | Christiansen et al. |
| 2008/0213366 A1 | 9/2008 | Gowan Jr et al. |
| 2008/0275001 A1 | 11/2008 | Cumming et al. |
| 2009/0004281 A1 | 1/2009 | Nghiem et al. |
| 2009/0060861 A1 | 3/2009 | Poulsen |
| 2009/0274758 A1 | 11/2009 | Pinhasi et al. |
| 2009/0280169 A1 | 11/2009 | Leonard |
| 2009/0280170 A1 | 11/2009 | Lee et al. |
| 2010/0022480 A1 | 1/2010 | Leonard |
| 2010/0028421 A1 | 2/2010 | Cumming et al. |
| 2010/0105627 A1 | 4/2010 | Salama et al. |
| 2010/0209499 A1 | 8/2010 | Cumming et al. |
| 2010/0215743 A1 | 8/2010 | Leonard |
| 2010/0247640 A1 | 9/2010 | Leonard |
| 2011/0182985 A1 | 7/2011 | Coughlan et al. |
| 2011/0236474 A1 | 9/2011 | Leonard et al. |
| 2012/0156294 A1 | 6/2012 | Leonard et al. |
| 2013/0089604 A1 | 4/2013 | Cumming et al. |

FOREIGN PATENT DOCUMENTS

| | | |
|---|---|---|
| EP | 0376534 A1 | 7/1990 |
| EP | 0497162 A1 | 8/1992 |
| EP | 0517211 A1 | 12/1992 |
| EP | 0580074 A1 | 1/1994 |
| EP | 0747390 A2 | 12/1996 |
| EP | 0667148 B1 | 7/2002 |
| EP | 1246839 B1 | 6/2004 |
| EP | 1674082 A1 | 6/2006 |
| EP | 1339411 | 7/2007 |
| GB | 953626 | 3/1964 |
| GB | 2212396 A | 7/1989 |
| GB | 2336311 A | 10/1999 |
| IE | (11)63119 | 3/1995 |
| JP | 59073600 | 4/1984 |
| JP | 02180837 | 7/1990 |
| JP | 2282327 | 11/1990 |
| JP | 03275633 | 12/1991 |
| JP | 04149126 | 5/1992 |
| JP | 6040949 | 2/1994 |
| JP | 06192107 | 7/1994 |
| JP | 11035458 | 2/1999 |
| JP | 2002537321 | 11/2002 |
| JP | 2004529953 | 9/2004 |
| JP | 2006089496 | 4/2006 |
| RU | 2068689 | 11/1996 |
| WO | WO 84/04674 A1 | 12/1984 |
| WO | WO 93/05903 A1 | 4/1993 |
| WO | WO 93/09785 A1 | 5/1993 |
| WO | WO 93/21907 A1 | 11/1993 |
| WO | WO 94/10983 A1 | 5/1994 |
| WO | WO 95/22319 A1 | 8/1995 |
| WO | WO 95/34294 A1 | 12/1995 |
| WO | WO 97/05903 A2 | 2/1997 |
| WO | WO 98/01159 A2 | 1/1998 |
| WO | WO 99/01579 A1 | 1/1999 |
| WO | WO 99/02120 A2 | 1/1999 |
| WO | WO 99/02485 A1 | 1/1999 |
| WO | WO 99/18972 A1 | 4/1999 |

(56) References Cited

FOREIGN PATENT DOCUMENTS

| | | |
|---|---|---|
| WO | WO 99/45934 A1 | 9/1999 |
| WO | WO 00/22909 A2 | 4/2000 |
| WO | WO 00/50012 A1 | 8/2000 |
| WO | WO 0050012 A1 * | 8/2000 |
| WO | WO 00/61111 A1 | 10/2000 |
| WO | WO 01/45636 A1 | 6/2001 |
| WO | WO 01/82903 A1 | 11/2001 |
| WO | WO 01/89479 A2 | 11/2001 |
| WO | WO 02/20037 A1 | 3/2002 |
| WO | WO 02/064148 A2 | 8/2002 |
| WO | WO 02/087597 A1 | 11/2002 |
| WO | WO 02/092070 A1 | 11/2002 |
| WO | WO 03/003999 A2 | 1/2003 |
| WO | WO 03/045419 A1 | 6/2003 |
| WO | WO 03/047493 A2 | 6/2003 |
| WO | WO 03/051373 A1 | 6/2003 |
| WO | WO 03/053401 A2 | 7/2003 |
| WO | WO 03/072123 A1 | 9/2003 |
| WO | WO 2005/055973 A2 | 6/2005 |
| WO | WO 2005/063218 A2 | 7/2005 |
| WO | WO 2005/072747 A1 | 8/2005 |
| WO | WO 2005/115331 A2 | 12/2005 |
| WO | WO 2006/010155 A2 | 1/2006 |
| WO | WO 2006/069641 A1 | 7/2006 |
| WO | WO 2006/097537 A2 | 9/2006 |
| WO | WO 2006/102117 A1 | 9/2006 |
| WO | WO 2006/103657 A1 | 10/2006 |
| WO | WO 2007/0117706 A2 | 10/2007 |
| WO | WO 2009/137080 A1 | 11/2009 |

OTHER PUBLICATIONS

Abrahamson et al., "Synthesis and characterization of iron stearate compounds," J. Inorg. Chem. 54:115-130 (1994).
Allen, "Ansel's Pharmaceutical Dosage Forms and Drug Delivery Systems," 8$^{th}$ Ed., Lippincott Williams & Wilkins, 51-58 (2005).
Anderberg et al., "Sodium Caprate Effects Dilations in Human Intestinal Tight Junctions and Enhances Drug Absorption by the Paracellular Route," Pharm. Res. 10(6):857-864 (1993).
Andriuoli et al., "Heparin by Alternative Routes of Administration", Haemostasis 20:(suppl 1):154-158 (1990).
Appendix A: Webpage publication provided by Lambent Technologies www.petroferm.com/prodinfo.asp?bus=2&mkt=4&app=3 (2006).
Artursson, "Epithelial Transport of Drugs in Cell Culture. I: A Model for Studying the Passive Diffusion of Drugs over Intestinal Absorbtive (Caco-2) Cells," J Pharm Studies 79(7):476-482 (1990).
Aungst, "Structure/effect studies of fatty acid isomers as skin penetration enhancers and skin irritants," Pharm. Res. 6:244-247 (1989).
Aungst et al., "Enhancement of the intestinal absorption of peptides and non-peptides," J. Control. Release 41:19-31 (1996).
Baker et al., "Role of Body Surface Area in Dosing of Investigatioanl Agents in Adults, 1991-2001," J. Natl. Cancer Inst. 94:1883-1888 (2002).
Bennett et al., "Pulmonary Delivery of Detirelex by Intratracheal Instillation and Aerosol Inhalation in the Briefly Anesthetized Dog," Pharm. Res. 11:1048-1054 (1994).
Brayden et al., "Heparin Absorption Across the Intestine: Effects of Sodium N-[8-(2-Hydroxybenzoyl)Amino]Caprylate in Rat In Situ Intestinal Instillations and in Caco-2 Monolayers," Pharm. Res. 14(12):1772-1779 (1997).
Chan et al., "Depsipeptide (FR901228, Nsc-630176) pharmacokinetics in the rat by LC/MS/MS," Invest. New Drugs 15:195-206 (1997).
Choay et al., "Structure-activity relationship in heparin: A synthetic pentasaccharide with high affinity for antithrombin III and eliciting high anti-factor Xa activity," Biochem. Biophys. Res. Commun. 116:492-499 (1983).
Cosman, F. et al., "Clinical Evaluation of Novel Bisphosphonate Dosing Regimens in Osteoporosis: The Role of Comparative Studies and Implications for Future Studies", Clin. Ther. 29: 1116-1127 (Jul. 18, 2007).
Cumming et al., "In vitro evaluation of a series of sodium carboxylates as dermal penetration enhancers," Int J Pharm 108:141-148 (1994).
Declaration of Dr. Thomas W. Leonard from European Patent Application EP 00905186.3 (2007).
Doluisio et al., "Drug Absorption I: An In Situ Rat Gut Technique Yielding Realistic Absorption Rates," J. Pharm. Studies 58(10):1196-1200 (1969).
Drummond et al., "Clinical development of histone deacetylase inhibitors as anticancer agents," Annu. Rev. Pharmacol. Toxicol. 45:495-528 (2005).
Fernandez et al., "Comparative study on digestive lipase activities on the self emulsifying excipient Labrasol®, medium chain glycerides and PEG esters," Biochim. Biophys. Acta 1771:633-640 (2007).
Gennaro, "Remington: The Science and Practice of Pharmacy," 19th Edition, Mack Publishing Co., p. 1618 (1995).
Grohganz et al., "Development and in vitro evaluation of a liposome based implant formulation for the decapeptide cetrorelix," Eur. J. Pharm. Biopharm. 59:439-448 (2004).
Hahn, "Chemotherapy Dose Calculation and Administration in Exotic Animal Species," Sem. Avian Exotic Pet Med. 14:193-198 (2005).
Hild et al., "The ability of a gonadotropin-releasing hormone antagonist, acyline, to prevent irreversible infertility induced by the indenopyridine, CDB-4022, in adult male rats: the role of testosterone," Biol. Reproduction 71:348-358 (2004).
Jiang et al,, "GnRH antagonists: a new generation of long acting analogues incorporating $p$-ureido-phenylalanines at positions 5 and 6," J. Med. Chem. 44:453-467 (2000).
Kajii et al., "Fluorescence study of the membrane-perturbing action of sodium caprylate as related to promotion of drug absorption," J. Pharm. Sci. 77:390-392 (1988).
Kishimoto, H. et al., "Efficacy and tolerability of once-weekly administration of 17.5mg risedronate in Japanese patients with involutional osteoporosis: a comparison with 2.5-mg once-daily dosage regimen", J. Bone Miner. Metab. 24: 405-413 (Sep. 1, 2006).
Lesnyak, "Medicamental methods of treating osteoporosis," Gynecology, vol. 7 (2005); accessed at www.consilium-medicum.com/article/7685.
Lambent Technologies, "Technical Data Sheet for Lumulse L-4, Lumulse L-12, and Lumulse L-23", pp. 1-2 (2004).
Lambent Technologies, "Material Safety Data Sheet for Lumulse L-12", pp. 1-3 (2004).
Lindmark et al., "Mechanisms of Absorption Enhancement by Medium Chain Fatty Acids in Intestinal Epithelial Caco-2 Cell Monolayers," J. Pharmacol. Exp. Ther. 275(2):958-964 (1995).
Lindmark et al., "Mechanism of Absorption Enhancement in Humans After Rectal Administration of Ampicillin in Suppositories Containing Sodium Caprate," Pharm. Res. 14(7):930-935 (1997).
Massa et al., "3-(4-Aroyl-1$H$-pyrrol-2-yl)-$N$-hydroxy-2-propenamides, a New Class of Synthetic Histone Deacetylase Inhibitors," J. Med. Chem. 44:2069-2072 (2001).
"McGraw-Hill Dictionary of Chemical Terms", McGraw-Hill Book Company Ed. S.P. Parker, New York pp. 208, 209, 251 (1985).
Mechanick et al., "Effect of a Convenient Single 90-mg Pamidronate Dose on Biochemical Markers of Bone Metabolism in Patients With Acute Spinal Cord Injury," J. Spinal Cord Med. 29(4):406-412 (2006).
Mishima et al., "Studies on the Promoting Effects of Medium Chain Fatty Acid Salts on the Nasal Absorption of Insulin in Rats," J. Pharmacobio-Dyn. 10:624-631 (1987).
Motlekar, "Oral delivery of low-molecular-weight heparin using sodium caprate as absorption enhancer reaches therapeutic levels," J. Drug Targeting 13(10):573-583 (2005).
Moradei et al., "Histone deacetylase inhibitors: Latest developments, trends and prospects," Curr. Med. Chem. 5(5):529-560 (2005).
Morishita et al., "Site-Dependent Effect of Aprotinin, Sodium Caprate, Na2EDTA and Sodium Glycocholate on Intestinal Absorption of Insulin," Biol. Pharm. Bull. 16:68-72 (1993).
Murakami et al., "Effect of Oleic Acid Vesicles on Intestinal Absorption of Carboxyfluorescein in Rats", Pharm, Res. 3(1):35-40 (1986).
Muranishi, "Absorption Enhancers," Crit. Rev. Ther. Drug Carrier Systems 7:1-33 (1990).

(56) References Cited

OTHER PUBLICATIONS

Muranushi et al., "The Effects of Fatty Acids and Their Derivatives on the Intestinal Absorption of Insulin in Rat," Drug Dev. Indust. Pharm. 19(8):929-941 (1993).
Octreotide, Wikipedia. Printed Mar. 23, 2009. 3 pp.
Oda (Inamori), "Absorption Enhancement of Argatroban by Medium Chain Fatty Acid Sodium Salts," Proceedings Int'l Symp. Control. Rel. Bioact. Mater. 24:283-284 (1997).
Palin et al., "The oral absorption of cefoxitin from oil and emulsion vehicles in rats," Int. J. of Pharmaceutics 33:99-104 (1986).
Poster Presentation entitled "A Phase I Trial and Pharmacokinetic Study of Depsipeptide in Pediatric Patients with Refractory Solid Tumors: A Children's Oncology Group Study" at American Society of Clinical Oncology meeting, May 2005, abstract 8528 (Fouladi et al.).
Sawada et al., "Role of Paracellular Pathway in Nonelectrolyte Permeation Across Rat Colon Epithelium Enhanced by Sodium Caprate and Sodium Caprylate," Pharm. Res. 8(11):1365-1371 (1991).
Sawyer et al., "Body surface area as a determinant of pharmacokinetics and drug dosing," Invest. New Drugs 19:171-177 (2001).
Schneider et al., "Evaluation of drug penetration into human skin ex vivo using branched fatty acids and propylene glycol," Int. J. Pharm. 145:187-196 (1996).
Schnitzer, T. et al., "Therapeutic equivalence of alendronate 70mg once-weekly and alendronate 10mg daily in the treatment of osteoporosis", Aging Clin. Exp. Res. 12:1-12 (Jan. 2000).
Sikora, "Cancer drug development in the post-genomic age," Curr. Sci. 81:549-54 (2001).
Simpson et al., "Significance of non-esterified fatty acids in iron uptake by intestinal brush-border membrane vesicles," Biochim. Biophys. Acta 941:39-47 (1988).
Sinko, "Martin's Physical Pharmacy and Pharmaceutical Sciences," 5th Ed., Lippincott Williams & Wilkins, 355-357 (2006).
Somatostatin, Wikipedia. Printed Mar. 23, 2009. 4 pp.
Tanaka et al. "Enhancement of intestinal transport of thyrotropin-releasing hormone via a carrier-mediated transport system by chemical modification with lauric acid," Biochim. Biophys. Acta 1283:119-126 (1996).
Tomita et al., "Absorption-Enhancing Mechanism of Sodium Caprate and Decanoylcarnitine in Caco-2 Cells," J. Pharmacol. Exp. Ther. 272(2):739-743 (1995).
Tomita et al., "Enhancement of Colonic Drug Absorption by the Transcellular Permeation Route," Pharm. Res. 5(12):786-789 (1988).
Tomita et al., "Enhancement of Colonic Drug Absorption by the Paracellular Permeation Route," Pharm. Res. 5(6):341-346 (1988).
Tomita et al., "Differences in the Enhancing Effects of Sodium Caprate on Colonic and Jejunal Drug Absorption," Pharm. Res. 9(5):648-653 (1992).
WPI Database, Accession No. 1984-142694, English language abstract of JP 59073600.
WPI Database, Accession No. 1992-028863, English language abstract of JP 03275633.
WPI Database, Accession No. 1997-287727, English language abstract of RU 2068689.
Yamamoto et al., "Pulmonary absorption enhancement of peptides by absorption enhancers and protease inhibitors," J. Control. Release 41:57-67 (1996).
Yamamoto et al., "Improvement of intestinal absorption of peptide and protein drugs by chemical modification with fatty acids," Nihon Rinsho 56(3):601-607 (1998).
Yang et al., Deposition of insulin powders for inhalation in vitro and pharmacodynamic evaluation of absorption promoters in rats, Acta Pharmaceutica Sinica 40:1069-1074 (2005).
Yeh et al., "Effect of Medium-Chain Glycerides on Physiological Properties of Rabbit Intestinal Epithelium in Vitro," Pharm. Res. 11(8):1148-1154 (1994).
Zhou et al., "Effects of cholic acid and other enhancers on the bioavailability of insulin from a subcutaneous site," Int. J. Pharm. 69:29-41 (1991).
Zips et al., "New anticancer agents: In vitro and In vivo evaluation," In vivo 19:108 (2005).
U.S. Appl. No. 09/510,560, filed Feb. 22, 2000; Office Action mailed Mar. 26, 2001.
U.S. Appl. No. 09/510,560, filed Feb. 22, 2000; Office Action mailed Jul. 15, 2002.
U.S. Appl. No. 09/510,560, filed Feb. 22, 2000; Office Action mailed Oct. 22, 2003.
U.S. Appl. No. 09/510,560, filed Feb. 22, 2000; Office Action mailed Jun. 4, 2004.
U.S. Appl. No. 09/510,560, filed Feb. 22, 2000; Office Action mailed May 18, 2005.
U.S. Appl. No. 09/510,560, filed Feb. 22, 2000; Office Action mailed Nov. 21, 2005.
U.S. Appl. No. 09/510,560, filed Feb. 22, 2000; Office Action mailed Jun. 14, 2006.
U.S. Appl. No. 09/510,560, filed Feb. 22, 2000; Office Action mailed Dec. 15, 2006.
U.S. Appl. No. 09/510,560, filed Feb. 22, 2000; Office Action mailed Aug. 23, 2007.
U.S. Appl. No. 09/510,560, filed Feb. 22, 2000; Office Action mailed Feb. 20, 2008.
U.S. Appl. No. 09/510,560, filed Feb. 22, 2000; Office Action mailed Sep. 17, 2008.
U.S. Appl. No. 09/510,560, filed Feb. 22, 2000; Office Action mailed May 27, 2009.
U.S. Appl. No. 11/400,689, filed Apr. 7, 2006; Office Action mailed Feb. 12, 2009.
U.S. Appl. No. 11/450,641, filed Jun. 9, 2006; Office Action mailed Jun. 25, 2009.
U.S. Appl. No. 11/450,641, filed Jun. 9, 2006; Office Action mailed Apr. 14, 2010.
U.S. Appl. No. 11/450,641, filed Jun. 9, 2006; Office Action mailed Nov. 9, 2011.
U.S. Appl. No. 12/172,707, filed Jul. 14, 2008; Office Action mailed Jan. 4, 2011.
U.S. Appl. No. 12/172,707, filed: Jul. 14, 2008; Office Action mailed Apr. 27, 2011.
U.S. Appl. No. 12/172,707, filed: Jul. 14, 2008; Office Action mailed Nov. 9, 2011.
U.S. Appl. No. 12/172,707, filed: Jul. 14, 2008; Office Action mailed Feb. 21, 2012.
U.S. Appl. No. 12/553,196, filed Sep. 3, 2009; Office Action mailed Sep. 24, 2010.
U.S. Appl. No. 12/553,196, filed Sep. 3, 2009; Office Action mailed Mar. 31, 2011.
U.S. Appl. No. 12/768,008, filed Apr. 27, 2010; Office Action mailed Aug. 2, 2011.
U.S. Appl. No. 12/768,008, filed Apr. 27, 2010; Office Action mailed Feb. 29, 2012.
U.S. Appl. No. 11/733,007, filed: Apr. 9, 2007; Office Action mailed Jan. 29, 2009.
U.S. Appl. No. 11/733,007, filed Apr. 9, 2007; Office Action mailed Aug. 17, 2009.
U.S. Appl. No. 12/481,952, filed Jun. 10, 2009; Office Action mailed Jul. 26, 2011.
U.S. Appl. No. 12/481,952, filed Jun. 10, 2009; Office Action mailed Nov. 23, 2011.
U.S. Appl. No. 12/767,076, filed Apr. 26, 2010; Office Action mailed Feb. 9, 2012.
U.S. Appl. No. 12/767,076, filed Apr. 26, 2010; Office Action mailed May 31, 2012.
U.S. Appl. No. 11/761,233, filed Jun. 11, 2007; Office Action mailed Sep. 1, 2009.
U.S. Appl. No. 11/761,233, filed Jun. 11, 2007; Office Action mailed Jun. 28, 2010.
U.S. Appl. No. 12/436,990, filed May 7, 2009; Office Action mailed Sep. 14, 2010.
U.S. Appl. No. 12/436,990, filed May 7, 2009; Office Action mailed Mar. 16, 2011.
U.S. Appl. No. 12/436,990, filed May 7, 2009; Office Action mailed Oct. 7, 2011.

(56) References Cited

OTHER PUBLICATIONS

U.S. Appl. No. 12/437,012, filed May 7, 2009; Office Action mailed Mar. 6, 2012.
U.S. Appl. No. 12/712,527, filed Feb. 25, 2010; Office Action mailed Sep. 26, 2012.
International Application No. PCT/US2012/020487, filed Jan. 6, 2012, international search report and written opinion.
Bird, "Genetic aspects of Alzheimer disease," Genet. Med. 10:231-239 (2008).
Breddin, "The role of antithrombin agents and Factor Xa-inhibitors in antithrombotic treatment," Turk. J. Haematol. 19:113-120 (2002).
Herbst, "Gonadotropin-releasing hormone antagonists," Curr. Opin. Pharmacol. 3:660-666 (2003).
Kalweit et al., "Pulmonary embolism: a frequent cause of acute fatality after lung resection," Eur. J. Cardio-thorac. Surg. 10:242-247 (1996).
Kleinebudde, "Roll compaction/dry granulation: pharmaceutical applications," Eur. J. Pharm. Biopharm. 58:317-326 (2004).
Tak et al., "The pathogenesis and prevention of joint damage in rheumatoid arthritis," Arthritis Rheumatism 43:2619-2633 (2000).
Wood-Kaczmar et al., "Understanding the molecular causes of Parkinson's disease," Trends Mel. Med. 12:621-528 (2006).
U.S. Appl. No. 13/014,156, filed Jan. 26, 2011; Office Action mailed Jun. 6, 2013.
U.S. Appl. No. 12/712,527, filed Feb. 25, 2010; Office Action mailed May 20, 2013.
U.S. Appl. No. 13/242,601, filed Sep. 23, 2011; Office Action mailed Jun. 4, 2013.
U.S. Appl. No. 13/073,202, filed Mar. 28, 2011; Office Action mailed Oct. 24, 2013.
European Application No. 12732499.4, filed Jan. 6, 2012, search report mailed May 6, 2014.
Goodnough et al., "Erythropoietin, iron, and erythropoiesis," Blood 96:823-833 (2000).

\* cited by examiner

PHARMACEUTICAL COMPOSITIONS OF IRON FOR ORAL ADMINISTRATION

RELATED APPLICATIONS

This application claims the benefit under 35 U.S.C. §119 (e) of U.S. Provisional Patent Application Ser. No. 61/430,575, filed Jan. 7, 2011, the disclosure of which is incorporated herein by reference in its entirety.

FIELD OF THE INVENTION

The present invention generally relates to orally administered pharmaceutical compositions of iron compounds with medium chain fatty acid salts. The invention further relates to methods of using the pharmaceutical compositions to treat iron deficiency and related disorders.

BACKGROUND OF THE INVENTION

Iron in a variety of forms is administered for the treatment of iron deficiency and related disorders (e.g., anemia) as well as prophylactically to supply the minimum daily recommended allowance. A variety of iron compounds have been administered, including ferric and ferrous forms of elemental iron as salts, complexes, hydrates, chelates, and bound to polymer. Current oral iron preparations have low bioavailability and substantial side effects associated with them. Numerous formulation attempts have been made to create dosage forms that provide adequate iron absorption to treat deficiencies with less side effects. The side effects from oral administration primarily are a result of the large doses necessary to promote adequate absorption. It is likely that the presence of unabsorbed iron that remains in the gastrointestinal (GI) tract also significantly contributes to irritation, therefore side effects are also related to the poor bioavailability. The side effects include abdominal pain, heartburn, constipation, diarrhea, nausea, and vomiting. The inadequate absorption by oral delivery combined with poor compliance from the adverse effects on the GI tract means that in cases of substantial iron deficiencies, therapy must be carried out by parenteral injection, either intravenously or intramuscularly. Parenteral therapy is also associated with substantial side effects, including anaphylactic shock, injection site issues, hypotension, muscle cramps, dizziness, headache, graft complications, hypertension, chest pain, dysguesia, ear pain, and peripheral edema, as well as the cost and discomfort associated with injectable medication.

There is a need for improved oral formulations that achieve much better bioavailability. Such a formulation allows therapeutic doses to be given by a non-parenteral route while providing decreased side effects compared to present formulations. Such an improved formulation can be used to replace parenteral therapy, and further improve patient quality of life. By improving the oral bioavailability, the total dose and the residual amounts of iron in the GI tract will be lowered which will improve the side effect profile, improve compliance, and allow a therapeutic effect approaching that of the injectable products to be achieved. Oral doses can then be used to achieve the required blood concentrations and body loads which now can only be achieved via parenteral doses to improve hemoglobin and ferritin levels, e.g., in severely anemic patient.

Rapid release oral iron formulations are preferred since iron is best absorbed in the upper small intestine. Controlled and extended release formulations are not effective for iron since there is minimal lower intestinal and colonic absorption. The ideal site for absorption is the upper small intestine, where active transport/divalent metal transporters and favorable pH promote absorption.

WO 2005/041928 describes a composition comprising iron and a transport moiety, such as a fatty acid. The composition is prepared in a manner such that the iron and the transport moiety form a tight ion binding pair, i.e., a salt. Creation of new salt forms for iron has inherent issues associated with it, including the need to establish safety, stability, and commercial manufacturing procedures. Development of a formulation that can work with existing salts and/or chelates is much preferred.

There is a continuing need for development of novel pharmaceutical formulations of iron suitable for oral administration, which not only offer the convenience of oral dosing, but also provide increased bioavailability of iron without excessive side effects.

SUMMARY OF THE INVENTION

The present invention relates to pharmaceutical compositions and oral dosage forms of iron and an absorption enhancer. The compositions provide increased bioavailability of iron. The compositions also overcome the negative feedback mechanism that limits iron absorption.

In one aspect, the invention provides a pharmaceutical composition for oral administration comprising, consisting essentially of or consisting of an iron compound and an absorption enhancer, wherein the absorption enhancer is a medium chain fatty acid salt having a carbon chain length of from about 4 to about 20 carbon atoms. In some aspects, the composition does not involve chemical modification of the iron compound. In other aspects, the iron compound and the absorption enhancer are not part of a tight ion binding pair. The invention allows the use of conventional iron compounds (e.g., salts of iron, such as ferrous sulfate, or chelates and complexes of iron, such as EDTA and pyrophosphate complexes) to be used in oral dosage forms containing medium chain fatty acid salts. The oral dosage forms include solid dosage forms such as tablets, capsules, and powders and liquid dosage forms such as solutions, suspensions, elixirs, and syrups.

In a further aspect, the invention relates to a pharmaceutical composition for oral administration comprising an iron compound and an absorption enhancer, wherein the composition provides a bioavailability of iron that is at least 1.5 times greater than the bioavailability provided by a composition comprising ferrous sulfate that does not contain an absorption enhancer.

In another aspect, the invention relates to an oral dosage form (e.g., a solid, semi-solid, or liquid oral dosage form) comprising, consisting essentially of, or consisting of the pharmaceutical composition of the invention.

In another aspect, the invention relates to a method of orally delivering iron to a subject, comprising administering to the subject the oral dosage form of the invention.

In another aspect, the invention relates to a method for increasing the level of iron in a subject in need thereof, e.g., in the blood of a subject in need thereof, comprising administering to the subject the oral dosage form of the invention.

In another aspect, the invention relates to a method for increasing the level of hemoglobin in the blood of a subject in need thereof, comprising administering to the subject the oral dosage form of the invention.

In another aspect, the invention relates to a method for treating an iron deficiency in a subject in need thereof, comprising administering to the subject the oral dosage form of the invention.

In another aspect, the invention relates to a method for maintaining iron indices in a subject to ensure maximum efficacy of erythropoietin and/or other erythropoiesis-stimulating agents, comprising administering to the subject the oral dosage form of the invention.

In another aspect, the invention relates to a method for treating a disease or disorder characterized by an iron deficiency in a subject in need thereof, comprising administering to the subject the oral dosage form of the invention.

DETAILED DESCRIPTION

Figure 1:
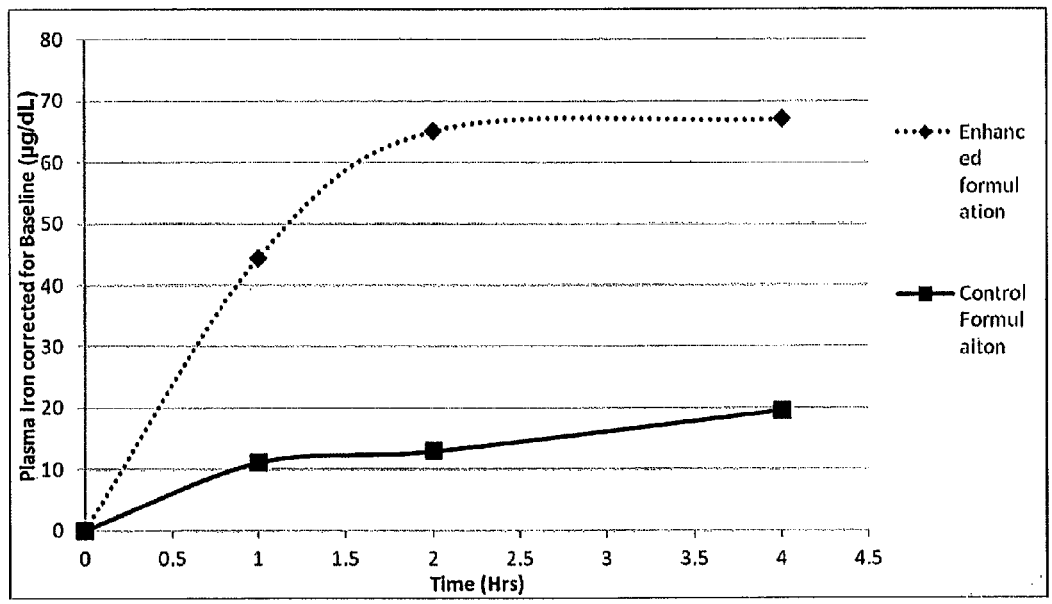
FIG. 1 shows the plasma iron concentration vs. time profiles of the test formulations after period 1 and period 2 dosing in dogs.

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

All patents, patent applications and publications referred to herein are incorporated by reference in their entirety. In case of a conflict in terminology, the present specification is controlling.

The terminology used in the description of the invention herein is for the purpose of describing particular embodiments only and is not intended to be limiting of the invention.

As used in the description of the embodiments of the invention and the appended claims, the singular forms "a", "an" and "the" are intended to include the plural forms as well, unless the context clearly indicates otherwise.

As used herein, "and/or" refers to and encompasses any and all possible combinations of one or more of the associated listed items.

The term "about," as used herein when referring to a measurable value such as an amount of a compound, dose, time, temperature, and the like, is meant to encompass variations of 20%, 10%, 5%, 1%, 0.5%, or even 0.1% of the specified amount.

The terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

The term "tablet" as used herein includes, but is not limited to, immediate release (IR) tablets, sustained release (SR)

tablets, matrix tablets, multilayer tablets, multilayer matrix tablets, extended release tablets, delayed release tablets and pulsed release tablets, any or all of which may optionally be coated with one or more coating materials, including polymer coating materials, such as enteric coatings, rate-controlling coatings, semi-permeable coatings and the like. The term "tablet" also includes osmotic delivery systems in which a drug compound is combined with an osmagent (and optionally other excipients) and coated with a semi-permeable membrane, the semi-permeable membrane defining an orifice through which the drug compound may be released. Tablet solid oral dosage forms that may be useful in the practice of the invention include those selected from the group consisting of IR tablets, SR tablets, coated IR tablets, coated SR tablets, matrix tablets, coated matrix tablets, multilayer tablets, coated multilayer tablets, multilayer matrix tablets and coated multilayer matrix tablets. In some embodiments, a tablet dosage form is an enteric-coated tablet dosage form. In some embodiments, a tablet dosage form is an enteric-coated rapid onset tablet dosage form.

The term "capsule" as used herein includes, but is not limited to, IR capsules, SR capsules, coated IR capsules, and coated SR capsules including delayed release capsules. Capsules may be filled with powders, granules, multiparticulates, tablets, semi-solids, or liquids. In some embodiments, a capsule dosage form is an enteric-coated capsule dosage form. In some embodiments, a capsule dosage form is an enteric-coated rapid onset capsule dosage form. Capsules may be made of hard gelatin, soft gelatin, starch, cellulose polymers, or other materials as known to the art.

The term "multiparticulate" as used herein means a plurality of discrete particles, pellets, mini-tablets and mixtures or combinations thereof. If the oral form is a multiparticulate capsule, hard or soft gelatin capsules or capsules of other materials can suitably be used to contain the multiparticulate. In some embodiments, a sachet can suitably be used to contain the multiparticulate. In some embodiments, the multiparticulate may be coated with a layer containing rate controlling polymer material. In some embodiments, a multiparticulate oral dosage form according to the invention may comprise a blend of two or more populations of particles, pellets, or mini-tablets having different in vitro and/or in vivo release characteristics. For example, a multiparticulate oral dosage form may comprise a blend of an instant release component and a delayed release component contained in a suitable capsule.

In some embodiments, the multiparticulate and one or more auxiliary excipient materials can be compressed into tablet form such as a multilayer tablet. In some embodiments, a multilayer tablet may comprise two layers containing the same or different levels of the same active ingredient having the same or different release characteristics. In some embodiments, a multilayer tablet may contain different active ingredient in each layer. Such a tablet, either single layered or multilayered, can optionally be coated with a controlled release polymer so as to provide additional controlled release properties. In some embodiments, a multiparticulate dosage form comprises a capsule containing delayed release rapid onset minitablets. In some embodiments, a multiparticulate dosage form comprises a delayed release capsule comprising instant release minitablets. In some embodiments, a multiparticulate dosage form comprises a capsule comprising delayed release granules. In some embodiments, a multiparticulate dosage form comprises a delayed release capsule comprising instant release granules. In some embodiments the particulates may all be of uniform composition. In some embodiments, the particulates may vary in composition.

By the terms "treat," "treating," or "treatment of" (and grammatical variations thereof) it is meant that the severity of the subject's condition is reduced, at least partially improved, or stabilized and/or that some alleviation, mitigation, decrease, or stabilization in at least one clinical symptom and/or parameter is achieved and/or there is a delay in the progression of the disease or disorder.

The terms "prevent," "preventing," and "prevention" (and grammatical variations thereof) refer to avoidance, prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

An "effective amount," as used herein, refers to an amount that imparts a desired effect, which is optionally a therapeutic or prophylactic effect.

A "treatment effective" amount, as used herein, is an amount that is sufficient to provide some improvement or benefit to the subject. Alternatively stated, a "treatment effective" amount is an amount that will provide some alleviation, mitigation, decrease, or stabilization in at least one clinical symptom in the subject. Those skilled in the art will appreciate that the therapeutic effects need not be complete or curative, as long as some benefit is provided to the subject.

A "prevention effective" amount, as used herein, is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

As used herein, a "therapeutically effective" or "therapeutically acceptable" amount refers to an amount that will elicit a therapeutically useful response in a subject. The therapeutically useful response may provide some alleviation, mitigation, or decrease in at least one clinical symptom in the subject. The terms also include an amount that will prevent or delay at least one clinical symptom in the subject and/or reduce and/or delay the severity of the onset of a clinical symptom in a subject relative to what would occur in the absence of the methods of the invention. Those skilled in the art will appreciate that the therapeutically useful response need not be complete or curative or prevent permanently, as long as some benefit is provided to the subject.

"Subjects" according to the present invention include mammals, avians, reptiles, amphibians, and fish. In some embodiments, the subjects are mammalian subjects including, but not limited to, humans, non-human mammals, non-human primates (e.g., monkeys, chimpanzees, baboons, etc.), dogs, cats, mice, hamsters, rats, horses, cows, pigs, rabbits, sheep, and goats. Avian subjects include, but are not limited to, chickens, turkeys, ducks, geese, quail, and pheasant, and birds kept as pets (e.g., parakeets, parrots, macaws, cockatoos, and the like). In particular embodiments, the subject is from an endangered species. In particular embodiments, the subject is a laboratory animal. Human subjects include neonates, infants, juveniles, adults, and geriatric subjects. In certain embodiments, the subject is in need of the methods of the present invention, e.g., has an iron deficiency. In other embodiments, the subject has, may have, or is at risk for an iron deficiency.

The phrase "the composition does not involve chemical modification of the iron compound" refers to the fact that the iron compound is not chemically modified by or chemically interact with (i.e., form covalent or ionic bonds) any component in the composition during preparation, storage, and use of the composition.

A "tight ion binding pair," as used herein, refers to a pair of ions that are, at physiological pH and in an aqueous environment, not readily interchangeable with other loosely paired or free ions that may be present in the environment of the tight ion binding pair. A tight ion binding pair can be experimentally detected by noting the absence of an interchange of a member of the pair with another ion, at physiologic pH and in an aqueous environment, using isotopic labeling and NMR or mass spectroscopy. Tight ion binding pairs also can be found experimentally by noting the lack of separation of the ion pair, at physiologic pH and in an aqueous environment, using reverse phase HPLC.

An "iron compound," as used herein, refers to a complex comprising elemental iron and an additional atom, ion, or molecule, and includes iron salts, iron chelates, iron complexes, and polymer-bound iron.

An "iron complex," as used herein, refers to elemental iron in neutral or cationic form covalently or electrostatically linked to an additional atom, ion, or molecule.

An "iron chelate," as used herein, refers to an iron cation and anions that surround the iron cation and are joined to it by electrostatic bonds.

An "active agent," as used herein, refers to a compound or molecule that has a therapeutic, prophylactic, or nutritive effect when delivered to a subject.

A "disease or disorder characterized by an iron deficiency," as used herein, refers to any disease or disorder in which whole body stores of iron are less than desired. Low body stores may be indicated by various symptoms including a blood level of iron that is below normal, low ferritin levels, and/or low hemoglobin levels. Exemplary low levels may be a cause and/or symptom of the disease or disorder and includes any disease or disorder in which elevating iron levels in the subject, e.g., in the blood, treats and/or prevents one or more symptoms of the disease or disorder, or where maintenance of iron indices is required for effectiveness of another agent, e.g., erythropoiesis-stimulating agents. The normal serum iron level for human adults is considered to be about 50 to about 170 µg/dL.

The present invention provides a pharmaceutical composition for oral administration comprising, consisting essentially of, or consisting of an iron compound (e.g., an iron salt, chelate, complex, or polymer bound) and an absorption enhancer, wherein the absorption enhancer is a medium chain fatty acid salt having a carbon chain length of from about 4 to about 20 carbon atoms. In some embodiments, the iron compound is an iron chelate or iron complex. In some embodiments, the composition does not involve chemical modification of the iron compound. In some embodiments, the iron compound and the absorption enhancer are not part of a tight ion binding pair. In some embodiments, the use of an iron chelate or iron complex in which iron is tightly bound to another moiety prevents the formation of a tight ion binding pair between the iron and the fatty acid. In certain embodiments, the iron compound is present in the composition in a treatment effective amount. In other embodiments, the iron compound is present in the composition in a prevention effective amount. In certain embodiments, the pharmaceutical composition comprises, consists essentially of, or consists of one or more auxiliary excipients in addition to the iron compound and absorption enhancer.

In a further aspect, the invention relates to a pharmaceutical composition for oral administration comprising, consisting essentially of, or consisting of an iron compound (e.g., an iron salt, chelate, complex, or polymer bound) and an absorption enhancer, wherein the composition provides a bioavailability of iron that is at least 1.5 times greater than the bioavailability provided by conventional oral iron preparations (e.g., a composition comprising ferrous sulfate (e.g., a ferrous sulfate tablet) or any other currently available iron dosage form), e.g., one that does not contain an absorption enhancer. In certain embodiments, the bioavailability of iron is at least 1.5, 2, 3, 4, 5, 6, 7, 8, 9, or 10 times greater or more than the bioavailability provided by conventional oral iron preparations.

In some embodiments, the iron compound is an iron salt (e.g., a ferrous salt or a ferric salt), an iron chelate, an iron complex, or polymer bound iron. In certain embodiments, the iron compound is a ferric compound, as it may produce less side effects than ferrous compounds.

Iron salts include, but are not limited to, ferrous sulfate, ferrous gluconate, ferrous fumarate, ferric hypophosphite, ferric albuminate, ferric chloride, ferric citrate, ferric oxide saccharate, ferric ammonium citrate, ferrous chloride, ferrous iodide, ferrous lactate, ferric trisglycinate, ferrous bisglycinate, ferric nitrate, ferrous hydroxide saccharate, ferric sulfate, ferric gluconate, ferric aspartate, ferrous sulfate heptahydrate, ferrous phosphate, ferric ascorbate, ferrous formate, ferrous acetate, ferrous malate, ferrous glutamate, ferrous cholinisocitrate, ferroglycine sulfate, ferric oxide hydrate, ferric pyrophosphate soluble, ferric hydroxide saccharate, ferric manganese saccharate, ferric subsulfate, ferric ammonium sulfate, ferrous ammonium sulfate, ferrous ethylenediammonium sulfate tetrahydrate, ferric sesquichloride, ferric choline citrate, ferric manganese citrate, ferric quinine citrate, ferric sodium citrate, ferric sodium edetate, ferric formate, ferric ammonium oxalate, ferric potassium oxalate, ferric sodium oxalate, ferric peptonate, ferric manganese peptonate, ferric acetate, ferric fluoride, ferric phosphate, ferric pyrophosphate, ferrous pyrophosphate, ferrous carbonate saccharate, ferrous carbonate mass, ferrous succinate, ferrous citrate, ferrous tartrate, ferric fumarate, ferric succinate, ferrous hydroxide, ferrous nitrate, ferrous carbonate, ferric sodium pyrophosphate, ferric tartrate, ferric potassium tartrate, ferric subcarbonate, ferric glycerophosphate, ferric saccharate, ferric hydroxide saccharate, ferric manganese saccharate, ferrous ammonium sulfate, ferric sodium pyrophosphate, ferrous carbonate, ferric hydroxide, ferrous oxide, ferric oxyhydroxide, ferrous oxalate, and/or combinations thereof.

Iron chelates and complexes include, but are not limited to, ferric pyrophosphate, soluble ferric pyrophosphate, iron polysaccharide, iron bis glycinate, iron proteinate, methylidine-iron complex, EDTA-iron complex, phenanthrolene iron complex, p-toluidine iron complex, ferrous saccharate complex, ferrlecit, ferrous gluconate complex, ferrum vitis, ferrous hydroxide saccharate complex, iron-arene sandwich complexes, acetylacetone iron complex salt, iron-dextran complex, iron-dextrin complex, iron-maltodextrin complex, iron-sorbitol-citric acid complex, saccharated iron oxide, ferrous fumarate complex, iron porphyrin complex, iron phtalocyamine complex, iron cyclam complex, dithiocarboxy-iron complex, desferrioxamine-iron complex, bleomycin-iron complex, ferrozine-iron complex, iron perhaloporphyrin complex, alkylenediamine-N,N'-disuccinic acid iron(III) complex, hydroxypyridone-iron(III) complex, aminoglycoside-iron complex, transferrin-iron complex, iron thiocyanate complex, iron complex cyanides, porphyrinato iron(III) complex, polyaminopolycarbonate iron complexes, dithiocarbamate iron complex, adriamycin iron complex, anthracycline-iron complex, MGD-iron complex, ferrioxamine B, ferrous citrate complex, ferrous sulfate complex, ferric gluconate complex, ferrous succinate complex, polyglucopyranosyl iron complex, polyaminodisuccinic acid iron complex, biliverdin-iron complex, deferiprone iron complex, ferric oxyhydride-dextran complex, dinitrosyl dithiolato iron complex, iron lactoferrin complexes, 1,3-PDTA ferric complex salts, diethylenetriaminepentaacetic acid iron complex salts, cyclohexanediaminetetraacetic acid iron complex salts, methyliminodiacetic acid iron complex salts, glycol ether diaminetetraacetic acid iron complex salts, ferric hydroxypyrone complexes, ferric succinate complex, ferric chloride complex, ferric glycine sulfate complex, ferric aspartate complex, sodium ferrous gluconate complex, ferrous hydroxide polymaltose complex, and/or combinations thereof.

Suitable iron compounds for use in the pharmaceutical compositions of the invention can be determined using techniques well known in the art and described herein. For example, the centrifugation techniques described in Example 2 below can be used to evaluate the compatibility of iron compounds and enhancers. Additionally, compatibility can be evaluated by determining the ability of an iron compound and an enhancer to form mixed micelles.

In certain embodiments of the invention, iron compound is the only active agent in the composition. In other embodiments, the composition comprises additional active agents. In one example, the additional active agents are useful for treating iron deficiency or disorders associated with iron deficiency. In other examples, the additional active agents are agents that are beneficially administered with iron, e.g., erythropoiesis-stimulating agents such as erythropoietin, epoetin alfa (PROCRIT/EPOGEN), epoetin beta (NEORECORMON), darbepoetin alfa (ARANESP), and methoxy polyethylene glycol-epoetin beta (MIRCERA). In other examples, the additional active agents are nutrients (e.g., vitamins and/or minerals) that provide the daily recommended amounts of nutrients and/or disorder treatment and/or prevention effective amounts. In some embodiments, the additional active agent is selected from the group consisting of folic acid, vitamin A, vitamin B (all series, including B1, B2, B3, B5, B6, B9, B12), vitamin C, vitamin D, vitamin E, calcium, chromium, copper, magnesium, manganese, potassium, selenium, zinc, phosphorus, iodine, biotin. inositol, para-amino benzoic acid, choline, and any combination thereof. As used herein, the term "vitamin B1" refers to thiamine. As used herein, the term "vitamin B2" refers to riboflavin. As used herein, the term "vitamin B3" refers to niacin and nicotinic acid. As used herein, the term "vitamin B5" refers to pantothenic acid. The term "vitamin B6" refers to pyridoxal, pyridoxamine and pyridoxine compounds. As used herein, the term "vitamin B9" refers to folic acid. The term "vitamin B12" refers to all forms of cobalamin including, without limitation, hydroxocobalamin, cyanocobalamin and methylcobalamin. The term "vitamin C" is used herein to refer to any form of vitamin C, including ascorbate and L-threonate. The term "vitamin D" is used to refer to both cholecalciferol (vitamin D3) and ergocalciferol (vitamin D2). The term "vitamin E" is used herein to refer to alpha-tocopherol, d-alpha-tocopherol, d-alpha-tocopheryl succinate (or acetate), dl-alpha-tocopherol, dl-alpha-tocopheryl acetate (or succinate), gamma tocopherol, mixed tocopherols, and dl-alpha tocopherol nicotinate. The term "calcium" is used herein to refer to any form of calcium including calcium carbonate, phosphate, lactate, gluconate, citrate and combinations thereof. The term "magnesium" is used herein to refer to any form of magnesium, including magnesium oxide, magnesium chloride, magnesium lactate, magnesium sulfate and magnesium gluconate.

In some embodiments, the enhancer is a medium chain fatty acid salt which has a carbon chain length of from about 4 to about 20 carbon atoms, e.g., from 6 to 20 carbon atoms, e.g., from 8 to 14 carbon atoms. In some embodiments, the enhancer is solid at room temperature. In certain embodiments, the medium chain fatty acid salt is the only absorption enhancer in the oral dosage form. In additional embodiments, the pharmaceutical composition comprises more than one medium chain fatty acid salt, e.g., 2, 3, 4, or more medium chain fatty acid salts. In other embodiments, the enhancer is a sodium salt of a medium chain fatty acid. In some embodiments, the enhancer is selected from the group consisting of sodium caprylate, sodium caprate and sodium laurate. Exemplary enhancers are further described in U.S. Pat. Nos. 7,658,938 and 7,670,626 and U.S. Published Application Nos. 2003/0091623 and 2007/0238707, which are incorporated by reference in their entirety. In some embodiments, the absorption enhancer is present in a ratio of from 1:100,000 to 10:1 (iron:enhancer).

One aspect of the invention relates to a solid oral dosage form comprising, consisting essentially of, or consisting of the pharmaceutical composition of the invention. The dosage form can comprise an amount of iron that is treatment effective (e.g., for treatment of iron deficiency and/or a disease or disorder characterized by iron deficiency) or prevention effective (e.g., to provide the daily recommended requirement of iron and/or prevent the onset of disease or disorders characterized by iron deficiency). In one embodiment, the solid oral dosage form comprises about 1 mg to about 200 mg iron, e.g., about 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200 mg or more of iron or any range therein. The amount of iron in the composition refers to the weight of the elemental iron, not the iron compound, present in the composition.

In certain embodiments, the dosage form is a solid oral dosage form (e.g., a tablet, capsule, multiparticulate, or powder dosage form) or a liquid oral dosage form (e.g., a solution, suspension, emulsion, syrup, or elixir). In some embodiments, the dosage form is a delayed release or controlled release dosage form. For example, the dosage form can be a tablet or other form comprising a rate controlling polymer material, e.g., hydroxypropyl methylcellulose, a polymer of acrylic or methacrylic acid or their respective esters, or copolymers of acrylic or methacrylic acid or their respective esters.

In some embodiments, the iron compound, absorption enhancer, and at least one auxiliary excipient are compressed into tablet form prior to coating with a rate controlling polymer. In some embodiments, the iron compound, absorption enhancer, and at least one auxiliary excipient are compressed into tablet form prior to coating with a delayed release polymer. In some embodiments, the iron compound, absorption enhancer, rate controlling polymer, and at least one auxiliary excipient are compressed to form a controlled release matrix tablet. In some embodiments, the controlled release matrix tablet is coated with a rate-controlling polymer. In some embodiments, the controlled release matrix is coated with a delayed release polymer. In some embodiments, the iron compound, absorption enhancer, and at least one auxiliary excipient are compressed into the form of a multilayer tablet prior to coating with a rate controlling-polymer. In some embodiments, the iron compound, absorption enhancer, and at least one auxiliary excipient are compressed into the form of a multilayer tablet prior to coating with a delayed release polymer. Yet, in another embodiment, the iron compound and absorption enhancer are dispersed in the rate-controlling polymer material and compressed into the form of a multilayer tablet. In some embodiments, the multilayer tablet is coated with a rate-controlling polymer. In some embodiments, the multilayer tablet is coated with a delayed release polymer.

In certain embodiments, the iron compound, absorption enhancer, at least one auxiliary excipient, and the rate-controlling polymer material are combined into a multiparticulate form. In some embodiments, the multiparticulate form comprises discrete particles, pellets, minitablets, or combinations thereof. In some embodiments, the dosage form of the present invention comprises a blend of two or more populations of particles, pellets or mini-tablets having different in vitro or in vivo release characteristics. In some embodiments, the multiparticulate is encapsulated in capsules, e.g., hard or soft gelatin capsules. In another embodiment, the capsule is coated with a rate-controlling polymer. In some embodiments, the capsule is coated with a delayed release polymer. In some embodiments, the multiparticulate is incorporated into a sachet.

In some embodiments, the discrete particles or pellets are compressed into tablet form. In some embodiments, the tablet form is coated with a rate controlling polymer material. Yet, in another embodiment, the tablet form is coated with a delayed release polymer. In some embodiments, the discrete particles or pellets are compressed into a multilayer tablet. In some embodiments, the multilayer tablet is coated with a rate controlling material. In some embodiments, the multilayer tablet is coated with a delayed release polymer.

In any of the above-mentioned embodiments, a controlled release coating (e.g., an enteric coating) may be applied to the final dosage form (capsule, tablet, multilayer tablet, etc.). The controlled release coating may typically comprise a rate controlling polymer material as defined above. The dissolution characteristics of such a coating material may be pH dependent or independent of pH.

The pharmaceutical compositions and oral dosage forms of the invention can comprise one or more auxiliary excipients, such as for example rate-controlling polymeric materials, solubilizers, diluents, lubricants, disintegrants, plasticizers, anti-tack agents, opacifying agents, glidants, pigments, flavorings, and the like. As will be appreciated by those skilled in the art, the exact choice of excipients and their relative amounts will depend to some extent on the final dosage form.

One excipient that can be included in the composition is one or more saccharides. Any suitable saccharide may be used in the composition of the present invention. As used herein, the "saccharides" used in the invention include, without limitation, sugar alcohols, monosaccharides, disaccharides, and oligosaccharides. Exemplary sugar alcohols include, but are not limited to, xylitol, mannitol, sorbitol, erythritol, lactitol, pentitol, and hexitol. Exemplary monosaccharides include, but are not limited to, glucose, fructose, aldose and ketose. Exemplary disaccharides include, but are not limited to, sucrose, isomalt, lactose, trehalose, and maltose. Exemplary oligosaccharides include, but are not limited to, fructo-oligosaccharides, inulin, galacto-ologosaccharides, and mannan-oligosaccharides. In some embodiments, the saccharide is sorbitol, mannitol, or xylitol. In some embodiments, the saccharide is sorbitol. In some embodiments, the saccharide is sucrose.

Any suitable amounts of saccharide may be added in the compositions of the present invention. In some embodiments of the present invention, the ratio of the enhancer and saccharide may be adjusted to achieve a desired dissolution rate and/or compressibility of the resulting pharmaceutical composition. In some embodiments, the ratio of the enhancer and saccharide is 2:1 to 20:1. According to some embodiments, the ratio of the enhancer and saccharide is about 4:1 to 6:1. In another embodiment, the ratio of the enhancer and saccharide is about 5:1.

Any suitable grade of saccharide may be used in the composition of the present invention. However, in some embodiments, the selection of the grade of saccharide may be dependent upon the particle size distribution (PSD) of a specific grade of saccharide. Further, in another embodiment, the specific grade of the saccharide may affect the characteristics of the resulting pharmaceutical composition such as dissolution rate and/or compressibility. In some embodiments, the selection of the grade of saccharide is dependent upon the PSD of other excipients and the therapeutically active ingredient. In some embodiments, the saccharide is Parteck SI 150 (Merck KGaA, Darmstadt, Germany), a directly compressible sorbitol. In other embodiments, the saccharide is Parteck SI 400 (Merck KGaA, Darmstadt, Germany).

Suitable diluents include, for example, pharmaceutically acceptable inert fillers such as microcrystalline cellulose, lactose, dibasic calcium phosphate, saccharides, and/or mixtures of any of the foregoing. Examples of diluents include microcrystalline cellulose such as that sold under the Trademark Avicel (FMC Corp., Philadelphia, Pa.), for example, Avicel™ pH101, Avicel™ pH102 and Avicel™ pH112; lactose such as lactose monohydrate, lactose anhydrous and Pharmatose DCL21; dibasic calcium phosphate such as Emcompress; mannitol; starch; sorbitol; sucrose; glucose; and combinations and mixtures thereof.

Suitable lubricants, including agents that act on the flowability of the powder to be compressed are, for example, colloidal silicon dioxide such as Aerosil™ 200; talc; stearic acid; magnesium stearate; calcium stearate; and combinations and mixtures thereof.

Suitable disintegrants include, for example, lightly crosslinked polyvinyl pyrrolidone, corn starch, potato starch, maize starch and modified starches, croscarmellose sodium, crospovidone, sodium starch glycolate, and combinations and mixtures thereof.

The term "rate controlling polymer material" as used herein includes hydrophilic polymers, hydrophobic polymers and mixtures of hydrophilic and/or hydrophobic polymers that are capable of controlling or retarding the release of the peptide or protein from a solid oral dosage form of the present invention. Suitable rate controlling polymer materials include those selected from the group consisting of hydroxyalkyl cellulose such as hydroxypropyl cellulose and hydroxypropyl methyl cellulose; poly(ethylene) oxide; alkyl cellulose such as ethyl cellulose and methyl cellulose; carboxymethyl cellulose; hydrophilic cellulose derivatives; polyethylene glycol; polyvinylpyrrolidone; cellulose acetate; cellulose acetate butyrate; cellulose acetate phthalate; cellulose acetate trimellitate; polyvinyl acetate phthalate; hydroxypropylmethyl cellulose phthalate; hydroxypropylmethyl cellulose acetate succinate; polyvinyl acetaldiethylamino acetate; poly (alkylmethacrylate) and poly(vinyl acetate). Other suitable hydrophobic polymers include polymers and/or copolymers derived from acrylic or methacrylic acid and their respective esters, zein, waxes, shellac and hydrogenated vegetable oils. Particularly useful in the practice of the present invention are poly acrylic acid, poly acrylate, poly methacrylic acid and poly methacrylate polymers such as those sold under the Eudragit tradename (Rohm GmbH, Darmstadt, Germany) specifically Eudragit® L, Eudragit® S, Eudragit® RL, and Eudragit® RS coating materials and mixtures thereof. Some of these polymers can be used as delayed release polymers to control the site where the drug is released. They include poly methacrylate polymers such as those sold under the Eudragit tradename (Rohm GmbH, Darmstadt, Germany) specifically Eudragit® L, Eudragit® S, Eudragit® RL, and Eudragit® RS coating materials and mixtures thereof.

The pharmaceutical composition can further comprise a solubilizer as an excipient. The term "solubilizer," as used herein, refers to any compound that improves the solubility of iron compounds in vitro, and includes organic chelation agents such as, without limitation, citric acid or salts thereof, ascorbic acid and salts thereof, EDTA, or any combination thereof. In one embodiment, the solubilizer is citric acid and/or sodium citrate. The solubilizer can be present in the pharmaceutical composition in an amount sufficient to increase the solubility of the iron compound and/or the absorption enhancer. In some embodiments, the solubilizer is present in an amount of about 2% to about 25% by weight, e.g., about 5% to about 20%, e.g., about 2, 3, 4, 5, 6, 7, 8, 9, 10, 11, 12, 13, 14, 15, 16, 17, 18, 19, 20, 21, 22, 23, 24, or 25%.

Without being limited to a specific mechanism, it is believed that the presence of a solubilizer improves the dissolution rate of both the iron compound and the enhancer in the compositions of the invention. However, as the ratio of solubilizer to iron compound increases past a certain point, the dissolution rate of the iron compound and the enhancer start to diverge such that the desired co-dissolution of the iron compound and the enhancer is no longer present. This is due to the continued increase in dissolution rate of iron compound as the ratio increases while the dissolution rate of the enhancer states to slow down and then decrease as the ratio increase. The ideal ratio will be different for each iron compound and solubilizer. The differential effect of solubilizer on the dissolution rates of the iron compound and the enhancer is surprising and unexpected. Thus, in certain embodiments, solubilizer is present in the pharmaceutical compositions of the invention in an amount sufficient to improve the dissolution rate of both the iron compound and the enhancer yet still maintain a substantially similar release of the iron compound and the enhancer.

As used herein, the term "substantially similar release" is defined as a ratio of the time for a percentage of the iron compound to be released from a dosage form without coating to the time for the same percentage of the enhancer to be released in the range of about 2.0 to about 0.5, e.g., about 1.3 to about 0.7, e.g., about 1.1 to about 0.9. In other embodiments, the term "substantially similar release" is defined as a ratio of the time for a percentage of the iron compound to be released from a dosage form with a coating (e.g., an enteric coating or other type of delayed release or sustained release coating) to the time for the same percentage of the enhancer to be released in the range of about 1.3 to about 0.7. To be considered substantially similar, the ratio must fall within the range at least two different time points, e.g., at least 3, 4, or 5 different time points. In one embodiment, the dissolution is carried out in 900 mL pH 6.8 phosphate buffer at 37° C. with a USP Paddle Apparatus at 50 rpm. In one embodiment, the dissolution assay includes a preliminary step of acid treatment (e.g., 2 hrs in 0.1 N HCl). For example, if the iron compound has a dissolution of 80% in about 20 minutes, sodium caprate (enhancer) must have a dissolution of 80% in the range of about 14 minutes to 26 minutes to be substantially similar. In one embodiment, the ratio is in the range of about 1.1 to about 0.9. For example, if the iron compound has a dissolution of 80% in about 20 minutes, sodium caprate (enhancer) must have a dissolution of 80% in the range of about 18 minutes to about 22 minutes.

In some embodiments, the solubilizer is present in the pharmaceutical composition in an amount sufficient to increase the dissolution rate of at least one of the iron compound and the enhancer by at least about 5%, e.g., at least about 10%, 15%, 20%, or more. In other embodiments, the solubilizer is present in the pharmaceutical composition in an amount such that the iron compound and the enhancer have a substantially similar release. In certain embodiments, the solubilizer is present in the pharmaceutical composition in an amount sufficient to enhance the dissolution rate such that both the iron compound and the enhancer achieve at least about 80% dissolution in 3 hours, e.g., at least about 80% dissolution in 2.5, 2, 1.5, or 1 hour.

The pharmaceutical compositions and oral dosage forms of the invention can comprise liquid oral dosage forms (solutions, syrups, suspensions, elixirs, emulsions, etc.) or powder oral dosage forms (either for reconstitution or ingestion). As will be appreciated by those skilled in the art, the exact choice of excipients and their relative amounts will depend to some extent on the final dosage form.

It is well known that iron absorption occurs predominantly via active transport in the duodenum and upper jejunum. A feedback mechanism exists that increases iron absorption in subjects that are iron deficient. In subjects with iron overload, this feedback mechanism dampens iron absorption.

Figure 21:
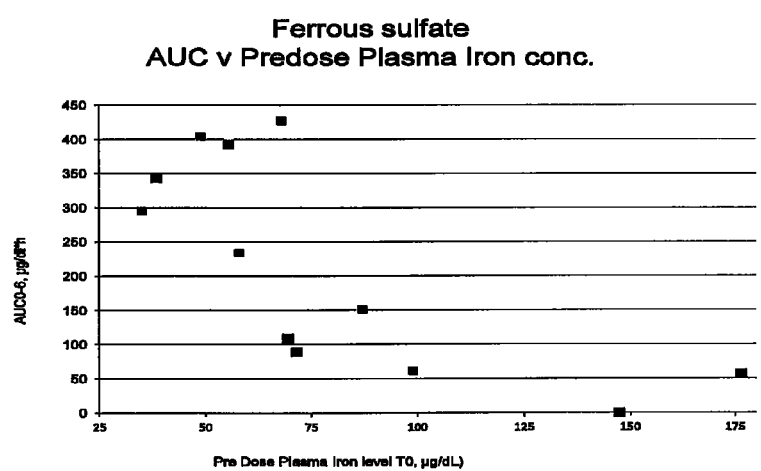
FIG. 21 shows a plot of AUC vs. predose plasma iron concentration for ferrous sulfate.

Data collected in Example 12 were evaluated to determine the relationship between iron absorption and the iron levels at baseline for each of the study periods. It was found in this analysis that the amount of iron absorbed from the unenhanced formulation decreased as the iron levels at baseline increased. FIG. 21 demonstrates this relationship. The unenhanced AUCs vs. predose iron levels displays a clear relationship between predose iron levels and absorbed iron. Animals with higher predose iron levels absorbed less iron from the unenhanced test formulation. This fits with the theory that iron is absorbed by active transport and there is a feedback mechanism.

Figure 22:
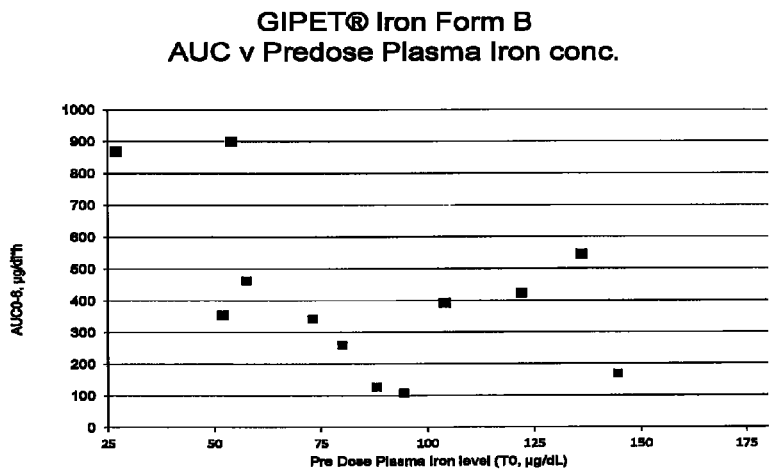
FIG. 22 shows a plot of AUC vs. predose plasma iron concentration for iron Form B.

In contrast, for the enhanced formulation, this decrease in absorption with increased baseline iron levels was not similarly seen. In fact, the dog with the third highest baseline level was the second highest absorbing subject. FIG. 22, the plot of enhanced iron AUCs vs. predose iron levels, demonstrates this. This is likely a result of paracellular and transcellular absorption of iron promoted by the enhanced formulation caused by the formation of mixed micelles of the iron and the enhancer system. Hence, while absorption of iron by active transport is suppressed when predose iron levels rise, absorption by paracellular and transcellular absorption promoted by enhancers of the invention is not affected by negative feedback. Without being limited to a specific mechanism, it may be that the ability of the compositions of the invention to overcome the negative feedback mechanism for iron absorption is at least in part responsible for the enhanced bioavailability of iron.

One aspect of the present invention relates to a method of orally delivering elemental iron contained in an iron compound to a subject, comprising administering to the subject the oral dosage form of the invention. Another aspect of the present invention relates to a method for increasing the level of iron in a subject, e.g., in the blood and/or stored as ferritin in bone marrow, liver, and/or spleen, comprising administering to the subject the oral dosage form of the invention. Another aspect of the present invention relates to a method for increasing the level of hemoglobin in the blood of a subject, comprising administering to the subject the oral dosage form of the invention. The subject can be a subject in need thereof, e.g., a subject having an iron deficiency, a subject at risk of an iron deficiency, or a subject that desires to maintain normal blood and/or tissue levels of iron. In some embodiments, the methods of the invention can increase the level of iron in the blood by at least about 5 µg/dl, e.g., at least about 10, 20, 30, 40, 50, 60, 70, 80, 90, or 100 µg/dl or more. In some embodiments, the methods of the invention can increase the level of hemoglobin in the blood by at least about 0.5 g/dl, e.g., at least about 1, 2, 3, 4, or 5 g/dl or more. Methods for measuring the level of iron and hemoglobin in the blood are well known in the art.

One aspect of the present invention relates to a method for treating or preventing an iron deficiency in a subject in need thereof, comprising administering to the subject the oral dosage form of the invention. Another aspect of the present invention relates to a method for treating or preventing a disease or disorder characterized by an iron deficiency in a subject in need thereof, comprising administering to the subject the oral dosage form of the invention.

In certain embodiments, the method treats or prevents various anemic states. In some embodiments, the anemia is an iron deficiency anemia, such as that associated with chronic blood loss, acute blood loss, pregnancy, childbirth, childhood development, psychomotor and cognitive development in children, breath holding spells, heavy uterine bleeding, menstruation, chronic recurrent hemoptysis, idiopathic pulmonary siderosis, chronic internal bleeding, gastrointestinal bleeding, parasitic infections, chronic kidney disease, dialysis, surgery or acute trauma, and chronic ingestion of alcohol, chronic ingestion of salicylates, chronic ingestion of steroids, chronic ingestion of non-steroidal anti-inflammatory agents, or chronic ingestion of erythropoiesis stimulating agents. In some aspects, the anemia is anemia of chronic disease, such as rheumatoid arthritis, cancer, Hodgkin's lymphoma, non-Hodgkin's lymphoma, cancer chemotherapy, inflammatory bowel disease, ulcerative colitis, thyroiditis, hepatitis, systemic lupus erythematosus, polymyalgia rheumatica, scleroderma, mixed connective tissue disease, Sjögren's syndrome, congestive heart failure/cardiomyopathy, or idiopathic geriatric anemia. In some embodiments, the anemia is due to impaired iron absorption or poor nutrition, such as anemia associated with Crohn's disease, gastric surgery, ingestion of drug products that inhibit iron absorption, and chronic use of calcium. In some embodiments, the disorder is a functional iron deficiency as can occur where there is a failure to release iron rapidly enough to keep pace with the demands of the bone marrow for erythropoiesis (e.g., subjects on erythropoietin therapy). In other embodiments, the method treats restless leg syndrome, blood donation, Parkinson's disease, hair loss, or attention deficit disorder.

Identification of subjects in need of treatment can be carried out by methods known to those of skill in the art. For example, need can be assessed by monitoring a subject's iron status. The diagnosis of iron deficiency can be based on appropriate laboratory tests, for example, hemoglobin (Hb), serum ferritin, serum iron, transferrin saturation (TfS), and hypochromic red cells. Additional techniques for measuring iron levels are disclosed in U.S. Pat. Nos. 7,659,074, 7,609, 369, 7,601,684, 7,412,275, 7,361,512, and 7,361,510, each herein incorporated by reference in its entirety.

In another aspect, the invention relates to a method for maintaining iron indices in a subject to ensure maximum efficacy of erythropoietin and/or other erythropoiesis-stimulating agents (ESA), comprising administering to the subject the oral dosage form of the invention. The subject may be one that is currently being administered ESA or will be administered ESA. In some embodiments, the oral dosage form of the invention is administered to the subject before, during, and/or after the administration of ESA. The oral dosage form may be administered in an amount to prevent a decrease in blood levels of iron during ESA administration and/or to increase blood levels of iron to the level that existed in the subject prior to administration of ESA.

In one embodiment of the invention, the oral dosage form of the invention is administered to the subject as needed to raise serum iron levels and/or treat and/or prevent a disorder. The dosage form can be administered continuously or intermittently. In one embodiment, the dosage form is administered to the subject more than once a day, e.g., 2, 3, 4, or more times a day or once every 1, 2, 3, 4, 5, 6, or 7 days. In another embodiment, the dosage form is administered to the subject no more than once a week, e.g., no more than once every two weeks, once a month, once every two months, once every three months, once every four months, once every five months, once every six months, or longer. In a further embodiment, the dosage form is administered using two or more different schedules, e.g., more frequently initially (for example to build up to a certain level, e.g., once a day or more) and then less frequently (e.g., once a week or less). In other embodiments, the dosage form can be administered by any discontinuous administration regimen. In one example, the dosage form can be administered not more than once every two days, every three days, every four days, every five days, every six days, every seven days, every eight days, every nine days, or every ten days, or longer. The administration can continue for one, two, three, or four weeks or one, two, or three months, or longer. Optionally, after a period of rest, the dosage form can be administered under the same or a different schedule. The period of rest can be one, two, three, or four weeks, or longer, according to the pharmacodynamic effects of the dosage form on the subject.

The oral dosage form is delivered to the subject at a dose that is effective to raise serum iron levels, raise Hb levels, and/or treat and/or prevent a disorder. The effective dosage will depend on many factors including the gender, age, weight, and general physical condition of the subject, the severity of the disorder, the particular composition being administered, the duration of the treatment, the nature of any concurrent treatment, the carrier used, and like factors within the knowledge and expertise of those skilled in the art. As appropriate, a treatment effective amount in any individual case can be determined by one of skill in the art by reference to the pertinent texts and literature and/or by using routine experimentation (see, e.g., Remington, *The Science and Practice of Pharmacy* (21$^{st}$ ed. 2005)). In one embodiment, the dosage form is administered at a dose of about 1 to about 200 mg iron, e.g., about 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200 mg or more of iron. In some instances, the dose can be even lower, e.g., as low as 0.001 or 0.1 mg or lower. In some instances, the dose can be even higher, e.g., as high as 500 or 1000 mg or higher. The present invention encompasses every sub-range within the cited ranges and amounts.

Another aspect of the present invention provides a process for manufacturing a solid oral dosage form of a pharmaceutical composition comprising the steps of: a) blending iron with an absorption enhancer, and optionally auxiliary excipients to form a blend; wherein the enhancer is a medium chain fatty acid salt having a carbon chain length of from about 4 to about 20 carbon atoms; and b) forming a solid oral dosage from the blend by i) directly compressing the blend to form the solid oral dosage form, or ii) granulating the blend to form a granulate for incorporation into the solid oral dosage form, or iii) spray drying the blend to form a multiparticulate for incorporation into the solid oral dosage form. In some embodiments, the iron and the enhancer are blended in a ratio of from 1:100,000 to 10:1 (iron:enhancer).

The present invention will now be described in more detail with reference to the following examples. However, these examples are given for the purpose of illustration and are not to be construed as limiting the scope of the invention.

In the examples, it can be seen that formulations of the present invention can achieve a bioavailability increase for sodium iron EDTA and soluble iron pyrophosphate of more than five-fold over unenhanced formulations.

Example 1

Pharmacokinetic Studies of Sodium Iron EDTA Complex

Pre-formulation experiments indicated no gross incompatibility between the proposed sodium caprate formulation (55 mg/mL) and the sodium EDTA iron chelate (Table 1). Visual observation for two weeks at ambient temperature indicated good solution stability for all formulations, except sample 5 and 6 (5.43 and 8.14 mg elemental iron), where some precipitation was noticed. The data also indicated that this iron compound is amenable to an enhanced iron formulation with an acceptable dose solubility of elemental iron concentration required for clinical use. In-house analytical methods were not carried out to assay iron content but the development was based on label claim elemental iron content. The final formulations dosed in dogs were assayed for iron content carried out by a contract laboratory.

TABLE 1

Solution stability of sodium EDTA $Fe^{+3}$ chelate with sodium caprate

| Sample | Concentration mg/mL | | |
|---|---|---|---|
| No | Sodium caprate | EDTA Salt | Elemental Iron |
| 1 | 55 | 3.26 | 0.47 |
| 2 | 55 | 6.50 | 0.93 |
| 3 | 55 | 9.77 | 1.40 |
| 4 | 55 | 19.00 | 2.71 |
| 5 | 55 | 38.00 | 5.43 |
| 6 | 55 | 57.00 | 8.14 |

Based on the above results, the following formulations of iron complex, ethylenediaminetetraacetic acid ferric sodium (or an EDTA chelate) were prepared prior to in vivo dosing. Iron concentration was based on label claim of elemental iron (Product No E6760, batch No. 019K01541) and was assumed to be pure. The test items were stored in glass containers. The formulations were shipped at ambient temperature to contract analytical centre for the assay of iron content.

1. Control unenhanced formulation: Aqueous formulation of iron complex alone (0.783 mg/mL elemental iron) in de-ionized water.
2. Enhanced iron test formulation A: Aqueous formulation of iron complex (0.783 mg/mL elemental iron) in 55 mg/mL sodium caprate aqueous solution.

A two-way crossover pre-clinical study was carried out in an iron deficient model of beagle dogs. Eight adult female non-naïve intra-duodenally (ID) cannulated beagle dogs (5.3-7.2 kg) of 23-40 months were divided into two groups (Group A and B) of four animals each (n=4). An iron deficient state was induced by phlebotomy, where a plasma iron drop≥25% and 20% drop in hematocrit were deemed to be adequate. For the purpose of dose administration, the dogs used in this study were surgically implanted with vascular access ports (VAPs). Each VAP is connected to a cannula which is inserted into the duodenum. The liquid test formulations were administered to all subjects intra-duodenally through the VAP (at a dose of 7.83 mg elemental iron/animal) in two phases with a wash-out period in between (Table 2). Blood samples were withdrawn at scheduled intervals to estimate plasma iron levels and were used to calculate PK parameters. Body weights were recorded prior to each dosing and throughout the study. Prior to dose administration, dogs were fasted for at least 12 hours and food was returned ~4 hours post dosing. Data collected prior to the end of the fast was evaluated for demonstration of iron absorption, as the diet supplied contained additional iron. The 10 mL volume of test items 1 and 2 were administered through the VAPs connected to a cannula into the duodenum. Following dose administration, the devices were flushed with 0.9% saline water to ensure that the entire test item was delivered into the duodenum. Blood was collected at scheduled intervals to estimate plasma drug levels.

TABLE 2

Experimental schedule of the test formulations, and dosing details

| Period No. | Animals Group(n = 4) | Day of Dose | Route | Formulation | Formulation Code | Dose (mg/dose*) |
|---|---|---|---|---|---|---|
| 1 | A | 8 | ID♦ (Solution) | TI1: control unenhanced | UC1 | 51.5 Iron Chelate |
| 1 | B | 8 | ID♦ (Solution) | TI2: enhanced formulation I | EF1 | 51.5 Iron Chelate 550 mg Sodium Caprate |
| 2 | A | 14 | ID♦ (Solution) | TI2: enhanced formulation I | EF1 | 51.5 Iron Chelate 550 mg Sodium Caprate |
| 2 | B | 14 | ID♦ (Solution) | TI1: control unenhanced | UC1 | 51.5 Iron Chelate |

♦ID = Intraduodenal, Each mL contains 5.15 mg Iron Chelate (0.783 mg elemental iron) and 550 mg Sodium Caprate (TI2).

On the days of dosing, each dog was housed individually for observation and was returned to group housing after the 24 hour blood collection time point of each period involving administration of respective test item. Teklad 21% Lab Dog Diet (W) 8755 was fed once per day and tap water was provided ad libitum except as indicated during dosing. Environmental controls were set to maintain temperatures from 18-29° C. and humidity from 30-70%. Light source was fluorescent lighting on a 12 hr/12 hr on/off cycle except as required for specimen collection.

Prior to study initiation, each dog was confirmed to be healthy. Dogs were observed at least once daily 7 days prior to dosing and for the duration of the study. The clinical observations were recorded once daily and any other times when a clinically significant change was noted. In-life phase assessments included but were not limited to assessment of activity, posture, respiration, hydration status, and overall body condition. Animals were returned to stock following the end of the live period portion of this study.

Blood (~1.5 ml) was collected, via cephalic or jugular vein, into heparinized blood collection tubes at pre-dose (T0), 1, 2, 4, 6, 8, 10, 12, 14, 16, 20, 24 and 48 hours following dose administration. Care was taken to avoid hemolysis during the blood collection procedure. The blood was kept on ice for a maximum of 20 minutes until centrifuged. The centrifugation procedure was carried out at 4° C. and 3000 rpm for 10 minutes. Immediately after centrifugation, all plasma was transferred to appropriate labeled vials, frozen (at −70° C.) and was shipped to the bio-analytical centre for the assay of total plasma iron content.

At the bio-analytical centre, plasma samples were assayed using a method for plasma iron content (Roche Diagnostics for the Hitachi 917 chemistry analyzer). Any remaining plasma was disposed of by incineration at the test facility, following the issuing of the final report for this study.

Upon receipt of bio-analytical data, the individual animal plasma concentration vs. time data was loaded into an Excel spread sheet (Microsoft® office 2007). The PK parameters including $AUC_{0-t}$, maximum plasma concentrations ($C_{max}$) and time to achieve $C_{ma}$, ($T_{max}$) were calculated using macros written for MS Excel by Usansky et al. The above plasma data were used to calculate mean PK parameters, standard deviations, and SE (mean Standard errors). The relative bioavailability was expressed as fold increase relative to the unenhanced formulation. Data were evaluated as reported, and with a baseline correction, where the value of the 0-hour sample for each dog in each period was subtracted from the subsequent levels for that dog during that period. Statistical significance between groups was analyzed using a two tail student T test assuming equal variance. The data is expressed as mean±SD or mean±SE. Only data collected during the fasting period were used in the analysis of absorption, as the diet fed to the dogs included iron.

The live phase portion of this study was 16 days in duration, which includes the induction of an iron deficiency state utilizing a phlebotomy procedure and crossover dosing of two test items in two phases with a washout period of six days. The dogs were made iron deficient by collecting an estimated 20% of the dog's blood volume from the jugular vein on days 0, 1, 2 for all dogs and 10% volume on Day 4 from dogs 4, 6, 7 and 8. The iron deficient state was deemed to be adequate when the mean hematocrit, or packed cell volume (PCV) was reduced to ≥20% of initial and the target mean plasma iron was reduced to ≤25% of normal range noticed during prephlebotomy. Although mean hematocrit reached required levels on day 2 itself, plasma iron levels were higher on day 2 compared to pre-phlebotomy levels (day 0). Refer to Tables 3 and 4 for plasma iron and hematocrit values during first and second period dosing.

First period dosing was carried out in respective groups (Table 2) on day 8 followed by the scheduled blood collection time points. Based on plasma iron content, it was decided that no phlebotomy was required prior to period 2 dosing, which was carried out after a six day wash out period after the first period of dosing.

TABLE 3

Plasma iron and hematocrit levels before period1 dosing of test items

| Group | No Animal ID | Induction phase % Hematocrit (plasma Iron (µg/dL)) | | | | | | Phase1 | % reduction prior to phase1 | |
|---|---|---|---|---|---|---|---|---|---|---|
| | | Day 0 07dec | Day 1 08dec | Day 2 9dec | Day 3 10dec | Day 4 11dec | Day 7 14dec | Day 8 15dec | PCV % Day 8 | Plasma iron Day 8 |
| A | 1 (1135491) | 51 (129) | 40 | 38 (169) | 27 (62) | 32 (93) | 35 (118) | 31 (87) | 39 | 33 |
| | 2 (1142837) | 52 (117) | 43 | 39 (143) | 30 (55) | 33 (65) | 37 (113) | 34 (60) | 35 | 49 |
| | 3 (1144694)) | 50 (134) | 39 | 35 (188) | 26 (203) | 32 (186) | 35 (99) | 30 (68) | 40 | 49 |
| | 4 (1146522) | 52 (109) | 45 | 36 (114) | 25 (78) | 28 (137) | 32 (151) | 30 (78) | 42 | 28 |
| B | 5 (1138520) | 49 (161) | 40 | 35 (127) | 28 (61) | 30 (71) | 35 (113) | 31 (66) | 37 | 59 |
| | 6 (1141482) | 49 (177) | 37 | 32 (283) | 28 (264) | 29 (208) | 32 (160) | 32 (132) | 35 | 25 |
| | 7 (1144546) | 50 (115) | 39 | 33 (210) | 26 (224) | 29 (139) | 34 (300) | 30 (66) | 40 | 43 |
| | 8 (1145526) | 46 (141) | 31 | 37 (181) | 25 (90) | 28 (109) | 32 (93) | 31 (108) | 33 | 23 |

Plasma iron protocol range = 145-153 ug/dL, Target = −25%,
* mean reductions Group A 40% ± 11, Group B 38% ± 17, Hematocrit -Normal = 40-55%, Group A 39% ± 3, Group B 36% ± 3

TABLE 4

Plasma iron and hematocrit levels before period 2 dosing of test items

| Group | Animal ID | Induction phase % Hematocrit (plasma Iron µg/dL) | | | Phase2 T0 | % reduction prior to phase2* | |
|---|---|---|---|---|---|---|---|
| | | Day 0 07dec | Day 8 15dec | Day 11 18dec | Day 14 21dec | Hematocrit Day 14* | Plasma iron Day 14 |
| A | 1 (1135491) | 51 (129) | 31 (87) | 36 | 41 (93) | 20 | 28 |
| | 2 (1142837) | 52 (117) | 34 (60) | 38 | 39 (78) | 25 | 33 |
| | 3 (1144694)) | 50 (134) | 30 (68) | 34 | 42 (104) | 16 | 22 |
| | 4 (1146522) | 52 (109) | 30 (78) | 37 | 40 (73) | 23 | 33 |
| B | 5 (1138520) | 49 (161) | 31 (66) | 35 | 40 (120) | 18 | 26 |
| | 6 (1141482) | 49 (177) | 32 (132) | 37 | 39 (118) | 20 | 33 |
| | 7 (1144546) | 50 (115) | 30 (66) | 38 | 36 (75) | 28 | 35 |
| | 8 (1145526) | 46 (141) | 31 (108) | 35 | 37 (74) | 20 | 48 |

Plasma iron, Target = −25%,
*mean reductions Group A 29% ± 5, Group B 35% ± 9; Hematocrit - Normal = 40-55%, Group A 21% ± 4, Group B 22% ± 4

In a two-way crossover design, the relative oral absorption of enhanced iron formulation A was compared with an unenhanced control formulation. In each phase, both liquid formulations were administered to each group of four dogs (n=4) in two phases at an elemental iron dose of 7.83 mg/subject (Table 2).

Total plasma iron concentrations after oral administration of test formulations are shown in Table 5. The raw data for individual animals is shown in Table 6.

TABLE 5

Plasma iron concentrations of test formulations in periods 1 and period 2

| Time (hrs) | Group A | | | | Group B | | | | Mean |
|---|---|---|---|---|---|---|---|---|---|
| | 1135491 | 1142837 | 1144694 | 1146522 | 1138520 | 1141482 | 1144546 | 1145526 | |
| Enhanced formulation | | | | | | | | | |
| 0 | 0 | 0 | 0 | 0 | 0 | 0 | 0 | 0 | 0 |
| 1 | 36 | 115 | 11 | 22 | 21 | 73 | 48 | 29 | 44.375 |
| 2 | 49 | 169 | 14 | 29 | 29 | 123 | 71 | 37 | 65.125 |
| 4 | 42 | 128 | 15 | 30 | 44 | 164 | 79 | 35 | 67.125 |
| Control formulation | | | | | | | | | |
| 0 | 0 | 0 | 0 | 0 | 0 | 0 | 0 | 0 | 0 |
| 1 | 9 | 9 | 11 | 8 | 12 | 23 | 17 | 0 | 11.125 |
| 2 | 6 | 5 | 19 | 2 | 7 | 37 | 20 | 8 | 13 |
| 4 | 25 | 9 | 26 | 19 | 18 | 35 | 20 | 5 | 19.625 |

TABLE 6

Plasma iron concentrations of test formulations for individual animals

| Animal ID | Group | Baseline | pre-dose | % Change in Fe from baseline | 1 hr | 2 hr | 4 hr | 6 hr | 8 hr | 10 hr | 12 hr | 14 hr | 16 hr | 20 hr | 24 hr | 48 hr | % Change in Fe from Baseline |
|---|---|---|---|---|---|---|---|---|---|---|---|---|---|---|---|---|---|
| 1135491 | A | 129 | 87 | −32.56% | 96 | 93 | 112 | 169 | 218 | 280 | 319 | 403 | 402 | 262 | 158 | 86 | −33.33% |
| 1142837 | A | 117 | 60 | −48.72% | 69 | 65 | 69 | 100 | 134 | 147 | 179 | 286 | 325 | 320 | 110 | 57 | −51.28% |
| 1144694 | A | 134 | 68 | −49.25% | 79 | 87 | 94 | 145 | 196 | 278 | 362 | 347 | 337 | 113 | 46 | 59 | −55.97% |
| 1146522 | A | 109 | 78 | −28.44% | 86 | 80 | 97 | 142 | 184 | 202 | 226 | 268 | 314 | 211 | 79 | 71 | −34.86% |
| | Mean | 122.3 | 73.3 | −39.7% | 82.5 | 81.3 | 93.0 | 139.0 | 183.0 | 226.8 | 271.5 | 326.0 | 344.5 | 226.5 | 98.3 | 68.3 | −43.9% |
| | SD | 11.4 | 11.8 | 10.8% | 11.4 | 12.1 | 17.8 | 28.7 | 35.6 | 64.4 | 83.8 | 61.5 | 39.5 | 87.8 | 47.6 | 13.4 | 11.5% |
| 1138520 | B | 161 | 66 | −59.01% | 87 | 95 | 110 | 145 | 165 | 136 | 105 | 175 | 353 | 307 | 122 | 97 | −39.75% |
| 1141482 | B | 177 | 132 | −25.42% | 205 | 255 | 296 | 343 | 352 | 337 | 328 | 333 | 339 | 333 | 189 | 104 | −41.24% |
| 1144546 | B | 115 | 66 | −42.61% | 114 | 137 | 145 | 178 | 204 | 207 | 189 | 198 | 297 | 205 | 113 | 81 | −29.57% |
| 1145526 | B | 141 | 108 | −23.40% | 137 | 145 | 143 | 188 | 282 | 366 | 365 | 349 | 359 | 269 | 73 | 54 | −61.70% |

TABLE 6-continued

Plasma iron concentrations of test formulations for individual animals

|  |  |  |  |  |  |  |  |  |  |  |  |  |  |  |  |  |  |
|---|---|---|---|---|---|---|---|---|---|---|---|---|---|---|---|---|---|
| Mean | 148.5 | 93.0 | −37.6% | 135.8 | 158.0 | 173.5 | 213.5 | 250.8 | 261.5 | 246.8 | 263.8 | 337.0 | 278.5 | 124.3 | 84.0 | −43.1% |
| SD | 26.8 | 32.7 | 16.7% | 50.5 | 68.3 | 83.2 | 88.3 | 83.2 | 108.5 | 121.1 | 89.9 | 28.0 | 55.6 | 48.1 | 22.2 | 13.5% |

A = TI1: Control Unenhanced, B = TI2: Enhanced Formulation I

| Animal ID | Group | Base-line | pre-dose | % Change in Fe from baseline | 1 hr | 2 hr | 4 hr | 6 hr | 8 hr | 10 hr | 12 hr | 14 hr | 16 hr | 20 hr | 24 hr | 48 hr | % Change in Fe from Baseline |
|---|---|---|---|---|---|---|---|---|---|---|---|---|---|---|---|---|---|
| 1135491 | A | 129 | 93 | −27.91% | 129 | 142 | 135 | 159 | 198 | 221 | 283 | 439 | 405 | 274 | 164 | 95 | −26.36% |
| 1142837 | A | 117 | 78 | −33.33% | 193 | 247 | 206 | 188 | 194 | 202 | 220 | 249 | 348 | 333 | 173 | 62 | −47.01% |
| 1144694 | A | 134 | 104 | −22.39% | 115 | 118 | 119 | 144 | 174 | 178 | 210 | 309 | 358 | 292 | 158 | 41 | −69.40% |
| 1146522 | A | 109 | 73 | −33.03% | 95 | 102 | 103 | 126 | 151 | 167 | 199 | 285 | 315 | 263 | 90 | 75 | −31.19% |
|  | Mean | 122.3 | 87.0 | −29.2% | 133.0 | 152.3 | 140.8 | 154.3 | 179.3 | 192.0 | 228.0 | 320.5 | 356.5 | 290.5 | 146.3 | 68.3 | −43.5% |
|  | SD | 11.4 | 14.2 | 5.2% | 42.4 | 65.3 | 45.4 | 26.2 | 21.6 | 24.2 | 37.7 | 82.8 | 37.2 | 30.8 | 38.0 | 22.7 | 19.4% |
| 1138520 | B | 161 | 120 | −25.47% | 132 | 127 | 138 | 184 | 218 | 225 | 328 | 358 | 367 | 285 | 76 | 39 | −75.78% |
| 1141482 | B | 177 | 118 | −33.33% | 150 | 155 | 153 | 174 | 170 | 167 | 167 | 200 | 288 | 378 | 257 | 215 | 21.47% |
| 1144546 | B | 115 | 75 | −34.78% | 92 | 95 | 95 | 131 | 162 | 206 | 283 | 379 | 373 | 233 | 102 | 97 | −15.65% |
| 1145526 | B | 141 | 74 | −47.52% | 65 | 82 | 79 | 127 | 246 | 380 | 381 | 374 | 366 | 277 | 93 | 64 | −54.61% |
|  | Mean | 148.5 | 96.8 | −35.3% | 109.8 | 114.8 | 116.3 | 154.0 | 199.0 | 244.5 | 289.8 | 327.8 | 348.5 | 293.3 | 132.0 | 103.8 | −31.1% |
|  | SD | 26.8 | 25.7 | 9.1% | 38.4 | 32.8 | 34.9 | 29.2 | 39.9 | 93.5 | 91.1 | 85.6 | 40.5 | 61.0 | 84.0 | 77.9 | 43.0% |

A = TI2: Enhanced Formulation I, TI1: Control Unenhanced

Relative bioavailability was analysed using $AUC_{0-4\,hrs}$ significant improvement was noted with the enhanced iron formulation (FIG. 1).

The extent of absorption is 5.8 fold higher for the baseline corrected iron data set. Analysis of both phases of dosing (n=8, groups A and B), demonstrate that enhanced iron form A shows significant improvement (P<0.02) in the relative oral bioavailability (5.48-fold) of iron absorption (Table 7). Over all, the in vivo crossover analysis indicates a potential of enhanced iron form A to meet the objective(s) of oral bioavailability enhancement of iron.

TABLE 7

Summary of relative oral bioavailability of enhanced Iron A

| Group | Relative bioavailability 0-4 hrs | |
|---|---|---|
|  | Total Iron | Absorbed Iron |
| Overall (n = 8**) | 1.55 ± 0.24 (0.05) | 5.48 ± 2.09 (0.02) |

Conclusion

This study shows the relative performance of an enhanced iron formulation on the oral absorption of elemental iron compared to an unenhanced control. The enhanced iron formulation showed superior rate and extent of absorption compared with control formulation. As the animals were fed a standard meal containing iron after 4 hours, only these data were used to calculate relative bioavailability. The analysis demonstrates a significant improvement in the rate and extent oral absorption of iron (i.e., 5.5-fold higher relative bioavailability). Therefore, the absorption enhancement technology has a potential utility to replace (1) currently available parenteral formulations and (2) oral formulations to preclude associated GI side effects.

Example 2

Evaluation of Forms of Iron with Enhancer Systems

This study developed procedures for evaluation of existing and potential salts and chelates of iron for use in oral enhanced formulations. Iron compounds are screened for compatibility with sodium caprate (C10). Appropriate formulations with optimized dissolution profiles are developed. Based on the procedures developed, a representative iron formulation in solution was developed. This procedure can be used to screen other salts and chelates and to develop appropriate enhanced iron formulations.

Solubility and Compatibility (Pre-Formulation) Experiments

A test for precipitation was carried out. The solution formulations were centrifuged initially at 1000 rpm for 5 minutes. No precipitation was noted. They were further centrifuged at 5000 rpm for 5 minutes. No precipitation was noted. Hence this iron compound was considered compatible with C10. Refer to Table 8 for results.

Discussion

Aqueous solubility studies of ferric pyrophosphate soluble and ferric pyrophosphate were carried out up to 50 mg/mL in purified water. C10 compatibility was tested by dissolving incremental amounts of these iron compounds (up to 50 mg/ml) in 55 mg/mL sodium caprate.

Ferric pyrophosphate (CAS No 10058-44-3) is practically insoluble in water, and C10 did not change its aqueous solubility (Table 8). Ferric pyrophosphate soluble (CAS No 85338-24-5) is available as a complex mixture of ferric pyrophosphate (46%) and sodium citrate (54%), and hence has no specific molecular weight, however it is expected to be a low molecular weight compound (<1000 Daltons).

Ferric pyrophosphate soluble has good water solubility up to the tested range (50 mg/mL, green color solution). Up to the tested range (5 mg/mL), this compound has shown solution compatibility with C10 (55 mg/mL), which was a hazy yellowish orange solution. There was no precipitation demonstrated by centrifugation indicating that iron is dispersed/solubilized, and probably exists as a micelle solution.

TABLE 8

Pre-formulation with iron chelates

| Material | Material spec | | Observations | |
| --- | --- | --- | --- | --- |
| | Fe Spec | COA | Aqueous solubility | Sodium caprate solution compatibility |
| Ferric pyrophosphate soluble N 101578 | Min 11% | 11.32 | 50 mg/mL soluble, green color solution. | Light yellow solution at 5 mg/mL and 10 mg/ml in 55 mg/mL C10 At higher concentrations (up to 50 mg/mL), the solution was turbid yellow but not precipitated (centrifugation test) |
| Ferric pyrophosphate** | 10.5-12.5% | 11.1%# | Insoluble in water | Not soluble even in 55 mg/mL sodium caprate |

**Molecular weight 745.21 for $Fe_4(P_2O_7)_3$, discrepancy noted as the iron content needs to be above 20-30%.

Aqueous solubility studies of ferrous asparto glycinate and ferrous bis glycinate were carried out at 10-50 mg/mL in purified water. C10 compatibility was tested by dissolving incremental amounts of these iron compounds (up to 10 mg/ml) in 55 mg/mL C10. Refer to Table 9 for results.

Amino acid based iron chelates were found to be incompatible with C10 despite good aqueous solubility (Table 9). Since the iron compound contained in the Ferrochel® product (Albion; Ferrous/Ferric bisglycinate) was reported to be soluble in the acidic and alkaline environments, this compound was tested for solubility in purified water, phosphate buffer pH 6.8, and a solution of C10 (Table 10). Despite good aqueous solubility, Ferrochel® is deemed not suitable for enhancer development as this compound precipitates in the presence of C10. Ferrous gluconate also showed C10 incompatibility (refer to Table 10).

TABLE 9

Pre-formulation with Iron chelates (EXP-NB GIPET Iron 1-23*)

| Material | Observations | |
| --- | --- | --- |
| | Aqueous solubility | Sodium caprate solution compatibility |
| Ferrous Asparto glycinate | 10 mg/mL soluble, Light green solution | Solution turned black to grayish black colour, with severe precipitation Despite good aqueous solubility, It does not have compatibility with C10 |
| Ferrous bis glycinate | 50 mg/mL soluble, Clear solution | Also, precipitation noted at 5 mg/mL in 55 mg/mL C10, 50% dilution did not improve solubility. |

TABLE 10

Pre-formulation with iron compounds

| Material* | Observations | |
| --- | --- | --- |
| | Aqueous solubility | Sodium caprate solution compatibility |
| Ferrous Bisglycinate (Ferrochel) | 50 mg/mL soluble, Light green solution 50 mg/mL soluble | At 10 mg/mL in 55 mg/ml C10, severe precipitation observed, same was noted at 50% dilution |

TABLE 10-continued

Pre-formulation with iron compounds

| Material* | Observations | |
| --- | --- | --- |
| | Aqueous solubility | Sodium caprate solution compatibility |
| | in phosphate buffer pH 6.8 | (i.e. 27.5 mg/mL C10 and 5 mg/mL API) Dilution up to 90% with DW did not solubilize the above precipitate. Not soluble at 2 mg/mL API in 55 mg/mL sodium caprate 300 mg API and 550 mg sodium caprate cannot be co-solubilized in 250 mL water. Despite good aqueous solubility (also in pH 6.8), this compound is not compatible with C10. |
| Ferrous Gluconate FCC/USP* | 85 g/L (MSDS) 50 mg/mL soluble, Clear solution | Severe precipitation noted at 5 mg/mL in 55 mg/mL sodium caprate, |
| Ferrous Gluconate FCC/USP* Low HM | Solubility was tested at 50 mg/mL Clear solution | Severe precipitation noted at 5 mg/mL in 55 mg/mL sodium caprate, |

Example 3

Preparation of Tablets with Saccharide or Citric Acid

Ferric pyrophosphate soluble was used to prepare tablets with approximately 33 mg of elemental iron and different solubilizing excipients, and was tested for dissolution of both elemental iron and C10. All ingredients were weighed into weigh boats and transferred into a 250 mL Brawn PP bottle. Mixing was carried out manually for 3-5 minutes in the bottle. The mixing times includes one minute final mixing with stearic acid. The blend was carefully transferred into a weigh boat and used for tablet compression. A slight excess (2-5 mg) of blend relative to the target weight was weighed for compression to avoid transfer losses. Compression was carried out using a Globe Pharma, MTCM1; compression tooling used was 18×8 mm (S/N 426539931995-04 for both upper, lower punch and die), and compression was carried out at 1500-2000 psi.

Figure 2:
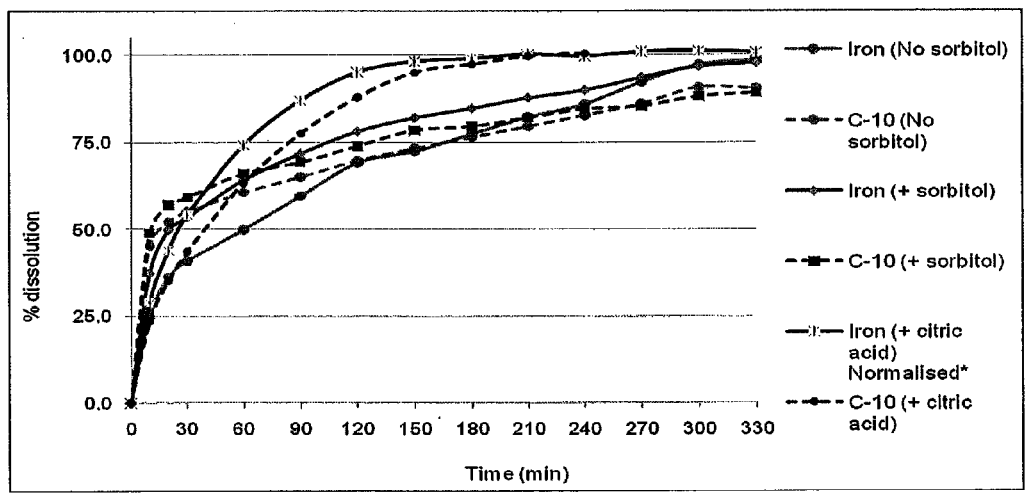
FIG. 2 shows the dissolution profiles of C10 and Fe for enhanced tablets containing ferric pyrophosphate (FPP) soluble and different solubilizing excipients.

Tablets were characterised for average weights and hardness. Also, tablets were evaluated for dissolution profiles of both elemental iron and C10. In some experiments tablet disintegration time in purified water (800 mL) was tested. Formulations prepared and results are given in Tables 11-13 and FIG. 2. The following observations were made.

1. Tablets prepared without any saccharide excipient showed very slow dissolution for both iron and C10 with 76-77% in 3 hours, and complete dissolution and/or plateau occurring in 5.5 hours.
2. Tablets prepared with saccharide (sorbitol) improved dissolution profile with 78% iron and 74% C10 released in 2 hours, followed by complete release found in 5 hours.
3. Tablets prepared with citric acid as solubilizing aid significantly improved dissolution profile of both Fe and C10 with complete release (>97%) occurring in 3 hours.

These experiments demonstrate that citric acid agents (or similar functional agents) are necessary to formulate ferric pyrophosphate soluble as enhanced iron tablets to achieve acceptable dissolution.

TABLE 11

FPP soluble tablets with and without sorbitol

| Material | Tablets without sorbitol Iron 1 - 27 EXP 1560A Amount/tablet (mg) | % | Tablets with sorbitol Iron 1 - 27 EXP 1560B Amount/tablet (mg) | % |
|---|---|---|---|---|
| FPP soluble | 290 | 34.41 | 290 | 30.38 |
| Sodium caprate | 550 | 65.18 | 550 | 57.54 |
| Partek | 0.00 | 0.00 | 112 | 11.72 |
| Stearic acid | 3.5 | 0.41 | 3.5 | 0.37 |
| Total | 844 | 100 | 956 | 100 |
| Characterization Ave. weights (mg) Ave. Hardness N | 846.41 ± 2.45 mg (n = 6) Hardness 126 ± 7N | | 846.41 ± 2.45 mg (n = 6) Hardness 126 ± 7N | |

Blended for 5 minutes, which includes 1 minute blending with stearic acid and compressed at ~1500 psi

TABLE 12

FPP soluble tablets with citric acid

| | Citric acid tablets EXP 1563 | |
|---|---|---|
| Material | Amount/tablet (mg) | % |
| FPP soluble | 290 | 30.27 |
| Sodium caprate | 550 | 57.41 |
| Citric acid | 115 | 11.95 |
| Stearic acid | 3.5 | 0.37 |
| Total Tablet weights | 958 Average tablet weight 960 mg (n = 25) Average tablet Hardness 117N (n = 3) | 100 | blended all ingredients except stearic acid for 5 minutes, and was blended further 2 minutes after addition of stearic acid. Compression was carried out at 100 bar (~1450 psi) pressure.

TABLE 13

Dissolution profiles of Fe and C10 with various ferric pyrophosphate soluble tablets contain different excipients (n = 2 tablets)

| | Tablets without sorbitol | | Tablets with sorbitol | | Citric acid tablets | |
|---|---|---|---|---|---|---|
| Time | % Iron | % C-10 | % Iron | % C-10 | % Iron* | % C-10 |
| 0 | 0.0 | 0.0 | 0.0 | 0.0 | 0.0 | 0.0 |
| 10 | 24.8 | 45.2 | 37.4 | 48.9 | 28.9 | 23.4 |
| 20 | 36.3 | 52.2 | 49.8 | 57.0 | 43.9 | 35.1 |
| 30 | 41.0 | 55.1 | 53.5 | 59.2 | 54.2 | 43.7 |
| 60 | 50.0 | 60.6 | 64.2 | 66.1 | 74.2 | 63.3 |
| 90 | 59.6 | 65.1 | 71.8 | 69.3 | 87.1 | 77.5 |
| 120 | 69.2 | 69.8 | 78.2 | 74.0 | 95.1 | 87.9 |
| 150 | 72.5 | 73.3 | 82.1 | 78.5 | 98.2 | 95.0 |
| 180 | 77.5 | 76.6 | 84.8 | 79.6 | 99.0 | 97.3 |
| 210 | 82.3 | 79.6 | 87.8 | 82.1 | 100.2 | 99.6 |
| 240 | 86.0 | 82.8 | 90.0 | 84.6 | 99.6 | 100.4 |
| 270 | 92.3 | 86.1 | 93.6 | 85.4 | 101.0 | n/a |
| 300 | 97.2 | 90.8 | 96.8 | 88.2 | 101.2 | n/a |
| 330 | 98.7 | 90.5 | 97.7 | 89.2 | 100.8 | n/a |

*% iron release reached a maximum of 107%, hence the profile was normalized for 100%

Example 4

Preparation of Tablets Containing 65 mg of Elemental Iron and Citric Acid

Figure 3:
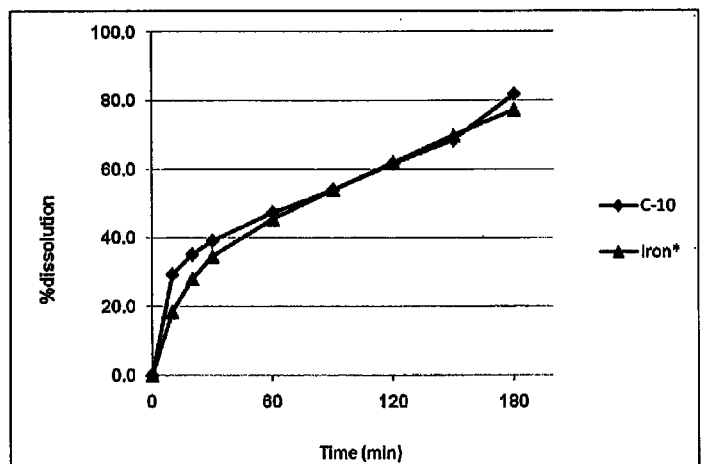
FIG. 3 shows the dissolution profiles of C10 and Fe for enhanced tablets containing FPP soluble without any solubilizing excipients (no citric acid).
Figure 4:
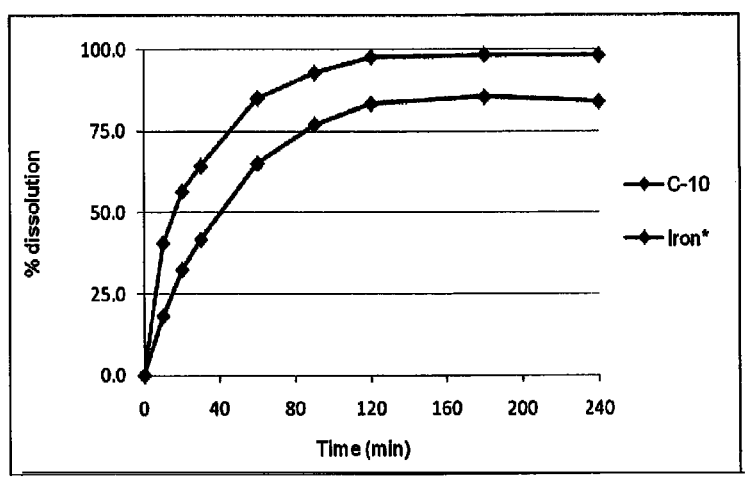
FIG. 4 shows the dissolution profiles of C10 and Fe for enhanced tablets containing FPP soluble with citric acid as solubilizing aid.

FPP soluble tablets containing 65 mg elemental iron were prepared similarly to those in Example 3. Table 14 contains details of the tablets. These tablets were evaluated for dissolution profiles (FIGS. 3 and 4). As noticed previously, tablets without citric acid showed very slow dissolution profiles as complete release was not achieved even after 3 hours; only 77% Fe and 82% C10 was dissolved (Table 15). On the other hand, tablets containing citric acid (9%) showed good dissolution profiles with >97% Fe release occurring in 2 hours. The release of C10 was not complete, however it reached plateau (84%) at 2 hours.

TABLE 14

FPP soluble tablets containing 65 mg elemental iron

| Material | Tablets Without citric acid EXP 1574 Sample A Amount/tablet (mg) | % | Tablets with Citric acid EXP 1574 Sample B Amount/tablet (mg) | % |
|---|---|---|---|---|
| FPP soluble | 574 | 50.91 | 574 | 46.22 |
| Sodium caprate | 550 | 48.78 | 550 | 44.28 |
| Citric acid | — | — | 114.5 | 9.22 |
| Stearic acid | 3.5 | 0.31 | 3.5 | 0.28 |
| Total | 1128 | 100 | 1242 | 100 |
| Tablet characterization | Average Tablet wt 1132 mg (n = 10) Average Hardness 146N (n = 3), Dimensions length 18 mm, width 8 mm, and thickness 8.2 mm Disintegration time 1st tablet 18 min 40 sec, last tablet 23 min 10 sec | | Average Tablet wt 1247 mg (n = 10) Average Hardness 168N (n = 3), Dimensions length 18 mm, width 8 mm, and thickness 9 mm Disintegration time 1st tablet 15 min 56 sec, last tablet 19 min 12 sec | |

All materials were dispensed, screened thorough 355 mesh, and blended for 3 minutes, 18 × 8 mm tool Compression force 2000 psi.

TABLE 15

Dissolution profiles of Fe and C10 with FPP soluble enhanced tablets with and without citric acid (n = 2 tablets)

| | % dissolution No citric acid | | % dissolution Citric acid | |
|---|---|---|---|---|
| Time | Iron | C-10 | Iron | C-10 |
| 0 | 0.0 | 0.0 | 0.0 | 0.0 |
| 10 | 18.4 | 29.3 | 40.7 | 18.3 |
| 20 | 28.0 | 35.1 | 56.4 | 32.5 |
| 30 | 34.5 | 39.1 | 64.3 | 41.8 |
| 60 | 45.6 | 47.4 | 85.2 | 65.2 |
| 90 | 54.0 | 53.9 | 92.8 | 77.1 |
| 120 | 61.9 | 61.6 | 97.6 | 83.5 |
| 150 | 69.8 | 68.4 | ND | ND |
| 180 | 77.3 | 81.7 | 98.3 | 85.6 |
| 240 | | | 98.2 | 84.1 |

Example 5

Tablets Containing 65 mg of Elemental Iron with Citric Acid and with/without Saccharide Tablets with 65 mg elemental iron were prepared with citric acid in the tablet cores according to the formulae in Table 16 using the procedure in Example 3. Tablets were prepared with and without saccharide. The following points summarize the results, which are given in Tables 16 and 17.

Figure 5:
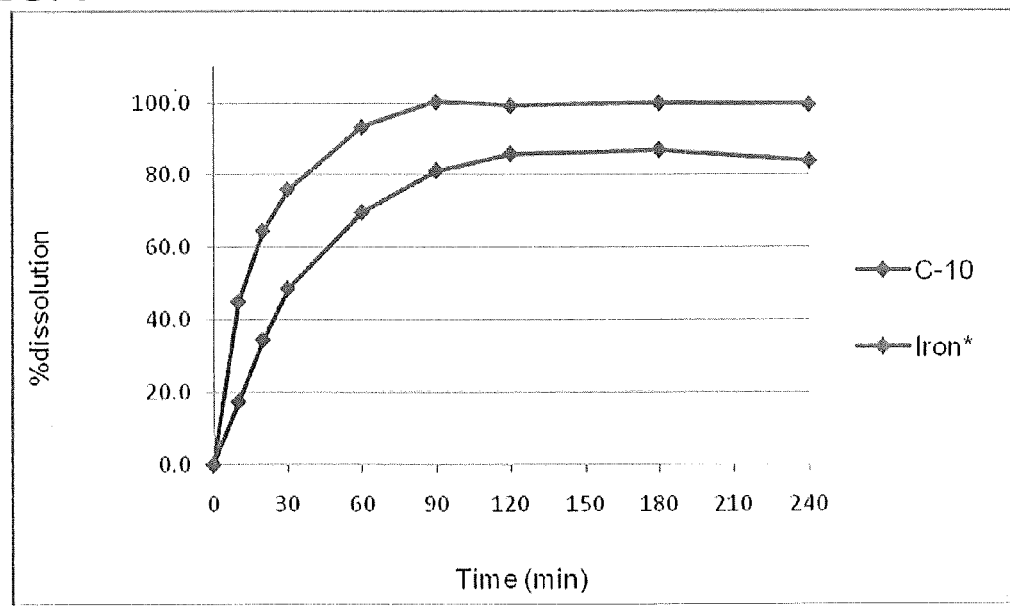
FIG. 5 shows the dissolution profiles of C10 and Fe for enhanced tablets containing FPP soluble and both citric acid plus sorbitol.

1) High concentration of citric acid (11.6%) (148 mg/tablet). Complete dissolution of Fe was observed at 60 minutes, C10 dissolution was not complete however, it reached plateau at 90 minutes (FIG. 5).

Figure 6:
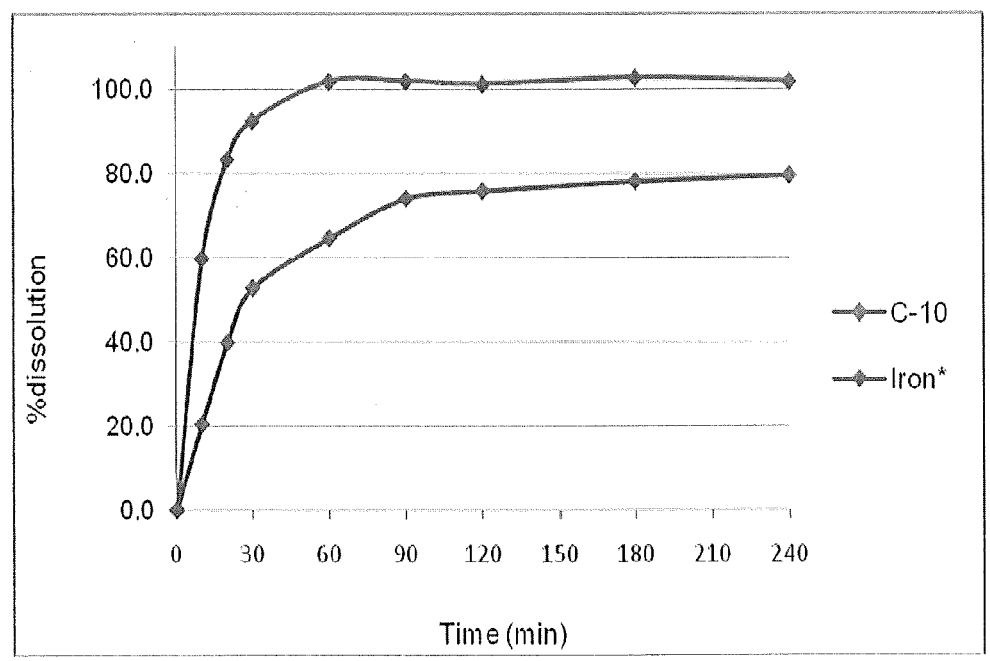
FIG. 6 shows the dissolution profiles of C10 and Fe for enhanced tablets containing FPP soluble and high concentration of citric acid (148 mg tablet). Iron content normalized for 100%.

2) Tablets containing both citric acid and sorbitol (8.4% each). Complete dissolution of iron was noticed at 90 minutes, C10 dissolution was not complete however, it reached plateau at 90 minutes (FIG. 6).

TABLE 16

Iron tablets of FPP soluble containing 65 mg elemental iron and varying concentrations of solubilizing excipients

| Material | Sorbitol + Citric acid NB Iron 1 - Page 37 EXP 1579 Sample A | | High Concentration of Citric acid NB Iron 1 - Page 38 EXP 1580 Sample B | |
|---|---|---|---|---|
| | Qty per tablet (mg) | % | Qty per tablet (mg) | % |
| FPP soluble | 574 | 42.31 | 574 | 44.98 |
| Sodium caprate | 550 | 40.55 | 550 | 43.10 |
| Citric acid | 115 | 8.48 | 148 | 11.60 |
| Sorbitol | 115 | 8.48 | 0 | 0 |
| Stearic acid | 3.5 | 0.26 | 3.5 | 0.27 |
| Total | 1357 | 100 | 1276 | 100 |
| Tablet characterization | Ave. Tablet wt 1359 mg (n = 25) Hardness 180N (n = 3), Dimensions length 18 mm, width 8 mm, and thickness 9.7 mm Disintegration time 1$^{st}$ tablet 13 min 24 sec, last tablet 17 min 44 sec | | Ave. Tablet wt 1278 mg (n = 25) Hardness 158N (n = 3) Dimensions length 18 mm, width 8 mm, and thickness 9.1 mm Disintegration time 1$^{st}$ tablet 13 min 40 sec, last tablet 16 min 57 sec | |

All materials were dispensed, screened thorough 355 mesh, blended for 3 minutes, 18 × 8 mm tool Compression force 2000 psi.

TABLE 17

Dissolution profiles FPP soluble tablets containing varying quantities of solubilizing excipients (n = 2 tablets)

| | % dissolution citric acid plus sorbitol | | % dissolution High concentration of Citric acid | |
|---|---|---|---|---|
| Time | *Iron | C-10 | *Iron | C-10 |
| 0 | 0.0 | 0.0 | 0.0 | 0.0 |
| 10 | 45.3 | 17.3 | 58.7 | 20.4 |
| 20 | 65.0 | 34.3 | 81.8 | 39.8 |
| 30 | 76.5 | 48.5 | 90.8 | 52.7 |
| 60 | 93.7 | 69.6 | 100 | 64.5 |
| 90 | 100.7 | 81.1 | 100.1 | 73.9 |
| 120 | 99.7 | 85.7 | 99.4 | 75.7 |
| 180 | 100.4 | 86.8 | 100.9 | 78.0 |
| 240 | 100.0 | 83.8 | 100.0 | 79.4 |

*% Iron reached a maximum of approx. 114%, hence has been normalized for 100% release Conclusions Tablets with citric acid (12% or 148 mg/tablet) were preferred. These experiments reveal that citric acid (or similar functional agents) are necessary to formulate ferric pyrophosphate soluble iron tablets to achieve an acceptable dissolution profile. The target dissolution profile is rapid, providing co dissolution of both iron and enhancer.

Example 6

Preparation of Tablets with Various Solubilizing Excipients

The following experiments were performed to investigate citric acid, sodium citrate or ascorbic acid as solubilizing excipients.

Evaluation systems were made as in Example 2. Citric acid and sodium citrate were evaluated as solubilizers with soluble iron pyrophosphate (7.83 mg Fe), along with the relevant concentration of citric acid or sodium citrate (15 mg) in 55 mg/mL solution of sodium caprate.

With citric acid as the solubilizer (Table 18), precipitation was noticed up to 17 mg of Fe, and a hazy orange dispersion was noticed from 21 mg Fe onwards. On the other hand, sodium citrate as the solubilization aid (Table 19) was found to be relatively superior as dispersion characteristics were observed from 7.6 mg Fe onwards.

TABLE 18

Solution compatibility of FPP soluble (API) with sodium caprate in the presence of varying concentrations of citric acid

| Elemental Iron (mg) | | Iron compound concentration (mg) | | Observation |
|---|---|---|---|---|
| Planned | Actual | Increments of API added | Total API | |
| | | | 62.2 | Cloudy white ppt#(C10) at the bottom |
| 7.83 | 7.62 | 5.1 | 67.3 | Soluble, pH 8.45 |
| 10 | 8.93 | 11.6 | 78.90 | ppt as above |
| 12 | 16.93 | 70.6 | 149.50 | ppt as above |
| 15 | 20.57 | 32.17 | 181.67 | Hazy Light orange dispersion |
| 20 | 32.27 | 103.3 | 284.97 | Clear colloidal 8.06 |
| NC* | 47.27 | 132.45 | 417.42 | As above |
| 65 | 66.00 | 165.58 | 583 | As above | ppt: precipitate;
*NC Not calculated

TABLE 19

Solution compatibility of FPP soluble with sodium caprate in the presence of varying concentrations of sodium citrate

| Elemental Iron (mg) | | Iron compound concentration (mg) | | Observation |
|---|---|---|---|---|
| Planned | Actual | Increments of API added | Total API | |
| | | | 62.2 | Fine white PPT at bottom |
| 7.83 | 7.98 | 8.3 | 70.5 | Soluble pH 8.45 |
| 10 | 10.45 | 21.8 | 92.3 | |
| 12 | 11.40 | 8.4 | 100.7 | |
| 15 | 15.06 | 32.3 | 133 | |
| 20 | 20.16 | 45 | 178 | Clear colloidal 8.15 |
| 25 | 26.35 | 54.7 | 232.7 | |
| 30 | 30.59 | 37.4 | 270.1 | |
| 40 | 40.88 | 90.9 | 361 | |
| 50 | 51.07 | 90 | 451 | |
| 65 | 66.00 | 132 | 583 | | ppt: precipitate

Example 7

Preparation of Tablets with Sodium Citrate

Figure 7:
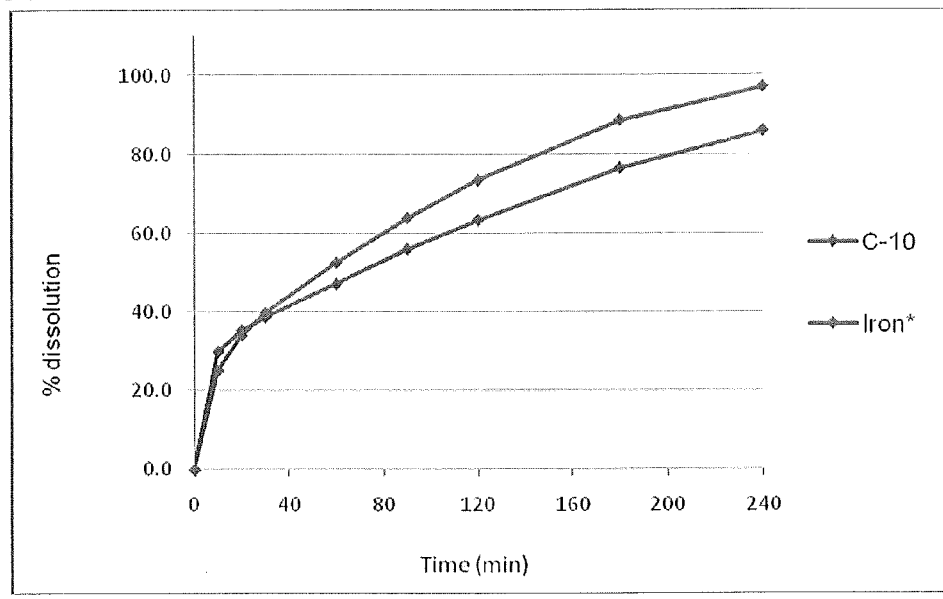
FIG. 7 shows the dissolution profiles of C10 and Fe for enhanced tablets containing FPP soluble and sodium citrate (148 mg tablet) from n=2 tablets.

Iron tablets were made using sodium citrate in place of citric acid according to the procedure used in Example 3. Details of the tablets are shown in Table 20. Dissolution of both Fe and C10 was slow, however complete release of Fe and >80% C10 was achieved in 4 hours (FIG. 7).

Figure 8:
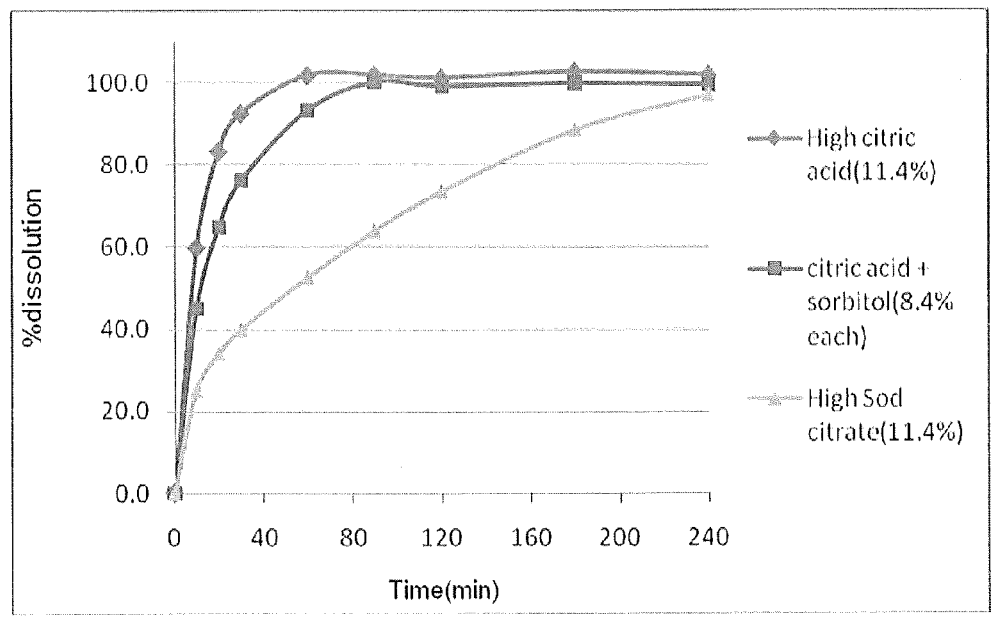
FIG. 8 shows the dissolution profiles of Fe for enhanced tablets containing FPP soluble and different solubilizing excipients.

The comparative dissolution profiles of Fe from citric acid and sodium citrate is depicted in FIG. 8. The results indicate citric acid is the better solubilizer.

TABLE 20

Iron tablets of FPP soluble containing 65 mg elemental iron and sodium citrate as solubilizing excipient

| Material | FPP soluble tablets with sodium citrate EXP 1598 | |
|---|---|---|
| | Amount tablet (mg) | % |
| FPP soluble | 574 | 44.98 |
| Sodium caprate | 550 | 43.10 |
| Sodium citrate | 148.4 | 11.64 |
| Stearic acid | 3.5 | 0.28 |
| Total | 1276 | 100.00 |
| Tablet characterization | | |
| Average weight (mg ± SD; n = 6) | 1278.90 ± 1.35 | |
| Average Hardness (N ± SD; n = 4) | Hardness 131 ± 6N | |

Blended for 5 minutes and compression was carried out at 1500 psi.

Example 8

Preparation of Iron Tablets Containing Ascorbic Acid

Figure 9:
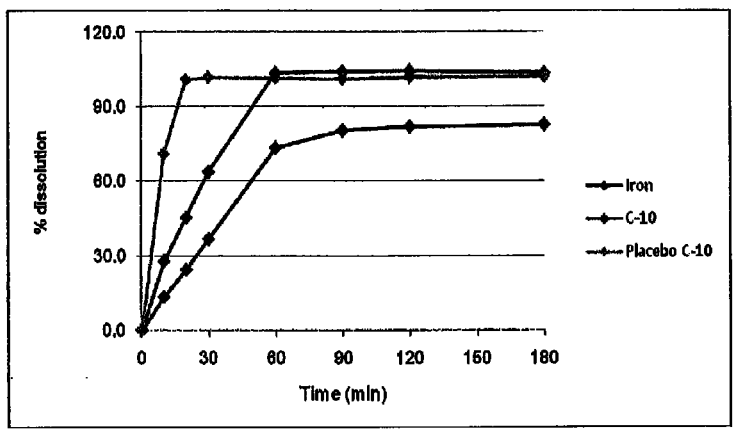
FIG. 9 shows the dissolution profiles of Fe and C10 for enhanced tablets containing FPP soluble and ascorbic acid and placebo C10 tablets.
Figure 10:
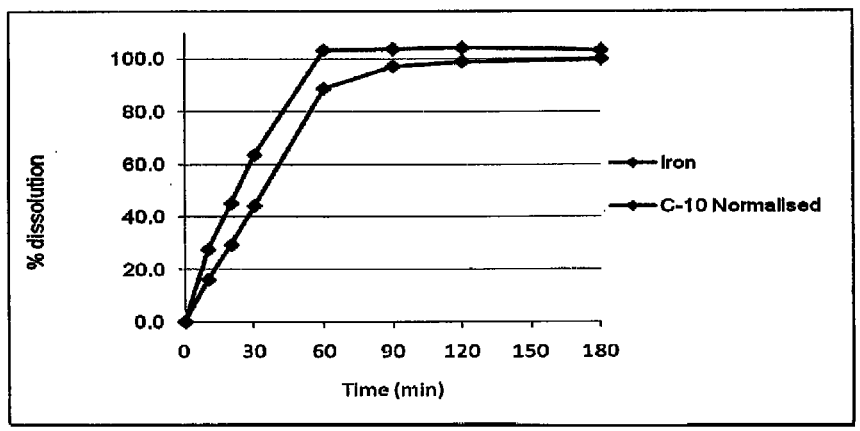
FIG. 10 shows the profiles of Fe and C10 normalized for enhanced tablets containing FPP soluble and ascorbic acid.
Figure 11:
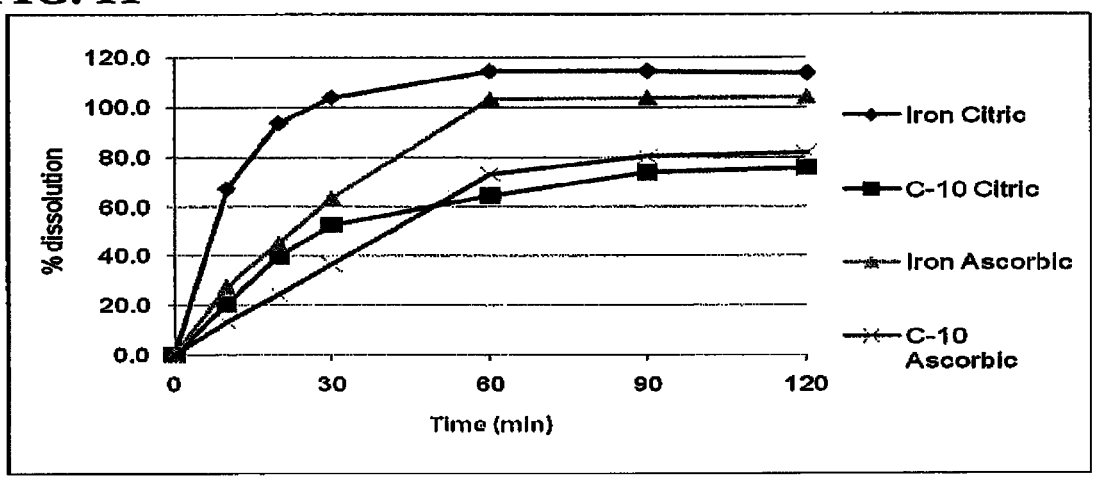
FIG. 11 shows the dissolution profiles of Fe and C10 for enhanced tablets containing FPP soluble and different solubilizing excipients.

Because ascorbic acid is known to be an oral absorption promoter of iron, tablets were manufactured using ascorbic acid in place of citric acid according to the procedure in Example 2. Details of the tablets are shown in Table 21. The results indicate Fe was dissolved in 60 minutes and C10 dissolution reached a plateau with 80% release (FIG. 9). A control experiment carried out with C10 alone (exact tablet composition: 550 mg C10, 3.5 mg stearic acid, 115 mg sorbitol) showed 100% release. The data were replotted by normalizing C10 and showed that 97% C10 had dissolved after 90 minutes and reached a plateau (FIG. 10). Comparative dissolution profiles of citric acid and ascorbic acid tablets are depicted in FIG. 11, and results indicate rapid and complete release with citric acid. Ascorbic acid tablets show a relatively superior co-release of both Fe and C10, however complete release was not achieved.

TABLE 21

Iron tablets of FPP soluble containing 65 mg elemental iron and ascorbic acid as solubilizing excipient

| Material | Ascorbic acid tablets EXP 1615 | |
|---|---|---|
| | Amount/tablet (mg) | % |
| FPP soluble | 574 | 44.98 |
| Sodium caprate | 550 | 43.10 |
| Ascorbic acid | 148.4 | 11.64 |
| Stearic acid | 3.5 | 0.28 |
| Total | 1276 | 100.00 |
| Tablet characterization | | |
| Average weight (mg ± SD; n = 6) | 1279.27 ± 2.20 | |
| Average Hardness (N ± SD; n = 4) | Hardness 135 ± 6N | | blended for 5 minutes, and compressed at 1500 psi.

Example 9

Preparation of Iron Tablets with Varying Concentrations of Citric Acid

Additional batches of enhanced tablets were prepared with varying concentrations of citric acid. These concentrations were 12%, 15%, and 21% according to the procedure in Example 3 The 15% tablets had a reduced concentration of iron. Details of the tablets are shown in Table 22).

Figure 12:
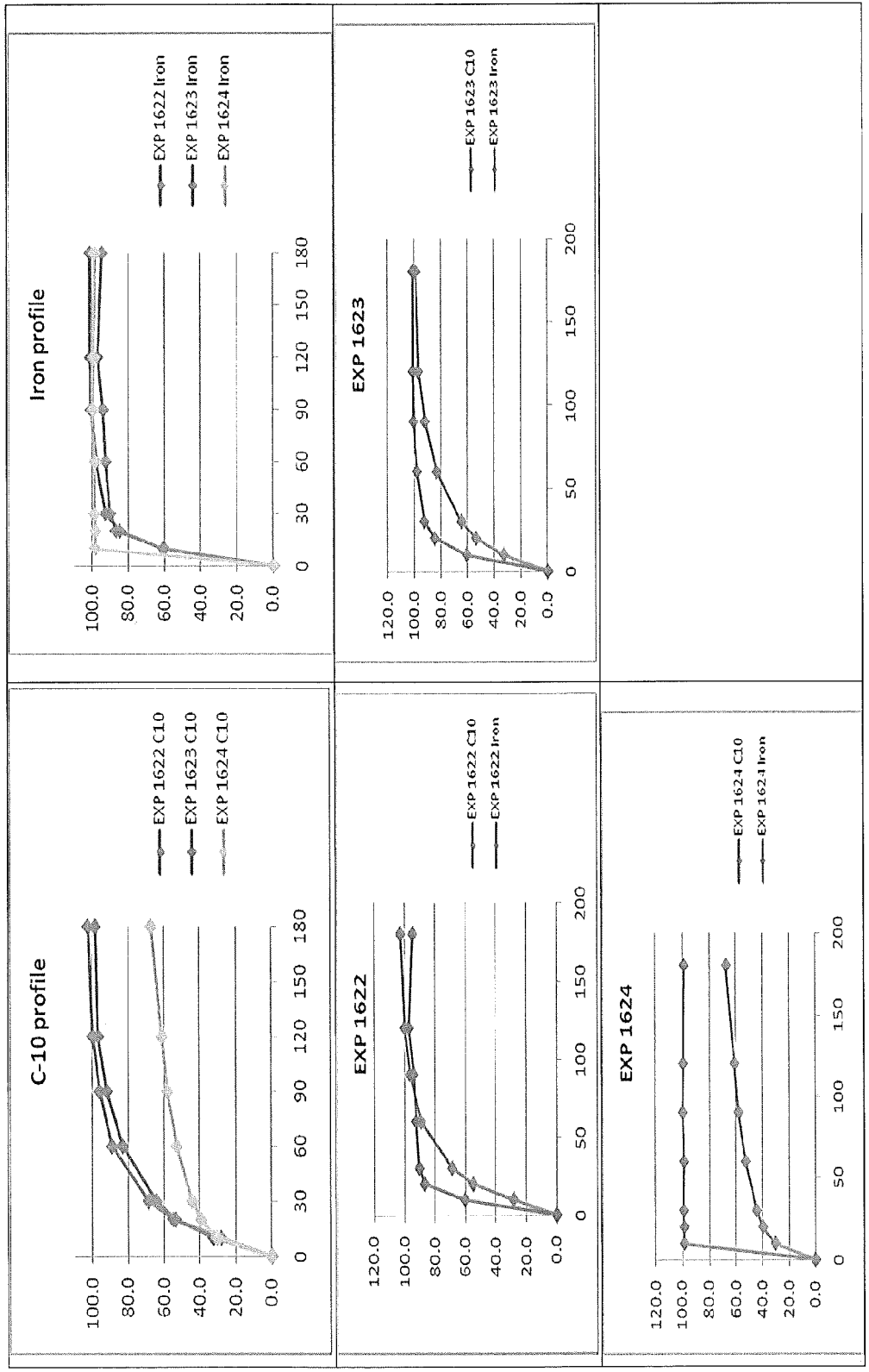
FIG. 12 shows the dissolution profiles of Fe and C10 for enhanced iron tablets containing varying concentrations of citric acid (n=2 tablets).

Fe release was rapid and complete with all the batches (FIG. 12). Tablets with 12% and 15% (API load 50%) showed release of C10 in 120 minutes. These results demonstrate 100% recovery of C10 can be achieved.

TABLE 22

Iron tablets of FPP soluble containing 65 mg elemental iron and ascorbic acid as solubilizing excipient

| | Target tablet EXP 1622 | | 50% Iron concentration EXP 1623 | | Very high citric acid EXP 1624 | |
|---|---|---|---|---|---|---|
| Material | Qty/tablet (mg) | % | Qty/tablet (mg) | % | Qty/tablet (mg) | % |
| FPP soluble | 574 | 44.98 | 287 | 29.02 | 574 | 40.31 |
| Sodium caprate | 550 | 43.10 | 550 | 55.62 | 550 | 38.62 |
| Citric acid | 148.4 | 11.63 | 148.4 | 15.00 | 296.8 | 20.84 |
| Stearic acid | 3.5 | 0.27 | 3.5 | 0.35 | 3.5 | 0.25 |
| Total | 1276 | 100 | 989 | 100 | 1424 | 100 |
| Tablet characterization | Ave. Tablet wt 1282 mg(n = 20) | | Ave. Tablet wt 989 mg(n = 20) | | Ave. Tablet wt 1428 mg(n = 20) | |

All material were dispensed, screened thorough 355mesh, blended for 3 minutes, 18 × 8 mm tool Compression force 2000 psi.

Example 10

Replicate Batches of Iron Tablets

Figure 13:
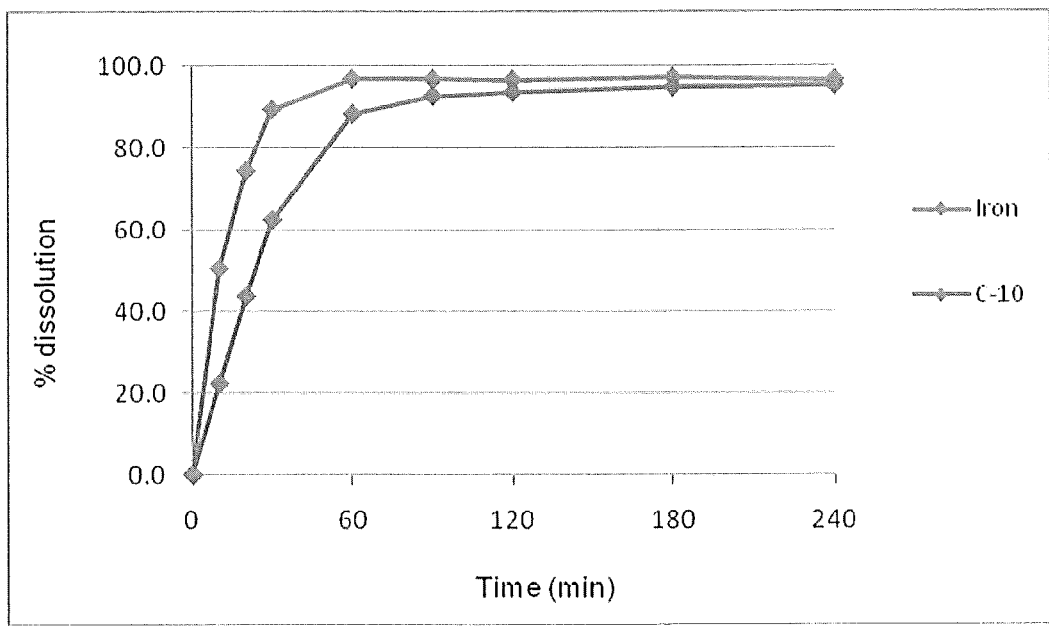
FIG. 13 shows the dissolution profiles of Fe and C10 for enhanced iron tablets containing FPP soluble and citric acid prepared to evaluate C10 recovery and co release (EXP 1642).
Figure 14:
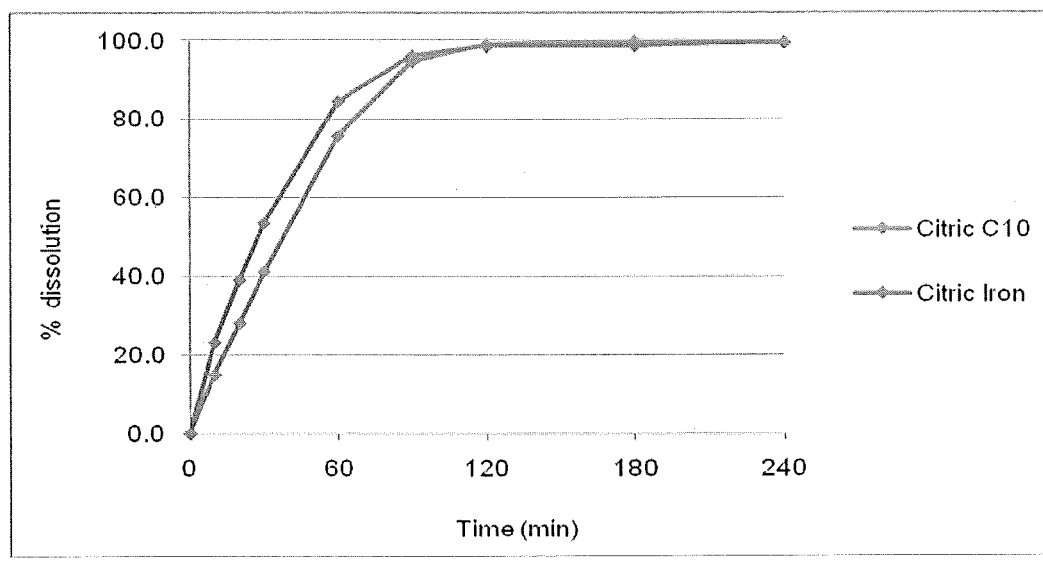
FIG. 14 shows the dissolution profiles of Fe and C10 for enhanced iron tablets containing FPP soluble and citric acid prepared to evaluate C10 recovery and co release (EXP 1649).
Figure 15:
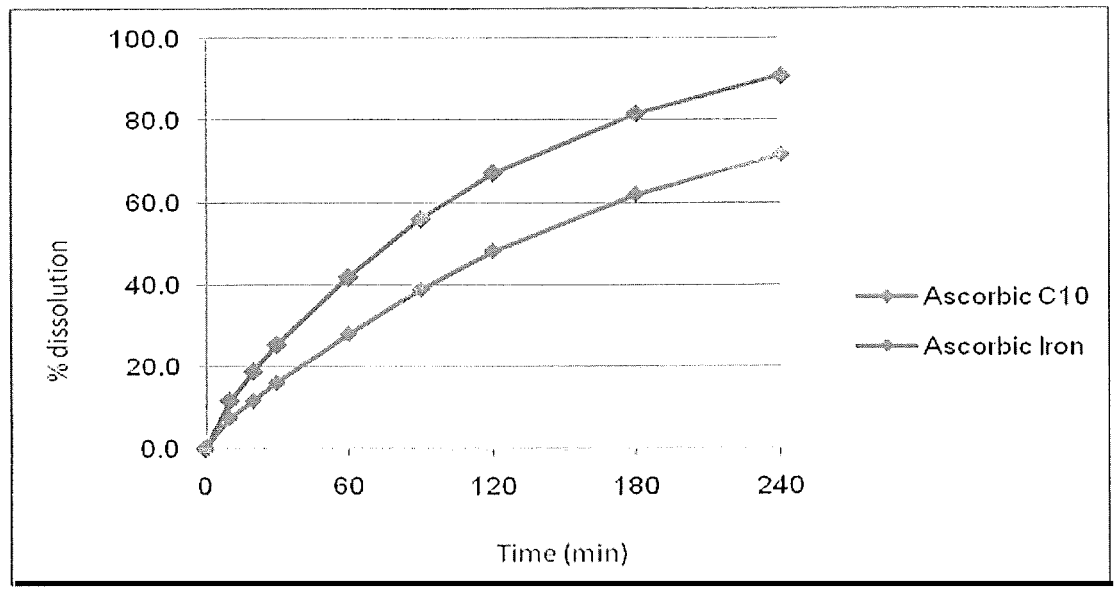
FIG. 15 shows the dissolution profiles of Fe and C10 for enhanced iron tablets containing FPP soluble and ascorbic acid prepared to evaluate C10 recovery and co release (EXP 1650).

Additional batches of iron tablets were prepared according to the procedure in Example 3 to evaluate the reproducibility of manufacture and performance. Details of the tablet batches are shown in Table 23. The results indicate rapid and complete release with citric acid. Ascorbic acid tablets showed a relatively superior co-release of both iron and C10, but complete release was not achieved (Table 24 and FIGS. 13-15).

citric acid and sodium citrate were prepared according to the procedure in Example 3. Details of these tablets are shown in Tables 25 and 26.

Figure 16:
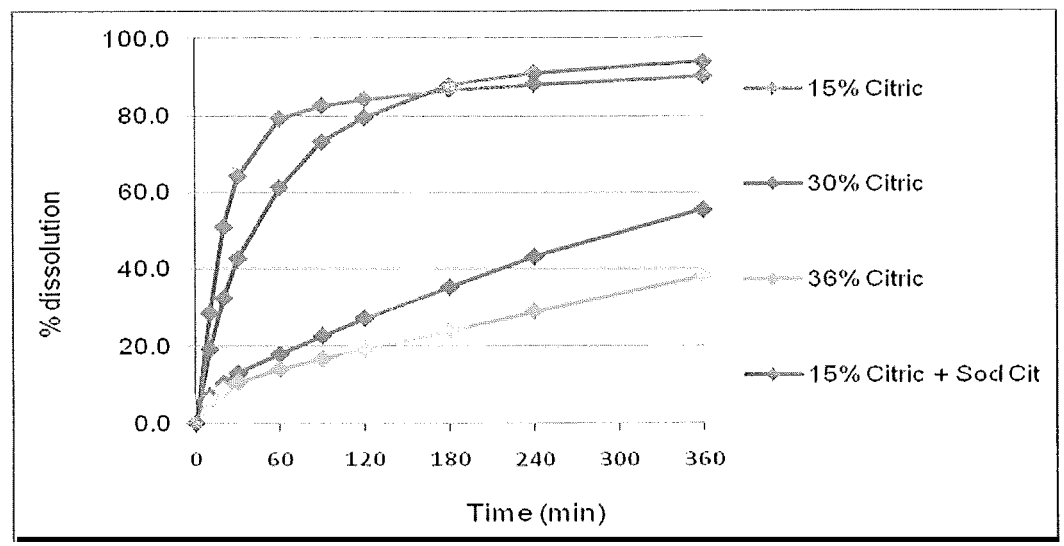
FIG. 16 shows the dissolution profiles of C10 for enhanced iron tablets containing FPP/FCC and different levels of solubilizing excipients.
Figure 17:
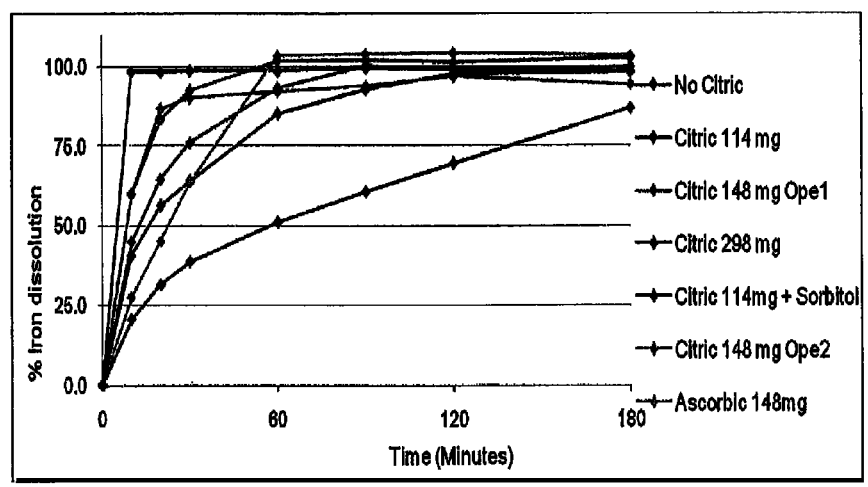
FIG. 17 shows the comparative dissolution profiles of Fe with various enhanced iron tablets.
Figure 18:
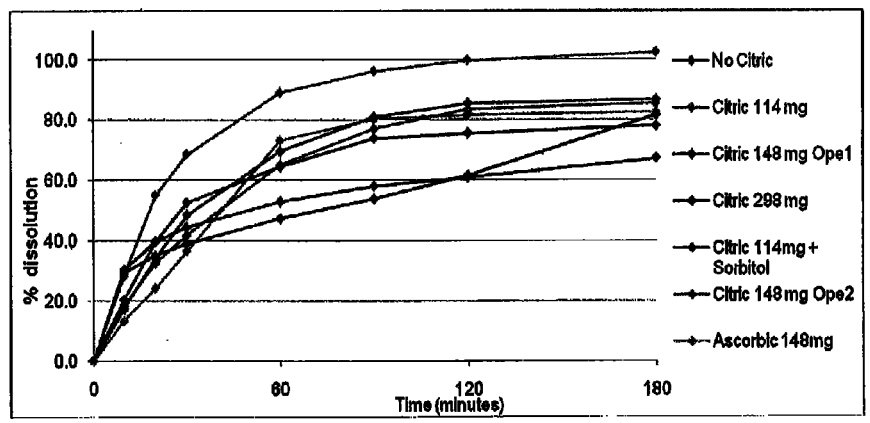
FIG. 18 shows the comparative dissolution profiles of C10 with various enhanced iron tablets.

The dissolution of sodium caprate was rapid in the presence of 15% citric acid or sodium citrate. Within 2 hours, C10 dissolution reached plateau with 80-84% release (FIG. 16). Increasing citric acid content in the tablets decreased C10 dissolution with <60% release with 30% citric acid and <40%

TABLE 23

Iron tablets of FPP soluble containing 65 mg elemental iron and solubilizing excipients

| Material | Operator 1/citric EXP 1642 Qty/tablet (mg) | % | Operator2/citric EXP 1649 Qty/tablet (mg) | % | Operator 2/ascorbic EXP 1650 Qty/tablet (mg) | % |
|---|---|---|---|---|---|---|
| FPP soluble | 574 | 44.98 | 580 | 45.24 | 580 | 45.24 |
| Sodium caprate | 550 | 43.10 | 550 | 42.90 | 550 | 42.90 |
| Citric acid | 148.4 | 11.63 | 148.4 | 11.58 | 0 | 0 |
| Ascorbic Acid | 0 | 0 | 0 | 0 | 148.4 | 11.58 |
| Stearic acid | 3.5 | 0.27 | 3.5 | 0.27 | 3.5 | 0.27 |
| Total | 1276 | 100 | 1282 | 100 | 1282 | 100 |
| Tablet characterization | | | | | | |
| Average weight(mg ± SD; n = 6) | 1275.07 ± 0.91 | | 1282.15 ± 0.93 | | 1283.75 ± 3.28 | |
| Average Hardness(N ± SD; n = 4) | Tablet hardness not tested | | 128 ± 2N | | 130 ± 6N | |

All material were dispensed and blended for 5-6 minutes, 18 × 8 mm tool Compression force 1500-2000 psi.

TABLE 24

Iron tablets of FPP soluble containing 65 mg elemental iron and solubilizing excipients

| | EXP 1642 (Ope 1 citric) % dissolved (n = 2 tablets) | | EXP 1649 (Ope 2 citric) % dissolved (n = 6 tablets) | | | | EXP 1650(ascorbic) % dissolved (n = 6 tablets) | | | |
|---|---|---|---|---|---|---|---|---|---|---|
| Time | C10 | Iron | C10 | RSD | Iron | RSD | C-10 | RSD | Iron | RSD |
| 0 | 0.0 | 0.0 | 0.0 | 0.0 | 0.0 | 0.0 | 0.0 | 0.0 | 0.0 | 0.0 |
| 10 | 22.2 | 50.5 | 15.0 | 21.0 | 23.2 | 16.4 | 7.4 | 11.7 | 11.6 | 7.3 |
| 20 | 43.6 | 74.4 | 28.1 | 13.9 | 39.1 | 9.3 | 11.6 | 8.0 | 18.7 | 8.8 |
| 30 | 62.4 | 89.4 | 41.2 | 10.6 | 53.6 | 7.0 | 15.9 | 7.5 | 25.4 | 9.9 |
| 60 | 88.2 | 96.9 | 75.8 | 6.3 | 84.6 | 4.2 | 27.9 | 11.5 | 41.9 | 11.2 |
| 90 | 92.6 | 96.8 | 94.7 | 2.3 | 96.3 | 1.7 | 38.8 | 10.3 | 56.0 | 10.7 |
| 120 | 93.6 | 96.7 | 99.1 | 1.7 | 98.6 | 0.7 | 48.2 | 10.1 | 67.3 | 9.6 |
| 180 | 94.8 | 97.3 | 99.9 | 1.1 | 98.8 | 0.5 | 61.9 | 8.2 | 81.7 | 7.2 |
| 240 | 95.2 | 96.7 | 99.4 | 1.2 | 99.6 | 0.5 | 71.5 | 5.3 | 90.8 | 4.1 |

Example 11

Iron Tablets Prepared with Varying Levels of Citric Acid and Sodium Citrate

Iron tablets containing ferric pyrophosphate (Food Chemicals Codex (FCC)) were manufactured with varying levels of release with 36% citric acid. None of these tablets showed Fe dissolution (or solubilization), hence neither ferric pyrophosphate alone nor in combination with sodium citrate at a level similar to the soluble version is suitable. These data confirm the conclusions obtained in Example 2 relative to ferric pyrophosphate versus soluble ferric pyrophosphate.

TABLE 25

Iron tablets of FPP/FCC containing 65 mg elemental iron and citric acid as solubilizing excipient

| Material | 15% citric acid EXP 1639 | | 36% citric acid EXP 1640 | | 30% citric acid EXP 1641 | |
|---|---|---|---|---|---|---|
| | Qty/tablet (mg) | % | Qty/tablet (mg) | % | Qty/tablet (mg) | % |
| FPP FCC | 260 | 27.01 | 260 | 20.51 | 260 | 22.35 |
| Sodium caprate | 550 | 57.19 | 550 | 43.42 | 550 | 47.32 |
| Citric acid | 148.4 | 15.43 | 453 | 35.79 | 349 | 30.03 |
| Stearic acid | 3.5 | 0.36 | 3.5 | 0.28 | 3.5 | 0.30 |
| Total | 962 | 100 | 1267 | 100 | 1162 | 100 |
| Tablet characterization | | | | | | |
| Average weight(mg ± SD; n = 6) | 962.59 ± 1.39 mg | | 1267.31 ± 0.72 mg | | 1162.93 ± 0.52 mg | |
| Average Hardness(N ± SD; n = 4) | 140 ± 6N | | 142 ± 5N | | 141 ± 5N | |

All material were dispensed and blended for 5 minutes, 18 x 8 mm tool Compression force 1000-2000 psi.(Average~1500 psi)

TABLE 26

Iron tablets of FPP/FCC containing 65 mg elemental iron and citric acid plus sodium citrate as solubilizing excipient

| Material | FPP FCC tablets with sodium citrate and citric acid. EXP 1644 | |
|---|---|---|
| | Qty/tablet (mg) | % |
| FPP FCC | 260 | 19.84 |
| Sodium caprate | 550 | 42.01 |
| Sodium citrate | 347 | 26.54 |
| Citric acid | 148.4 | 11.34 |
| Stearic acid | 3.5 | 0.27 |
| Total | 1309 | 100 |
| Tablet characterization | | |
| Average weight (mg ± SD; n = 6) | 1309.70 ± 1.26 mg | |
| Average Hardness (N ± SD; n = 4) | 142 ± 4N | |

All material were dispensed and blended for 5 minutes, 18 x 8 mm tool Compression force 1500-2000 psi Example 12

Pharmacokinetic Study of Dosage Forms of Iron Pyrophosphate

A two way cross over preclinical study was undertaken to evaluate the relative fasted oral bioavailability of iron (soluble ferric pyrophosphate) formulation versus an unenhanced control formulation of ferrous sulfate in an iron deficient intraduodenally cannulated beagle dog model. Twelve female dogs were included in the study and were divided into two groups of six animals each (Group A (n=6) and Group B (n=6). These dogs were made iron deficient by phlebotomy prior to dosing of the test formulations. A drop in plasma iron levels of ~25% and/or a drop of ~20% in hematocrit (measured as % packed cell volume (PCV) relative to pre-phlebotomy values was considered as iron deficiency.

Experimental Details

The live phase portion of this study was 18 days in duration (including the iron deficiency induction); the live-phase began on day −3 with clinical observation and live-phase ended after the 24 hour blood collection in Period 2.

The induction phase of the study to induce the iron deficient state was designated as Days 0-10. Iron deficiency was induced by collecting an estimated 20% of the dog's blood volume from the jugular vein, on Days 0, 1, 4, 5, 8 and 11.

Phlebotomy blood samples taken during the anemia induction phase were used for the measurement of iron levels and PCV. Animals were allocated to two groups (Group A and B) by stratified randomization based on pre-study body weights.

On day 11 the iron deficiency target was reached. Both formulations were administered to each group in a crossover design. The washout period between each dose was 24 hours (Refer Table 27). Blood samples were collected and analyzed for plasma iron levels at pre-dose (T0), 0.5, 1, 2, 4, 6, and 24 hours following test article administration. Oral bioavailability of enhanced iron TI2 was estimated relative to the control formulation ferrous sulfate alone unenhanced TI1.

TABLE 27

Study design for crossover dosing of test items

| Period No. | Animals Group (n = 6) | Day of Dose | Route | Formulation name | Dose (mg/dog**) | Formulation Code Batch No | Blood Collection Time Points |
|---|---|---|---|---|---|---|---|
| 1 | A | 12-13 | ID* (Solution) | unenhanced TI1 | Ferrous sulfate ~15 mgFe/dog | UC2** EXP1667 A | T0(Pre-dose), 0.5, 1, 2, 4, 6 and, 24 hrs |
| 1 | B | 12-13 | ID (Solution) | Iron TI2 | Ferric pyrophosphate Form B ~15 mgFe and 550 mg enhancer/dog | EF2*** EXP1668A | T0(Pre-dose), 0.5, 1, 2, 4, 6 and, 24 hrs |

TABLE 27-continued

Study design for crossover dosing of test items

| Period No. | Animals Group (n = 6) | Day of Dose | Route | Formulation name | Dose (mg/dog**) | Formulation Code Batch No | Blood Collection Time Points |
|---|---|---|---|---|---|---|---|
| 2 | A | 13-14 | ID (Solution) | Iron TI2 | Ferric pyrophosphate form B ~15 mgFe and 550 mg enhancer/dog | EF2 EXP1668B | T0(Pre-dose), 0.5, 1, 2, 4, 6 and, 24 hrs |
| 2 | B | 13-14 | ID (Solution) | unenhanced TI1 | Ferrous sulfate ~15 mgFe/dog | UC2 EXP1667 B | T0(Pre-dose), 0.5, 1, 2, 4, 6 and, 24 hrs |

*ID = Intraduodenal,
**UC2: Un-enhanced Control formulation 2; Each mL contains 1.5 mg elemental iron
***EF2: Enhancer formulation 2. Each mL contains 1.5 mg elemental iron, and 55 mg Sodium Caprate, and 3.43 mg citric acid.

Data Analysis

Upon receipt of bio-analytical data, the individual animal plasma iron concentration data were loaded into an Excel spreadsheet (Microsoft® office Excel 2003). PK parameters including $AUC_{0-t}$, $C_{max}$, and $T_{max}$, were calculated using macros written for MS Excel by Usansky et al.

Because systemic iron levels comprise both the endogenous iron pool and exogenously administered iron absorbed from the formulation, the following analysis was carried out: 1) Evaluation of total plasma iron vs. time profile; and 2) Evaluation of plasma iron corrected for base line levels (CT-T0), obtained by subtracting the total plasma iron of each animal prior to dose administration (T0) from total plasma iron at each time point (CT). Both total plasma iron vs. time and plasma iron corrected for base line vs. time data were used to calculate the PK parameters. For plasma iron corrected for base line, negative values were considered as zero for AUC calculations.

Only $AUC_{0-6}$ was used to evaluate the relative oral bioavailability ($F_{rel}$), which is presented as the fold increase of iron TI2 relative to the ferrous sulfate formulation. The pre-dose data generated from phlebotomy experiments, plasma iron levels and % PCV, are also summarized.

Results

This summary includes 1) pharmacokinetic (PK) data analysis and 2) main observations of iron deficiency induction.

Summary of Pharmacokinetic (PK) Parameters

Figure 19:
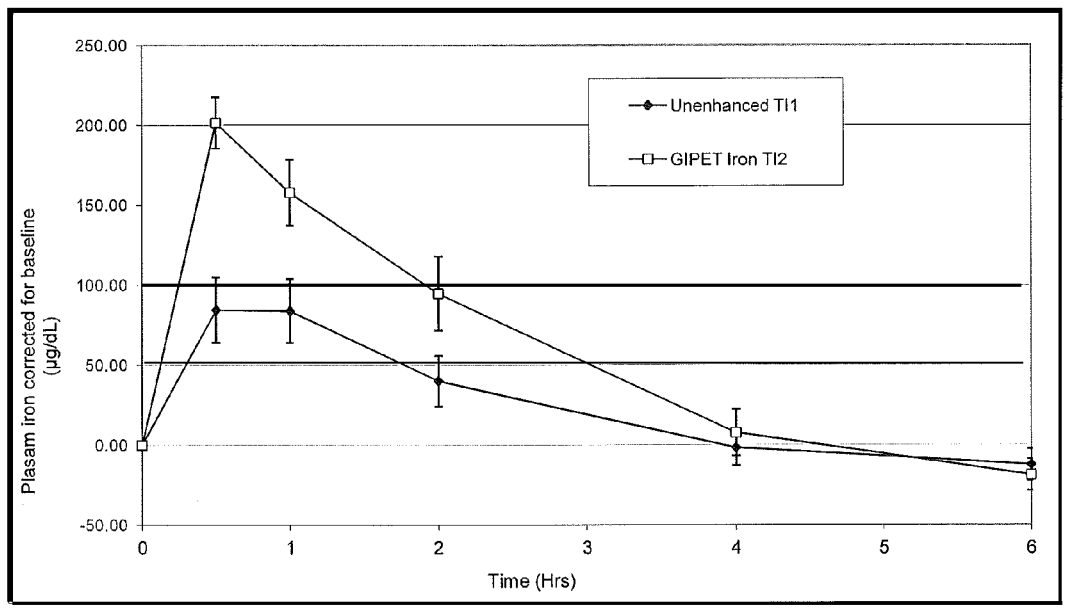
FIG. 19 shows the mean plasma concentration of baseline corrected plasma iron vs. time (6 hours) profiles of the test items after administration to different groups at different periods in female beagle dogs (n=12).

Individual animal baseline corrected plasma iron concentration for the unenhanced TI1 and iron TI2 are presented in Tables 28 and 29 and plotted in FIG. 19.

PK parameters were estimated using plasma iron levels and plasma iron levels corrected for base line data (predose plasma iron concentration). Baseline corrected data was used as T0 plasma iron varied by animal and by period values, which can be presumed to be reflective of variations of the endogenous iron pool. For baseline corrected plasma iron levels, the negative values were considered as zero for AUC calculation. The mean PK parameters of the test and reference items based on total plasma iron and baseline corrected iron are summarized in Table 30.

The relative oral bioavailability ($F_{rel}$) of iron TI2 was calculated using extent of absorption until 6 hours ($AUC_{0-6}$) as the animals were fed a normal iron content meal after 6 hours. The $AUC_{0-6h}$ and the $C_{max}$ ratios demonstrate that iron TI2 showed superior oral absorption of iron to the ferrous sulfate solution (TI1). iron TI2 showed a 3.45-fold increase (n=11) in relative oral bioavailability compared to TI1 (unenhanced oral ferrous sulfate) (Table 31).

The difference in magnitude of absorption in group B for the two formulations (ref Table 32) was relatively low. This may be attributable to predose iron levels being lower prior to dosing the reference formulation than prior to dosing the iron formulation (66±10 μg/dL vs. 83±18 μg/dL).

TABLE 28

Ferrous Sulphate unenhanced TI1 Individual animal's baseline corrected plasma iron concentration μg/dL and AUCs

| | | | Plasma Iron conc. (μg/dL) | | | | | | AUC |
|---|---|---|---|---|---|---|---|---|---|
| | | | | Time(hr) | | | | | |
| Dog ID | Period | Test Item | 0 | 0.5 | 1 | 2 | 4 | 6 | (0-6 hr) |
| Dog 1 | 1 | TI1 | 0 | 0 | 0 | 0 | 0 | 0 | — |
| Dog 2 | 1 | TI1 | 0 | 149 | 123.5 | 78.5 | 53.5 | 0.5 | 392.38 |
| Dog 3 | 1 | TI1 | 0 | 22 | 52.5 | 4 | 0 | 0 | 56.38 |
| Dog 4 | 1 | TI1 | 0 | 44.5 | 43.5 | 30.5 | 2.5 | 3.5 | 109.13 |
| Dog 5 | 1 | TI1 | 0 | 56.5 | 39.5 | 20.5 | 0 | 0 | 88.63 |
| Dog 6 | 1 | TI1 | 0 | 135.5 | 158.5 | 94.5 | 7.5 | 0 | 343.38 |
| Dog 7 | 2 | TI1 | 0 | 52 | 46 | 0 | 0 | 0 | 60.5 |
| Dog 8 | 2 | TI1 | 0 | 57 | 72 | 35 | 7 | 2 | 151 |
| Dog 9 | 2 | TI1 | 0 | 132 | 89 | 40 | 15 | 11 | 233.75 |
| Dog 10 | 2 | TI1 | 0 | 177 | 154 | 69 | 35 | 27 | 404.5 |
| Dog 11 | 2 | TI1 | 0 | 185 | 183 | 113 | 14 | 0 | 427.25 |
| Dog 12 | 2 | TI1 | 0 | 51 | 116 | 89 | 19 | 11 | 295 |

TABLE 29

Iron TI2 Individual animal's baseline corrected plasma
iron concentration μg/dL, AUCs, and $F_{rel}$ (fold v control)

| Dog ID | Period | Test Item | Plasma Iron conc. (μg/dL) Time(hr) | | | | | | AUC (0-6 hr) | Frel (fold v control) |
|---|---|---|---|---|---|---|---|---|---|---|
| | | | 0 | 0.5 | 1 | 2 | 4 | 6 | | |
| Dog 1 | 2 | TI2 | 0 | 171 | 142 | 100 | 25 | 0 | 392.00 | — |
| Dog 2 | 2 | TI2 | 0 | 245 | 173 | 68 | 0 | 0 | 354.25 | 0.90 |
| Dog 3 | 2 | TI2 | 0 | 219 | 173 | 149 | 41 | 0 | 544.75 | 9.66 |
| Dog 4 | 2 | TI2 | 0 | 231 | 238 | 243 | 105 | 31 | 899.50 | 8.24 |
| Dog 5 | 2 | TI2 | 0 | 238 | 166 | 101 | 14 | 0 | 423.00 | 4.77 |
| Dog 6 | 2 | TI2 | 0 | 313 | 325 | 224 | 63 | 7 | 869.25 | 2.53 |
| Dog 7 | 1 | TI2 | 0 | 236.5 | 164.5 | 108.5 | 23.5 | 11.5 | 462.88 | 7.65 |
| Dog 8 | 1 | TI2 | 0 | 187.5 | 155 | 81 | 5 | 0 | 341.50 | 2.26 |
| Dog 9 | 1 | TI2 | 0 | 132.5 | 81 | 0 | 0 | 0 | 127.00 | 0.54 |
| Dog 10 | 1 | TI2 | 0 | 172.5 | 87 | 11.5 | 0 | 0 | 168.75 | 0.42 |
| Dog 11 | 1 | TI2 | 0 | 157.5 | 124 | 58 | 0 | 0 | 258.75 | 0.61 |
| Dog 12 | 1 | TI2 | 0 | 116.5 | 66.5 | 0 | 0 | 0 | 108.13 | 0.37 |

TABLE 30

Mean pharmacokinetics of the test items (n = 12 or 11)

| PK parameter | Unenhanced (TI1) | | Iron (TI2) | |
|---|---|---|---|---|
| | Total plasma Iron | Base line corrected* | Total plasma Iron | Base line corrected* |
| $AUC_{0-6}$ μg/dl * h (% RSD) | 626.90 ± 43.43 (24.00) | 213.49 ± 44.57 (72.31) | 874.13 ± 77.48 (30.70) | 412.48 ± 74.47 (62.54) |
| $F_{Rel(0-6)}$ Fold Vs Unenhanced | | | 1.47 ± 0.17 (40.48) | 3.45 ± 1.07** (102.44) |
| Cmax μg/dl (% RSD) | 179.17 ± 12.63 (24.43) | 108.64 ± 15.75** (50.21) | 289.71 ± 14.75 (17.64) | 203.67 ± 16.87 (28.69) |
| Tmax Hrs (% RSD) | 0.63 ± 0.09 (49.73) | 0.68 ± 0.07** (37.00) | 0.67 ± 0.13 (66.57) | 0.67 ± 0.13 (66.57) |
| Ratio of Cmax Vs Unenhanced | | | 1.71 ± 0.16 (31.92) | 2.59 ± 0.51 (65.73) |

*Negative values were set to zero for the purposes of AUC calculation as this represents no/or negligible absorption
**Calculated T0-6 hrs interval,
**n = 11 as one animal in unenhanced group had no values greater than baseline, hence cannot used be for calculation of Frel. Dog 1 was omitted from analysis.

TABLE 31

Summary of the relative oral bioavailability of the test items dosed
at different intervals in different groups

| Groups | Relative oral bioavailability (Frel Fold Increase ± SEM) (Cmax Ratio) | |
|---|---|---|
| | Total plasma Iron | Base line corrected Plasma Iron |
| Overall (n = 12) | 1.47 ± 0.17 (1.71 ± 0.16) | 3.45 ± 1.07* (2.59 ± 0.51) |
| Group A | 1.86 ± 0.25 (2.01 ± 0.23) | 5.22 ± 1.66 (3.51 ± 1.44) |
| Group B | 1.08 ± 0.09 (1.41 ± 0.14) | 1.97 ± 1.17 (1.83 ± 0.61) |

*n = 11, Frel was assessed for each dosing period since the iron load at baseline will impact iron absorption.

Summary of Induction of Iron Deficiency

Figure 20:
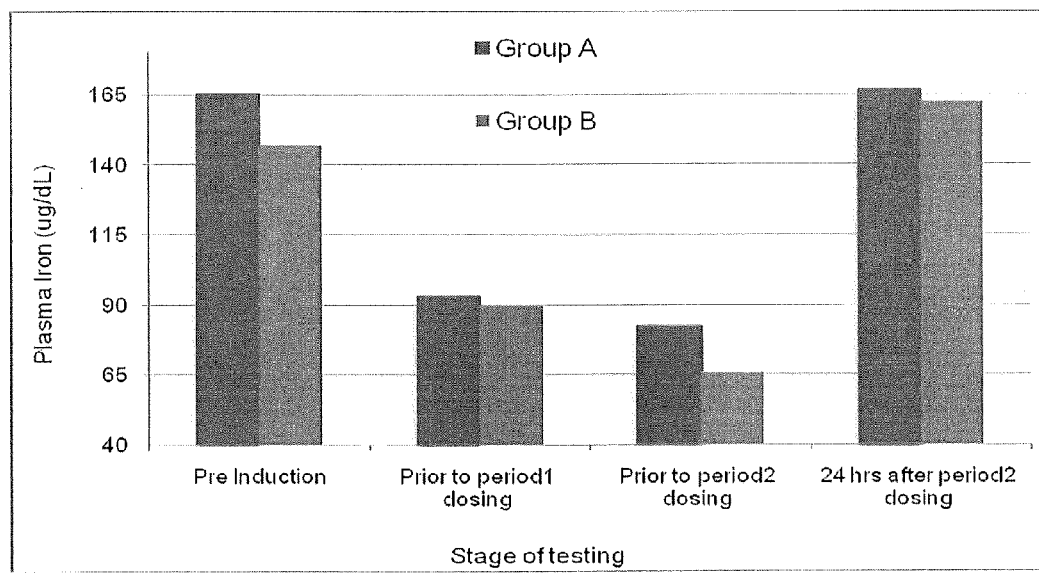
FIG. 20 shows plasma iron levels at key stages of the study.

The animals reached an iron deficient state as defined in the protocol (reduction of plasma iron levels of ~25% and/or a drop ~20% in hematocrit) (Table 32, FIG. 20) prior to the initial dosing.

The plasma iron levels were analyzed prior to dose administration on Days 0, 5, 11 and 12 and were reduced by at least 25% relative pre-induction phase (Day 0) for all animals, except one subject, Dog 3. However, this animal was also included in the study analysis as hematocrit levels were within the acceptable target (Refer to Tables 33 and 34).

At the end of the 24 hours wash-out following the Period 1 dose administration, iron levels were still deficient for both groups (82.5 μg/dL Group A and 66.0 μg/dL Group B).

TABLE 32

Summary of plasma iron and hematocrit (% PCV) levels at key stages
(Mean ± SD, n = 6)

| Period of Testing | Group A | | Group B | |
|---|---|---|---|---|
| | % PCV | Plasma Iron (μg/dL) | % PCV | Plasma Iron (μg/dL) |
| Pre Induction | 52 ± 2 | 165 ± 69 | 51 ± 4 | 147 ± 28 |
| Pre-Period 1 Dosing | 35 ± 2 | 93 ± 55 | 32 ± 2 | 90 ± 30 |
| Pre-Period 2 Dosing | | 83 ± 44 | | 66 ± 24 |

TABLE 33

Plasma iron levels of individual animals during the induction of iron deficient state

| Dog No (ID) | Day 0 | Day 5 | Day 11 | Day 12 | % Reduction |
|---|---|---|---|---|---|
| Dog 1 (1437284) | 293 | 412 | 87 | 147.5 | 50 |
| Dog 2 (1544676) | 128 | 270 | 94 | 55.5 | 57 |
| Dog 3 (1454138) | 121 | 134 | 111 | 176.5 | −46 |
| Dog 4 (1544749) | 118 | 243 | 133 | 69.5 | 41 |
| Dog 5 (1175018) | n/a* | 196 | 83 | 71.5 | 64 |
| Dog 6 (1451716) | 135 | 203 | 41 | 38.5 | 71 |
| Dog 7 (1544765) | 149 | 138 | 71 | 57.5 | 61 |
| Dog 8 (1439686) | 112 | 163 | 46 | 73 | 35 |
| Dog 9 (1444264) | 152 | 258 | 183 | 88 | 42 |
| Dog 10 (1544382) | 196 | 219 | 132 | 144.5 | 26 |
| Dog 11 (1436946) | 133 | 108 | 71 | 80 | 40 |
| Dog 12 (1439163) | 139 | 178 | 70 | 94.5 | 32 |

*Data not available at this point since this dog was added to the study at a later date.

TABLE 34

Hematocrit levels (% PCV) of the animals during the induction of iron deficient state

| | Hematocrit levels (% PCV) | | | | | | | | | |
|---|---|---|---|---|---|---|---|---|---|---|
| Dog No (ID) | Day 0 | Day 1 | Day 4 | Day 5 | Day 6 | Day 7 | Day 8 | Day 11 | Day 12 | % Reduction |
| Dog 1 (1437284) | 52 | 54 | 48 | 30 | 38 | 42 | 36 | 46 | 34 | 35 |
| Dog 2 (1544676) | 54 | 42 | 54 | 38 | 40 | 40 | 34 | 44 | 34 | 37 |
| Dog 3 (1454138) | 52 | 56 | 56 | 38 | 42 | 42 | 34 | 42 | 38 | 27 |
| Dog 4 (1544749) | 48 | 44 | 44 | 40 | 40 | 38 | 32 | 40 | 36 | 25 |
| Dog 5 (1175018) | n/a* | n/a* | n/a* | 54 | 44 | 40 | 34 | 36 | 34 | 37 |
| Dog 6 (1451716) | 54 | 44 | 50 | 42 | 36 | 38 | 28 | 42 | 32 | 41 |
| Dog 7 (1544765) | 44 | 42 | 36 | 38 | 36 | 38 | 28 | 32 | 34 | 23 |
| Dog 8 (1439686) | 56 | 46 | 52 | 40 | 38 | 26 | 36 | 42 | 36 | 36 |
| Dog 9 (1444264) | 50 | 44 | 46 | 48 | 34 | 36 | 34 | 42 | 30 | 40 |
| Dog 10 (1544382) | 48 | 40 | 42 | 48 | 32 | 40 | 36 | 46 | 32 | 33 |
| Dog 11 (1436946) | 52 | 52 | 52 | 40 | 36 | 42 | 36 | 40 | 30 | 42 |
| Dog 12 (1439163) | 54 | 50 | 52 | 44 | 38 | 42 | 38 | 42 | 32 | 41 |

*Data not available during these points since this dog was added to the study at a later date.

Administration Effects/Potential Issues

A summary of the clinical observations noted after test item dosing are detailed in Table 35 below. As expected, dogs had varied plasma iron and % PCV levels at the completion of the anemia induction period. Iron deficiency criteria were met in all animals and were deemed sufficient for the purposes of the study.

TABLE 35

Summary of clinical observations after dosing of each Test Item

| Study Period | Test Item | Clinical Observations* |
|---|---|---|
| Period 1 | Test Item 1 Ferrous sulfate | No adverse clinical observations |
| | Test Item 2 | Dog7 (1544765) vomited 5 mL within 1 h post administration. |

TABLE 35-continued

Summary of clinical observations after dosing of each Test Item

| Study Period | Test Item | Clinical Observations* |
|---|---|---|
| | Iron | Oedema/swelling was noticed at surgical port site within ~2 hours (noticed 4 hr 13 min) |
| | | Dog11 (1436946) vomited 20 mL within 8 minutes post administration. |
| | | Dog12 (1439163) had severe vomiting post administration at following intervals. |
| | | 20 mL within 4 minutes + 10 mL 9 minutes later + 10 mL 7 minutes later + 5 mL 1 hr 13 minutes later + 6 mL 1 hr 38 minutes later |
| Period 2 | Test Item 2 Iron | Dog1 (1437284) vomited 8 mL within 10 minutes post administration and another 10 mL 53 minutes later, and also had diarrhoea 2 minutes later (1 hour 5 minutes post administration) |
| | | Dog3 (1454138) had diarrhoea at 1 hour 2 mintutes post dose administration. |
| | Test Item 1 Ferrous sulfate | Dog7 (1544765) has Oedema/swelling and was noticed at surgical port site prior to dose administration. |
| | | No adverse clinical observations for other dogs |

*Only subjects (dogs) showing significant signs of side effects were included, all other animals used in the study had no apparent signs of side effects.

Conclusions

This study summarizes relative performance of an enhanced iron formulation on the oral absorption of iron compared to an unenhanced formulation of ferrous sulfate in an iron deficient dog model designed for this study. To evaluate relative oral bioavailability, the PK parameters were calculated based on fasting plasma iron levels (animals were fed 6 hours post dosing) using measured levels, and levels corrected for baseline levels (obtained immediately prior to dosing). Iron deficiency state was deemed to be adequate for the purposes of the study as the chosen plasma iron and hematocrit targets were achieved prior to dose administration in each period. The results of the study demonstrate that iron TI2 showed higher systemic absorption of iron compared to ferrous sulfate TI1 in different groups and different dosing periods of this two way crossover study. The relative oral bioavailability ($F_{rel}$) of iron TI2 calculated using extent of absorption until 6 hours ($AUC_{0-6}$) showed a 3.45-fold increase (n=11) in relative oral bioavailability compared to an intraduodenally administered ferrous sulfate solution (both solutions contained equal amounts of elemental iron. Twelve iron deficient female beagle dogs administered two single intraduodenal doses of TI1 (Ferrous Sulfate Formulation) and iron TI2 (Enhanced Formulation) did not exhibit death, morbidity, or severe adverse clinical signs. Clinical signs associated with dose administration of iron TI2 Formulation were mild and limited to vomiting and diarrhea.

Individual Animal Raw Data

Tables 36-47 show additional mean pharmacokinetics values and individual animal data.

TABLE 36

Mean plasma concentration vs. time profiles of the test items dosed at different periods in different groups Plasma Total Concentrations; μg/dL Mean ± SEM, n = 6 (*plasma iron corrected for base line Mean ± SEM, n = 6)

| | Period 1 | | Period 2 | |
|---|---|---|---|---|
| Time (Hrs) | Group A Unenhanced TI1 | Group B Iron TI2 | Group A Iron TI2 | Group B Unenhanced TI1 |
| 0 | 93 ± 23 | 90 ± 12 | 83 ± 18 | 66 ± 10 |
| | (0 ± 0) | (0 ± 0) | (0 ± 0) | (0 ± 0) |
| 0.5 | 153 ± 18 | 257 ± 17 | 319 ± 15 | 175 ± 25 |
| | (60 ± 30) | (167 ± 17) | (236 ± 19) | (109 ± 26) |
| 1 | 151 ± 24 | 203 ± 13 | 285 ± 18 | 176 ± 17 |
| | (58 ± 33) | (113 ± 17) | (203 ± 28) | (110 ± 21) |
| 2 | 117 ± 17 | 132 ± 14 | 230 ± 26 | 123 ± 13 |
| | (24 ± 26) | (42 ± 19) | (148 ± 29) | (57 ± 17) |
| 4 | 79 ± 13 | 64 ± 6 | 124 ± 19 | 77 ± 6 |
| | (−14 ± 20) | (−26 ± 15) | (41 ± 16) | (11 ± 8) |
| 6 | 65 ± 9 | 56 ± 5 | 79 ± 13 | 69 ± 6 |
| | (−28 ± 16) | (−34 ± 16) | (−4 ± 9) | (3 ± 8) |
| 24 | 83 ± 18 | 66 ± 10 | 167 ± 31 | 162 ± 31 |
| | (−11 ± 14) | (−24 ± 20) | (84 ± 24) | (96 ± 34) |

*Plasma iron corrected for baseline (CT-T0); calculated by subtracting baseline plasma iron value (T0). i.e., CT plasma concentration at each interval, T0 Plasma concentration prior to dose administration.

TABLE 37

Mean pharmacokinetics of the test items based on total plasma iron in different groups

| | Period 1 | | Period 2 | |
|---|---|---|---|---|
| PK parameter# | Group A Unenhanced | Group B Iron Form B | Group A Iron Form B | Group B Unenhanced |
| $AUC_{0-6}$ μg/dl * h (% RSD) | 611.04 ± 77.03 (30.88) | 683.13 ± 52.30 (18.75) | 1065.13 ± 95.31 (21.92) | 642.75 ± 47.61 (18.14) |
| $F_{Rel(0-6)}$ Fold vs. Unenhanced | * | 1.08 ± 0.09** (19.96) | 1.86 ± 0.25* (32.30) | ** |
| $C_{max}$ | 170.00 ± 18.98 | 256.75 ± 17.14 | 322.67 ± 15.15 | 188.33 ± 17.56 |

TABLE 37-continued

Mean pharmacokinetics of the test items based on total plasma iron in different groups

|  | Period 1 | | Period 2 | |
| --- | --- | --- | --- | --- |
| PK parameter# | Group A Unenhanced | Group B Iron Form B | Group A Iron Form B | Group B Unenhanced |
| μg/dl (% RSD) | (27.35) | (16.35) | (11.50) | (22.84) |
| $T_{max}$ Hrs (% RSD) | 0.58 ± 0.15 (64.52) | 0.50 ± 0.00 (0.00) | 0.83 ± 0.25 (72.66) | 0.67 ± 0.11 (38.73) |
| Ratio of $C_{max}$ vs. Unenhanced | * | 1.41 ± 0.14** | 2.01 ± 0.23* | ** |

Mean ± SEM (n = 6).
* Group A comparison;
**Group B comparison.

TABLE 38

Mean pharmacokinetics of the test items based on plasma iron corrected for baseline

|  | Period 1 | | Period 2 | |
| --- | --- | --- | --- | --- |
| PK parameter | Group A Unenhanced | Group B Iron Form B | Group A Iron Form B | Group B Unenhanced |
| $AUC_{0-6}$ μg/dl * h (% RSD) | 164.98 ± 66.21 (98.30) | 244.50 ± 56.40 (56.51) | 580.46 ± 99.66 (42.05) | 262.00 ± 58.43 (54.63) |
| $F_{Rel(0-6)}$ Fold vs. Unenhanced | * | 1.97 ± 1.17** (145.47) | 5.22 ± 1.66*# (70.96) | ** |
| $C_{max}$ μg/dl (% RSD) | 92.90 ± 25.25 (61.23) | 167.17 ± 17.43 (25.54) | 240.17 ± 20.38 (20.79) | 122.33 ± 22.01 (44.06) |
| $T_{max}$ Hrs (% RSD) | 0.67 ± 0.11 (38.73) | 0.50 ± 0.00 (0.00) | 0.83 ± 0.25 (72.66) | 0.67 ± 0.11 (38.73) |
| Ratio of $C_{max}$ vs. Unenhanced | * | 1.83 ± 0.61** | 3.51 ± 1.44*# | ** |

Mean ± SEM (n = 6).
*#n = 5
* Group A comparison;
**Group B comparison

TABLE 39

Individual dog plasma iron concentrations and PK data after dose administration of Unenhanced-TI1 (Ferrous Sulfate) at Period 1 in Group A animals Total Plasma Iron concentration μg/mL

| TIME | Dog 1 ID 1437284 | Dog 2 ID 1544676 | Dog 3 ID 1454138 | Dog 4 ID 1544749 | Dog 5 ID 1175018 | Dog 6 ID 1451716 | Mean ± SEM (n = 6) | % RSD (n = 6) |
| --- | --- | --- | --- | --- | --- | --- | --- | --- |
| 0 | 147.5 | 55.5 | 176.5 | 69.5 | 71.5 | 38.5 | 93.17 ± 22.61 | 59.44 |
| 0.5 | 99.0 | 204.5 | 198.5 | 114.0 | 128.0 | 174.0 | 153.00 ± 18.46 | 29.56 |
| 1 | 76.0 | 179.0 | 229.0 | 113.0 | 111.0 | 197.0 | 150.83 ± 24.26 | 39.39 |
| 2 | 61.0 | 134.0 | 180.5 | 100.0 | 92.0 | 133.0 | 116.75 ± 16.96 | 35.58 |
| 4 | 59.0 | 109.0 | 124.0 | 72.0 | 63.0 | 46.0 | 78.83 ± 12.54 | 38.97 |
| 6 | 64.0 | 56.0 | 101.0 | 73.0 | 67.0 | 31.0 | 65.33 ± 9.31 | 34.91 |
| 24 | 104.0 | 52.0 | 136.0 | 54.0 | 122.0 | 27.0 | 82.50 ± 17.99 | 53.41 |
| $AUC_{0-6}$ (μg/dl*h) | 416.88 | 725.38 | 934.88 | 526.13 | 496.13 | 566.88 | 611.04 ± 77.03 | 30.88 |
| $C_{max}$ (μg/dl) | 147.5 | 204.5 | 229.0 | 114.0 | 128.0 | 197.0 | 170.00 ± 18.98 | 27.35 |
| $T_{max}$ (Hrs) | 0.0 | 0.5 | 1.0 | 0.5 | 0.5 | 1.0 | 0.58 ± 0.15 | 64.52 |

TABLE 40

Individual plasma iron concentrations and PK data after dose administration of iron TI2 (Ferric Pyrophosphate soluble) at Period 1 in Group B animals Total Plasma Iron concentration µg/mL

| TIME | Dog 7 ID 1544765 | Dog 8 ID 1439686 | Dog 9 ID 1444264 | Dog 10 ID 1544382 | Dog 11 ID 1436946 | Dog 12 ID 1439163 | Mean ± SEM (n = 6) | % RSD (n = 6) |
|---|---|---|---|---|---|---|---|---|
| 0 | 57.5 | 73.0 | 88.0 | 144.5 | 80.0 | 94.5 | 89.58 ± 12.16 | 33.26 |
| 0.5 | 294.0 | 260.5 | 220.5 | 317.0 | 237.5 | 211.0 | 256.75 ± 17.14 | 16.35 |
| 1 | 222.0 | 228.0 | 169.0 | 231.5 | 204.0 | 161.0 | 202.58 ± 12.54 | 15.16 |
| 2 | 166.0 | 154.0 | 83.0 | 156.0 | 138.0 | 92.0 | 131.50 ± 14.44 | 26.89 |
| 4 | 81.0 | 78.0 | 46.0 | 64.0 | 62.0 | 51.0 | 63.67 ± 5.72 | 22.00 |
| 6 | 69.0 | 73.0 | 45.0 | 48.0 | 54.0 | 46.0 | 55.83 ± 4.99 | 21.89 |
| 24 | 99.0 | 87.0 | 58.0 | 49.0 | 68.0 | 35.0 | 66.00 ± 9.74 | 36.16 |
| $AUC_{0-6}$ (µg/dl*h) | 807.88 | 779.50 | 520.50 | 778.25 | 676.75 | 535.88 | 683.13 ± 52.30 | 18.75 |
| $F_{Rel(0-6)}$ Fold vs. Unenhanced | 1.42 | 1.16 | 0.89 | 1.11 | 0.81 | 1.06 | 1.08 ± 0.09 | 19.96 |
| $C_{max}$ (µg/dl) | 294.0 | 260.5 | 220.5 | 317.0 | 237.5 | 211.0 | 256.75 ± 17.14 | 16.35 |
| $T_{max}$ (Hrs) | 0.5 | 0.5 | 0.5 | 0.5 | 0.5 | 0.5 | 0.50 ± 0.00 | 0.00 |

TABLE 41

Total plasma iron concentration and PK data of individual dogs after dose administration of Unenhanced TI1 (Ferrous Sulfate) at Period 2 Group B animals Total Plasma Iron concentration µg/mL

| TIME | Dog 7 ID 1544765 | Dog 8 ID 1439686 | Dog 9 ID 1444264 | Dog 10 ID 1544382 | Dog 11 ID 1436946 | Dog 12 ID 1439163 | Mean ± SEM (n = 6) | % RSD (n = 6) |
|---|---|---|---|---|---|---|---|---|
| 0 | 99.0 | 87.0 | 58.0 | 49.0 | 68.0 | 35.0 | 66.00 ± 9.74 | 36.16 |
| 0.5 | 151.0 | 144.0 | 190.0 | 226.0 | 253.0 | 86.0 | 175.00 ± 24.74 | 34.63 |
| 1 | 145.0 | 159.0 | 147.0 | 203.0 | 251.0 | 151.0 | 176.00 ± 17.39 | 24.20 |
| 2 | 92.0 | 122.0 | 98.0 | 118.0 | 181.0 | 124.0 | 122.50 ± 12.88 | 25.75 |
| 4 | 75.0 | 94.0 | 73.0 | 84.0 | 82.0 | 54.0 | 77.00 ± 5.51 | 17.54 |
| 6 | 70.0 | 89.0 | 69.0 | 76.0 | 64.0 | 46.0 | 69.00 ± 5.79 | 20.54 |
| 24 | 152.0 | 136.0 | 123.0 | 314.0 | 151.0 | 98.0 | 162.33 ± 31.42 | 47.41 |
| $AUC_{0-6}$ (µg/dL*h) | 567.00 | 673.00 | 581.75 | 698.50 | 831.25 | 505.00 | 642.75 ± 47.61 | 18.14 |
| $C_{max}$ (µg/dl) | 151.0# | 159.0 | 190.0 | 226.0# | 253.0 | 151.0 | 188.33 ± 17.56 | 22.84 |
| $T_{max}$ (Hrs) | 0.5# | 1.0 | 0.5 | 0.5# | 0.5 | 1.0 | 0.67 ± 0.11 | 38.73 | based on 0-6 interval

TABLE 42

Total plasma iron concentration and PK data of individual dogs after dose administration of iron TI2 (Ferric pyrophosphate soluble) at Period 2 Group A animals Total Plasma Iron concentration µg/mL

| TIME | Dog 1 ID 1437284 | Dog 2 ID 1544676 | Dog 3 ID 1454138 | Dog 4 ID 1544749 | Dog 5 ID 1175018 | Dog 6 ID 1451716 | Mean ± SEM (n = 6) | % RSD (n = 6) |
|---|---|---|---|---|---|---|---|---|
| 0 | 104.0 | 52.0 | 136.0 | 54.0 | 122.0 | 27.0 | 82.50 ± 17.99 | 53.41 |
| 0.5 | 275.0 | 297.0 | 355.0 | 285.0 | 360.0 | 340.0 | 318.67 ± 15.27 | 11.74 |
| 1 | 246.0 | 225.0 | 309.0 | 292.0 | 288.0 | 352.0 | 285.33 ± 18.48 | 15.86 |
| 2 | 204.0 | 120.0 | 285.0 | 297.0 | 223.0 | 251.0 | 230.00 ± 26.32 | 28.03 |
| 4 | 129.0 | 52.0 | 177.0 | 159.0 | 136.0 | 90.0 | 123.83 ± 18.75 | 37.08 |
| 6 | 104.0 | 43.0 | 112.0 | 85.0 | 93.0 | 34.0 | 78.50 ± 13.25 | 41.34 |
| 24 | 300.0 | 131.0 | 166.0 | 149.0 | 184.0 | 71.0 | 166.83 ± 30.99 | 45.50 |
| $AUC_{0-6}$ (µg/dL*h) | 1016.00 | 657.25 | 1336.75 | 1223.50 | 1126.00 | 1031.25 | 1065.13 ± 95.31 | 21.92 |

TABLE 42-continued

Total plasma iron concentration and PK data of individual dogs after dose administration of iron TI2 (Ferric pyrophosphate soluble) at Period 2 Group A animals Total Plasma Iron concentration µg/mL

| TIME | Dog 1 ID 1437284 | Dog 2 ID 1544676 | Dog 3 ID 1454138 | Dog 4 ID 1544749 | Dog 5 ID 1175018 | Dog 6 ID 1451716 | Mean ± SEM (n = 6) | % RSD (n = 6) |
|---|---|---|---|---|---|---|---|---|
| $F_{Rel(0-6)}$ Fold vs. Unenhanced | 2.44 | 0.91 | 1.43 | 2.33 | 2.27 | 1.82 | 1.86 ± 0.25 | 32.30 |
| $C_{max}$ (µg/dl) | 275.0# | 297.0 | 355.0 | 297.0 | 360.0 | 352.0 | 322.67 ± 15.15 | 11.50 |
| $T_{max}$ (Hrs) | 0.5# | 0.5 | 0.5 | 2.0 | 0.5 | 1.0 | 0.83 ± 0.25 | 72.66 | based on 0-6 interval

TABLE 43

Baseline corrected plasma iron concentration and PK data of individual dogs after dose administration of Unenhanced TI1 (Ferrous Sulfate) at Period 1 in Group A animals Absorbed iron concentration µg/mL*(T0-CT)

| TIME | Dog 1 ID 1437284 | Dog 2 ID 1544676 | Dog 3 ID 1454138 | Dog 4 ID 1544749 | Dog 5 ID 1175018 | Dog 6 ID 1451716 | Mean ± SEM (n = 6) | % RSD (n = 6) |
|---|---|---|---|---|---|---|---|---|
| 0 | 0.0 | 0.0 | 0.0 | 0.0 | 0.0 | 0.0 | 0.00 ± 0.00 | 0.00 |
| 0.5 | −48.5 | 149.0 | 22.0 | 44.5 | 56.5 | 135.5 | 59.83 ± 30.05 | 123.02 |
| 1 | −71.5 | 123.5 | 52.5 | 43.5 | 39.5 | 158.5 | 57.67 ± 32.53 | 138.17 |
| 2 | −86.5 | 78.5 | 4.0 | 30.5 | 20.5 | 94.5 | 23.58 ± 26.21 | 272.20 |
| 4 | −88.5 | 53.5 | −52.5 | 2.5 | −8.5 | 7.5 | −14.33 ± 20.29 | −346.78 |
| 6 | −83.5 | 0.5 | −75.5 | 3.5 | −4.5 | −7.5 | −27.83 ± 16.45 | −144.73 |
| 24 | −43.5 | −3.5 | −40.5 | −15.5 | 50.5 | −11.5 | −10.67 ± 13.89 | −318.88 |
| $AUC_{0-6}$ (µg/dl*h) | 0.00 | 392.38 | 56.38 | 109.13 | 88.63 | 343.38 | 164.98 ± 66.21 | 98.30 |
| $C_{max}$ (µg/dl) | −48.5** | 149.0 | 52.5 | 44.5 | 56.5 | 158.5 | 92.90 ± 25.25# | 61.23# |
| $T_{max}$ (Hrs) | 0.5** | 0.5 | 1.0 | 0.5 | 0.5 | 1.0 | 0.67 ± 0.11 | 38.73 |

*T0 Plasma Iron concentration, CT Plasma Iron concentration at each interval of time after dose administration. All negative values set at zero for purposes of calculating AUC values.
**Calculated over 0-6 hour period.
n = 5

TABLE 44

Baseline corrected plasma iron concentration and PK data of individual dogs after dose administration of iron TI2 (Ferric pyrophosphate soluble) at Period 1 in Group B animals Absorbed iron concentration µg/mL*(T0-CT)

| TIME | Dog 7 ID 1544765 | Dog 8 ID 1439686 | Dog 9 ID 1444264 | Dog 10 ID 1544382 | Dog 11 ID 1436946 | Dog 12 ID 1439163 | Mean ± SEM (n = 6) | % RSD (n = 6) |
|---|---|---|---|---|---|---|---|---|
| 0 | 0.0 | 0.0 | 0.0 | 0.0 | 0.0 | 0.0 | 0.00 ± 0.00 | 0.00 |
| 0.5 | 236.5 | 187.5 | 132.5 | 172.5 | 157.5 | 116.5 | 167.17 ± 17.43 | 25.54 |
| 1 | 164.5 | 155.0 | 81.0 | 87.0 | 124.0 | 66.5 | 113.00 ± 16.73 | 36.27 |
| 2 | 108.5 | 81.0 | −5.0 | 11.5 | 58.0 | −2.5 | 41.92 ± 19.42 | 113.51 |
| 4 | 23.5 | 5.0 | −42.0 | −80.5 | −18.0 | −43.5 | −25.92 ± 15.28 | −144.45 |
| 6 | 11.5 | 0.0 | −43.0 | −96.5 | −26.0 | −48.5 | −33.75 ± 15.80 | −114.66 |
| 24 | 41.5 | 14.0 | −30.0 | −95.5 | −12.0 | −59.5 | −23.58 ± 20.24 | −210.19 |
| $AUC_{0-6}$ (µg/dl*h) | 462.88 | 341.50 | 127.00 | 168.75 | 258.75 | 108.13 | 244.50 ± 56.40 | 56.51 |
| $F_{Rel(0-6)}$ Fold vs. Unenhanced | 7.65 | 2.26 | 0.54 | 0.42 | 0.61 | 0.37 | 1.97 ± 1.17 | 145.47 |
| $C_{max}$ (µg/dl) | 236.5 | 187.5 | 132.5 | 172.5 | 157.5 | 116.5 | 167.17 ± 17.43 | 25.54 |

TABLE 44-continued

Baseline corrected plasma iron concentration and PK data of individual dogs after dose administration of iron TI2 (Ferric pyrophosphate soluble) at Period 1 in Group B animals Absorbed iron concentration µg/mL*(T0-CT)

| TIME | Dog 7 ID 1544765 | Dog 8 ID 1439686 | Dog 9 ID 1444264 | Dog 10 ID 1544382 | Dog 11 ID 1436946 | Dog 12 ID 1439163 | Mean ± SEM (n = 6) | % RSD (n = 6) |
|---|---|---|---|---|---|---|---|---|
| $T_{max}$ (Hrs) | 0.5 | 0.5 | 0.5 | 0.5 | 0.5 | 0.5 | 0.50 ± 0.00 | 0.00 |

*T0 Plasma Iron concentration, CT Plasma Iron concentration at each interval of time after dose administration. All negative values set at zero for purposes of calculating AUC values.
**Calculated over 0-6 hour period.

TABLE 45

Baseline corrected plasma iron concentration and PK data of individual dogs after dose administration of TI1 (Ferrous Sulfate) at Period 2 in Group B animals Total Plasma Iron concentration µg/mL

| TIME | Dog 7 ID 1544765 | Dog 8 ID 1439686 | Dog 9 ID 1444264 | Dog 10 ID 1544382 | Dog 11 ID 1436946 | Dog 12 ID 1439163 | Mean ± SEM (n = 6) | % RSD (n = 6) |
|---|---|---|---|---|---|---|---|---|
| 0 | 0.0 | 0.0 | 0.0 | 0.0 | 0.0 | 0.0 | 0.00 ± 0.00 | 0.00 |
| 0.5 | 52.0 | 57.0 | 132.0 | 177.0 | 185.0 | 51.0 | 109.00 ± 25.98 | 58.38 |
| 1 | 46.0 | 72.0 | 89.0 | 154.0 | 183.0 | 116.0 | 110.00 ± 21.04 | 46.85 |
| 2 | −7.0 | 35.0 | 40.0 | 69.0 | 113.0 | 89.0 | 56.50 ± 17.48 | 75.80 |
| 4 | −24.0 | 7.0 | 15.0 | 35.0 | 14.0 | 19.0 | 11.00 ± 7.97 | 177.49 |
| 6 | −29.0 | 2.0 | 11.0 | 27.0 | −4.0 | 11.0 | 3.00 ± 7.70 | 628.58 |
| 24 | 53.0 | 49.0 | 65.0 | 265.0 | 83.0 | 63.0 | 96.33 ± 34.08 | 86.65 |
| $AUC_{0-6}$ (µg/dL*h) | 60.50 | 151.00 | 233.75 | 404.50 | 427.25 | 295.00 | 262.00 ± 58.43 | 54.63 |
| $C_{max}$ (µg/dl) | 52.0# | 72.0 | 132.0 | 177.0# | 185.0 | 116.0 | 122.33 ± 22.01 | 44.06 |
| $T_{max}$ (Hrs) | 0.5# | 1 | 0.5 | 0.5# | 0.5 | 1 | 0.67 ± 0.11 | 38.73 | based on 0-6 interval

TABLE 46

Baseline corrected plasma iron concentration vs. time profiles and PK data of individual dogs after dose administration of TI2 (iron Form B) at Period 2 Group A animals Total Plasma Iron concentration µg/mL

| TIME | Dog 1 ID 1437284 | Dog 2 ID 1544676 | Dog 3 ID 1454138 | Dog 4 ID 1544749 | Dog 5 ID 1175018 | Dog 6 ID 1451716 | Mean ± SEM (n = 6) | % RSD (n = 6) |
|---|---|---|---|---|---|---|---|---|
| 0 | 0.0 | 0.0 | 0.0 | 0.0 | 0.0 | 0.0 | 0.00 ± 0.00 | 0.00 |
| 0.5 | 171.0 | 245.0 | 219.0 | 231.0 | 238.0 | 313.0 | 236.17 ± 18.76 | 19.45 |
| 1 | 142.0 | 173.0 | 173.0 | 238.0 | 166.0 | 325.0 | 202.83 ± 27.69 | 33.44 |
| 2 | 100.0 | 68.0 | 149.0 | 243.0 | 101.0 | 224.0 | 147.50 ± 29.28 | 48.62 |
| 4 | 25.0 | 0.0 | 41.0 | 105.0 | 14.0 | 63.0 | 41.33 ± 15.54 | 92.10 |
| 6 | 0.0 | −9.0 | −24.0 | 31.0 | −29.0 | 7.0 | −4.00 ± 8.97 | −549.09 |
| 24 | 196.0 | 79.0 | 30.0 | 95.0 | 62.0 | 44.0 | 84.33 ± 24.28 | 70.53 |
| $AUC_{0-6}$ (µg/dL*h) | 392.00 | 354.25 | 544.75 | 899.50 | 423.00 | 869.25 | 580.46 ± 99.66 | 42.05 |
| $F_{Rel(0-6)}$ Fold vs. Unenhanced | #DIV/0! | 0.90 | 9.66 | 8.24 | 4.77 | 2.53 | 5.22 ± 1.51 | 70.96 |
| $C_{max}$ (µg/dl) | 171.0# | 245.0 | 219.0 | 243.0 | 238.0 | 325.0 | 240.17 ± 20.38 | 20.79 |
| $T_{max}$ (Hrs) | 0.5# | 0.5 | 0.5 | 2.0 | 0.5 | 1.0 | 0.83 ± 0.25 | 72.66 | based on 0-6 interval

TABLE 47

Mean overall plasma concentration (μg/dL—Mean ± SEM, n = 12) vs. time profiles of the test items

| | Unenhanced | | Iron Form B | |
|---|---|---|---|---|
| Time | Total plasma Iron | Base line corrected* | Total plasma Iron | Base line corrected* |
| 0 | 79.58 ± 12.43 | 0.00 ± 0.00 | 86.04 ± 10.41 | 0.00 ± 0.00 |
| 0.5 | 164.00 ± 15.09 | 84.42 ± 20.34 | 287.71 ± 14.38 | 201.67 ± 16.04 |
| 1 | 163.42 ± 14.73 | 83.83 ± 20.08 | 243.96 ± 16.40 | 157.92 ± 20.53 |
| 2 | 119.63 ± 10.19 | 40.04 ± 15.82 | 180.75 ± 20.62 | 94.71 ± 23.11 |
| 4 | 77.92 ± 6.54 | −1.67 ± 11.07 | 93.75 ± 13.02 | 7.71 ± 14.52 |
| 6 | 67.17 ± 5.26 | −12.42 ± 9.83 | 67.17 ± 7.56 | −18.88 ± 9.75 |
| 24 | 122.42 ± 21.04 | 42.83 ± 23.83 | 116.42 ± 21.70 | 30.38 ± 22.18 |

*Amount plasma iron corrected for baseline (CT-T0); calculated by subtracting baseline plasma iron value (T0). i.e. CT plasma concentration at each interval, T0 Plasma concentration prior to dose administration.

Example 13

Effect of Dosage Forms on Iron Feedback Mechanism

Data collected in Example 12 were evaluated to determine the relationship between iron absorption and the iron levels at baseline for each of the study periods. It was found in this analysis that the amount of iron absorbed from the unenhanced formulation decreased as the iron levels at baseline increased. FIG. 21 demonstrates this relationship. The unenhanced AUCs vs. predose iron levels displays a clear relationship between predose iron levels and absorbed iron. Animals with higher predose iron levels absorbed less iron from the unenhanced test formulation. This fits with the theory that iron is absorbed by active transport and there is a feedback mechanism.

In contrast, for the enhanced formulation, this decrease in absorption with increased baseline iron levels was not similarly seen. In fact, the dog with the third highest baseline level was the second highest absorbing subject. FIG. 22, the plot of enhanced iron AUCs vs. predose iron levels, demonstrates this. This is likely a result of paracellular and transcellular absorption of iron promoted by the enhanced formulation caused by the formation of mixed micelles of the iron and the enhancer system. Hence, while absorption of iron by active transport is suppressed when predose iron levels rise, absorption by paracellular and transcellular absorption promoted by enhancers of the invention is not affected by negative feedback.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A pharmaceutical composition comprising an iron compound, an absorption enhancer, wherein the absorption enhancer is a medium chain fatty acid salt having a carbon chain length of from about 4 to about 20 carbon atoms, and a solubilizer in an amount sufficient to increase the solubility of the iron compound and/or the absorption enhancer, wherein the solubilizer is present in an amount of about 2% to about 25% by weight, and wherein the composition does not involve chemical modification of the iron compound.

2. A pharmaceutical composition comprising an iron compound, an absorption enhancer, and a solubilizer in an amount sufficient to increase the solubility of the iron compound and/or the absorption enhancer, wherein the solubilizer is present in an amount of about 2% to about 25% by weight, and wherein the composition provides a bioavailability of iron that is at least 1.5 times greater than the bioavailability provided by a composition comprising ferrous sulfate that does not contain an absorption enhancer.

3. The pharmaceutical composition of claim 2, wherein the composition provides a bioavailability of iron that is at least four times greater than the bioavailability provided by a ferrous sulfate tablet that does not contain an absorption enhancer.

4. The pharmaceutical composition of claim 1, wherein the iron compound is an iron salt, an iron chelate, or an iron complex.

5. The pharmaceutical composition of claim 4, wherein the iron compound is a ferric complex.

6. The pharmaceutical composition of claim 4, wherein the iron compound is a complex of iron with EDTA and sodium.

7. The pharmaceutical composition of claim 4, wherein the iron compound is a ferric chelate.

8. The pharmaceutical composition of claim 4, wherein the iron compound is ferric pyrophosphate.

9. The pharmaceutical composition of claim 4, wherein the iron compound is soluble ferric pyrophosphate.

10. The pharmaceutical composition of claim 1, wherein the medium chain fatty acid salt is solid at room temperature.

11. The pharmaceutical composition of claim 1, wherein the carbon chain length is from 8 to 14 carbon atoms.

12. The pharmaceutical composition of claim 1, wherein the absorption enhancer is a sodium salt of a medium chain fatty acid.

13. The pharmaceutical composition of claim 1, wherein the absorption enhancer is selected from the group consisting of sodium caprylate, sodium caprate, and sodium laurate.

14. The pharmaceutical composition of claim 1, wherein the medium chain fatty acid salt is the only absorption enhancer in the composition.

15. The pharmaceutical composition of claim 1, wherein the pharmaceutical composition comprises more than one medium chain fatty acid salt.

16. The pharmaceutical composition of claim 1, wherein the iron compound is the only active agent in the composition.

17. The pharmaceutical composition of claim 1, wherein the composition further comprises an additional active agent.

18. The pharmaceutical composition of claim 17, wherein the additional active agent is selected from the group consisting of folic acid, vitamin A, vitamin B (all series), vitamin C, vitamin D, vitamin E, calcium, chromium, copper, magnesium, manganese, potassium, selenium, zinc, phosphorus, iodine, biotin, inositol, para-amino benzoic acid, choline, and any combination thereof.

19. The pharmaceutical composition of claim 1, wherein the composition further comprises an auxiliary excipient.

20. The pharmaceutical composition of claim 1, wherein the solubilizer is an organic chelation agent.

21. The pharmaceutical composition of claim 20, wherein the solubilizer is citric acid, a salt of citric acid, ascorbic acid, or a salt of ascorbic acid.

22. The pharmaceutical composition of claim 1, wherein the solubilizer is present in an amount sufficient to increase the dissolution rate of the iron compound and the enhancer by about 5% and achieve at least about 80% dissolution of both the iron compound and the enhancer in 3 hours.

23. An oral dosage form comprising the pharmaceutical composition of claim 1.

24. The oral dosage form of claim 23, which is a liquid oral dosage form.

25. The oral dosage form of claim 23, which is a solid oral dosage form.

26. The oral dosage form of claim 23, comprising about 1 mg to about 200 mg elemental iron.

27. The solid oral dosage form of claim 25, wherein the dosage form is a tablet, a capsule, a multiparticulate, or a powder dosage form.

28. The solid oral dosage form of claim 23, wherein the dosage form is a controlled release dosage form.

29. The solid oral dosage form of claim 23, wherein the dosage form is a delayed release dosage form.

30. The solid oral dosage form of claim 23, wherein the dosage form further comprises a rate controlling polymer material.

31. The solid oral dosage form of claim 25, wherein the dosage form is an enteric coated dosage form.

32. The solid oral dosage form of claim 30, wherein the rate-controlling polymer is hydroxypropyl methylcellulose.

33. The solid oral dosage form of claim 30, wherein the rate-controlling polymer is a polymer of acrylic or methacrylic acid or their respective esters or copolymers of acrylic or methacrylic acid or their respective esters.

34. The solid oral dosage form of claim 25, wherein the iron compound, the absorption enhancer, and at least one auxiliary excipient are compressed into tablet form prior to coating with a rate controlling polymer or a delayed release polymer.

35. The solid oral dosage form according to claim 25, wherein the iron compound, the absorption enhancer, at least one auxiliary excipient, and the rate-controlling polymer material are combined into a multiparticulate form.

36. The solid oral dosage form according to claim 35, wherein the multiparticulate is encapsulated in capsules and optionally coated with a rate-controlling polymer or a delayed release polymer.

37. A method of orally delivering iron to a subject, comprising administering to the subject the oral dosage form of claim 23.

38. The pharmaceutical composition of claim 2, wherein the solubilizer is an organic chelation agent.

39. The pharmaceutical composition of claim 38, wherein the solubilizer is citric acid, a salt of citric acid, ascorbic acid, or a salt of ascorbic acid.

40. The pharmaceutical composition of claim 2, wherein the solubilizer is present in an amount sufficient to increase the dissolution rate of the iron compound and the enhancer by about 5% and achieve at least about 80% dissolution of both the iron compound and the enhancer in 3 hours.

41. An oral dosage form comprising the pharmaceutical composition of claim 2.

42. A method of orally delivering iron to a subject, comprising administering to the subject the oral dosage form of claim 41.

* * * * *